US012251550B2

(12) United States Patent
Quelenn et al.

(10) Patent No.: US 12,251,550 B2
(45) Date of Patent: Mar. 18, 2025

(54) BLOOD PUMPS HAVING AN ENCAPSULATED ACTUATOR

(71) Applicant: CorWave SA, Clichy (FR)

(72) Inventors: Pierre-Yves Quelenn, Asniere-sur-Seine (FR); Carl N. Botterbusch, Wyomissing, PA (US); Trevor Snyder, La Celle-Saint-Cloud (FR); Francois Cornat, Paris (FR); Francesca Condemi, Levallois-Perret (FR); Petrus Le Blanc, Rancho Cordova, CA (US); Antoine Olivé, Asnieres sur Seine (FR)

(73) Assignee: CorWave SA, Clichy (FR)

( * ) Notice: Subject to any disclaimer, the term of this patent is extended or adjusted under 35 U.S.C. 154(b) by 0 days.

(21) Appl. No.: 18/306,021

(22) Filed: Apr. 24, 2023

(65) Prior Publication Data

US 2023/0338728 A1    Oct. 26, 2023

Related U.S. Application Data

(60) Provisional application No. 63/363,635, filed on Apr. 26, 2022.

(30) Foreign Application Priority Data

Apr. 26, 2022 (EP) .................................... 22315090

(51) Int. Cl.
*A61M 60/462* (2021.01)
*A61M 60/835* (2021.01)

(52) U.S. Cl.
CPC ........ *A61M 60/462* (2021.01); *A61M 60/835* (2021.01)

(58) Field of Classification Search
CPC .................................................. A61M 60/462
See application file for complete search history.

(56) References Cited

U.S. PATENT DOCUMENTS 2,842,067 A    7/1958    John et al.
3,107,630 A   10/1963   Johnson et al.
(Continued)

FOREIGN PATENT DOCUMENTS

AU    2013203301 A1    5/2013
AU    2013203301 B2   10/2015
(Continued)

OTHER PUBLICATIONS

Ando, et al., Electrocardiogram-Synchronized Rotational Speed Change Mode in Rotary Pumps Could Improve Pulsatility, Artificial Organs, 35(10):941-947 (2011).
(Continued)

*Primary Examiner* — Jacqueline Woznicki
(74) *Attorney, Agent, or Firm* — Greenberg Traurig, LLP; Christopher C. Bolten; Robert D. Ward

(57) ABSTRACT

Systems and methods for generating blood flow with a blood pump including a membrane and an encapsulated actuator are described. The pump may be implantable and may include a stator assembly, an electromagnetic assembly supported by the stator assembly, a magnetic assembly, one or more springs attached to the stator and the magnetic assembly, and encapsulation portions that connect the magnetic assembly to the stator assembly. The magnetic assembly may further be coupled to a membrane assembly including a flexible membrane. The electromagnetic assembly may be selectively activated to cause the magnetic assembly to reciprocate, thereby causing the membrane assembly to reciprocate and inducing wavelike undulations in the flexible membrane to pump blood from an inlet to an outlet of the pump. The encapsulation portions may prevent blood from interacting with an interior moving portion of the pump thereby reducing the risk of hemolysis.

17 Claims, 33 Drawing Sheets

(56) References Cited

U.S. PATENT DOCUMENTS

| | | |
|---|---|---|
| 3,165,061 A | 1/1965 | Smith et al. |
| 3,608,088 A | 9/1971 | Dorman et al. |
| 3,620,651 A | 11/1971 | Peter |
| 3,743,446 A | 7/1973 | Mandroian |
| 3,765,175 A | 10/1973 | Ohnaka |
| 4,063,826 A | 12/1977 | Riepe |
| 4,277,706 A | 7/1981 | Isaacson |
| 4,384,830 A | 5/1983 | Wakelin |
| 4,484,095 A | 11/1984 | Neumann |
| 4,488,854 A | 12/1984 | Miller |
| 4,498,851 A | 2/1985 | Kolm et al. |
| 4,648,807 A | 3/1987 | Tippetts et al. |
| 4,753,221 A | 6/1988 | Kensey et al. |
| 4,906,229 A | 3/1990 | Wampler |
| 4,918,383 A | 4/1990 | Huff et al. |
| 4,931,036 A | 6/1990 | Kanai et al. |
| 4,939,405 A | 7/1990 | Okuyama et al. |
| 4,955,856 A | 9/1990 | Phillips |
| 4,995,857 A | 2/1991 | Arnold |
| 5,147,388 A | 9/1992 | Yamazaki |
| 5,263,978 A | 11/1993 | Kaufmann et al. |
| 5,275,580 A | 1/1994 | Yamazaki |
| 5,300,111 A | 4/1994 | Panton et al. |
| 5,360,445 A | 11/1994 | Goldowsky |
| 5,370,509 A | 12/1994 | Golding et al. |
| 5,525,041 A | 6/1996 | Deak |
| 5,588,812 A | 12/1996 | Taylor et al. |
| 5,840,070 A | 11/1998 | Wampler |
| 5,924,975 A | 7/1999 | Goldowsky |
| 5,982,801 A | 11/1999 | Deak |
| 6,030,336 A | 2/2000 | Franchi |
| 6,058,593 A | 5/2000 | Siess |
| 6,079,214 A | 6/2000 | Bishop |
| 6,083,260 A | 7/2000 | Aboul-Hosn |
| 6,116,862 A | 9/2000 | Rau et al. |
| 6,123,725 A | 9/2000 | Aboul-Hosn |
| 6,176,822 B1 | 1/2001 | Nix et al. |
| 6,176,848 B1 | 1/2001 | Rau et al. |
| 6,346,071 B1 | 2/2002 | Mussivand |
| 6,361,284 B2 | 3/2002 | Drevet |
| 6,395,026 B1 | 5/2002 | Aboul-Hosn et al. |
| 6,530,876 B1 | 3/2003 | Spence |
| 6,532,964 B2 | 3/2003 | Aboul-Hosn et al. |
| 6,658,740 B2 | 12/2003 | Habben |
| 6,659,740 B2 | 12/2003 | Drevet |
| 6,672,847 B2 | 1/2004 | Dooley |
| 6,723,039 B2 | 4/2004 | French et al. |
| 6,726,648 B2 | 4/2004 | Kaplon et al. |
| 6,732,501 B2 | 5/2004 | Yu et al. |
| 6,811,381 B2 | 11/2004 | Dooley |
| 6,848,001 B1 | 1/2005 | Sakamoto et al. |
| 6,935,344 B1 | 8/2005 | Aboul-Hosn et al. |
| 6,976,996 B1 | 12/2005 | Aboul-Hosn |
| 7,011,620 B1 | 3/2006 | Siess |
| 7,027,875 B2 | 4/2006 | Siess et al. |
| 7,182,727 B2 | 2/2007 | Aboul-Hosn |
| 7,323,961 B2 | 1/2008 | Drevet |
| 7,520,850 B2 | 4/2009 | Brockway |
| 7,696,634 B2 | 4/2010 | Filardo |
| 7,736,296 B2 | 6/2010 | Siess et al. |
| 7,839,007 B2 | 11/2010 | Filardo |
| 7,863,768 B2 | 1/2011 | Filardo |
| 7,889,877 B2 | 2/2011 | Lutz |
| 7,988,728 B2 | 8/2011 | Ayre |
| 8,012,079 B2 | 9/2011 | Delgado, III |
| 8,152,845 B2 | 4/2012 | Bourque |
| 8,157,720 B2 | 4/2012 | Marseille et al. |
| 8,167,593 B2 | 5/2012 | Gohean et al. |
| 8,333,686 B2 | 12/2012 | Marseille et al. |
| 8,343,029 B2 | 1/2013 | Farnan et al. |
| 8,366,401 B2 | 2/2013 | Pate et al. |
| 8,394,009 B2 | 3/2013 | Bolyard et al. |
| 8,394,010 B2 | 3/2013 | Farnan |
| 8,432,057 B2 | 4/2013 | Filardo |
| 8,449,444 B2 | 5/2013 | Poirier |
| 8,465,410 B2 | 6/2013 | Marseille et al. |
| 8,512,012 B2 | 8/2013 | Akdis et al. |
| 8,550,975 B2 | 10/2013 | Foster |
| 8,556,795 B2 | 10/2013 | Bolyard et al. |
| 8,562,508 B2 | 10/2013 | Dague et al. |
| 8,585,571 B2 | 11/2013 | Bachman et al. |
| 8,597,350 B2 | 12/2013 | Rudser et al. |
| 8,610,304 B2 | 12/2013 | Filardo |
| 8,714,944 B2 | 5/2014 | Drevet |
| 8,753,256 B2 | 6/2014 | Bolyard et al. |
| 8,784,291 B2 | 7/2014 | Farnan et al. |
| 8,821,366 B2 | 9/2014 | Farnan et al. |
| 8,821,527 B2 | 9/2014 | Farnan et al. |
| 8,827,888 B2 | 9/2014 | Bolyard et al. |
| 8,834,136 B2 | 9/2014 | Drevet |
| 8,852,072 B2 | 10/2014 | LaRose et al. |
| 8,870,739 B2 | 10/2014 | LaRose et al. |
| 8,956,275 B2 | 2/2015 | Bolyard et al. |
| 8,976,546 B2 | 3/2015 | Wang et al. |
| 9,022,916 B2 | 5/2015 | Farnan et al. |
| 9,080,564 B2 | 7/2015 | Drevet |
| 9,089,635 B2 | 7/2015 | Reichenbach et al. |
| 9,144,669 B2 | 9/2015 | Wieselthaler |
| 9,145,875 B2 | 9/2015 | Filardo |
| 9,173,984 B2 | 11/2015 | LaRose et al. |
| 9,211,367 B2 | 12/2015 | Farnan et al. |
| 9,308,304 B2 | 4/2016 | Peters et al. |
| 9,446,180 B2 | 9/2016 | Vadala, Jr. et al. |
| 9,526,819 B2 | 12/2016 | Chen |
| 9,572,915 B2 | 2/2017 | Heuring et al. |
| 9,579,437 B2 | 2/2017 | LaRose et al. |
| 9,616,158 B2 | 4/2017 | Yaghdjian |
| 9,694,123 B2 | 7/2017 | Bourque et al. |
| 9,731,057 B2 | 8/2017 | Garrigue |
| 9,744,279 B2 | 8/2017 | Tamez et al. |
| 9,786,150 B2 | 10/2017 | Kimball et al. |
| 9,861,728 B2 | 1/2018 | Farnan et al. |
| 9,956,333 B2 | 5/2018 | LaRose et al. |
| 9,968,720 B2 | 5/2018 | Botterbusch et al. |
| 10,166,319 B2 | 1/2019 | Botterbusch et al. |
| 10,188,779 B1 | 1/2019 | Polverelli et al. |
| 10,398,821 B2 | 9/2019 | Botterbusch et al. |
| 10,799,625 B2 | 10/2020 | Scheffler et al. |
| 10,933,181 B2 | 3/2021 | Le Duc De Lillers et al. |
| 11,097,091 B2 | 8/2021 | Botterbusch et al. |
| 11,191,946 B2 | 12/2021 | Snyder et al. |
| 11,298,522 B2 | 4/2022 | Botterbusch et al. |
| 11,446,480 B2 | 9/2022 | Polverelli et al. |
| 11,512,689 B2 | 11/2022 | Drevet et al. |
| 11,623,077 B2 | 4/2023 | Le Duc De Lillers et al. |
| 11,712,554 B2 | 8/2023 | Botterbusch et al. |
| 2001/0001278 A1 | 5/2001 | Drevet |
| 2002/0095210 A1 | 7/2002 | Finnegan et al. |
| 2002/0146333 A1 | 10/2002 | Drevet |
| 2002/0165426 A1 | 11/2002 | Sporer et al. |
| 2003/0002325 A1 | 1/2003 | Alvandpour et al. |
| 2004/0002624 A1 | 1/2004 | Yu et al. |
| 2004/0068220 A1 | 4/2004 | Couvillon et al. |
| 2005/0031474 A1 | 2/2005 | Zackl |
| 2005/0261543 A1 | 11/2005 | Abe et al. |
| 2005/0288543 A1 | 12/2005 | Stenberg et al. |
| 2006/0014999 A1 | 1/2006 | Heilman et al. |
| 2006/0155158 A1 | 7/2006 | Aboul-Hosn |
| 2006/0288543 A1 | 12/2006 | Lubera et al. |
| 2007/0299297 A1 | 12/2007 | Jarvik |
| 2008/0232987 A1 | 9/2008 | Drevet |
| 2009/0082778 A1 | 3/2009 | Beane et al. |
| 2010/0234941 A1 | 9/2010 | Finocchiaro et al. |
| 2010/0241223 A1 | 9/2010 | Lee et al. |
| 2011/0124950 A1 | 5/2011 | Foster |
| 2011/0176945 A1 | 7/2011 | Drevet |
| 2011/0176946 A1 | 7/2011 | Drevet |
| 2011/0238172 A1 | 9/2011 | Akdis |
| 2011/0260449 A1 | 10/2011 | Pokorney |
| 2012/0089225 A1 | 4/2012 | Akkerman et al. |
| 2012/0177506 A1 | 7/2012 | Örter |
| 2012/0220816 A1 | 8/2012 | Peters et al. |
| 2012/0226350 A1 | 9/2012 | Rudser et al. |
| 2012/0323318 A1 | 12/2012 | Yusuf et al. |

(56) References Cited

U.S. PATENT DOCUMENTS

| | | |
|---|---|---|
| 2013/0042753 A1 | 2/2013 | Becker et al. |
| 2013/0078122 A1 | 3/2013 | Drevet |
| 2013/0178694 A1 | 7/2013 | Jeffery et al. |
| 2013/0267779 A1 | 10/2013 | Woolford et al. |
| 2013/0314047 A1 | 11/2013 | Eagle et al. |
| 2014/0023533 A1 | 1/2014 | Ishii et al. |
| 2014/0067057 A1 | 3/2014 | Callaway et al. |
| 2014/0187852 A1 | 7/2014 | Peters et al. |
| 2014/0207232 A1 | 7/2014 | Garrigue |
| 2014/0275723 A1 | 9/2014 | Fritz, IV et al. |
| 2014/0277423 A1 | 9/2014 | Alkhatib et al. |
| 2014/0303426 A1 | 10/2014 | Kerkhoffs et al. |
| 2014/0316426 A1 | 10/2014 | Gollner et al. |
| 2015/0167659 A1 | 6/2015 | Sauer |
| 2015/0273124 A1 | 10/2015 | Callaway et al. |
| 2015/0330383 A1 | 11/2015 | Letailleur et al. |
| 2016/0038664 A1 | 2/2016 | Callaway et al. |
| 2016/0051738 A1 | 2/2016 | Callaway et al. |
| 2016/0235899 A1 | 8/2016 | Yu et al. |
| 2016/0243294 A1 | 8/2016 | Peters et al. |
| 2017/0000934 A1 | 1/2017 | Miyakoshi |
| 2017/0012491 A1 | 1/2017 | Schob et al. |
| 2017/0266358 A1 | 9/2017 | Aber |
| 2017/0290966 A1 | 10/2017 | Botterbusch et al. |
| 2017/0290967 A1 | 10/2017 | Botterbusch et al. |
| 2017/0296723 A1 | 10/2017 | Garrigue |
| 2018/0038364 A1 | 2/2018 | Dumas et al. |
| 2018/0050143 A1 | 2/2018 | Nguyen et al. |
| 2018/0256798 A1 | 9/2018 | Botterbusch et al. |
| 2018/0369469 A1 | 12/2018 | Le Duc De Lillers et al. |
| 2019/0125949 A1 | 5/2019 | Botterbusch et al. |
| 2019/0268332 A1 | 8/2019 | Wang |
| 2019/0381227 A1 | 12/2019 | Botterbusch et al. |
| 2020/0368417 A1 | 11/2020 | Polverelli et al. |
| 2021/0085845 A1 | 3/2021 | West |
| 2021/0170160 A1 | 6/2021 | Le Duc De Lillers et al. |
| 2021/0172429 A1 | 6/2021 | Drevet et al. |
| 2021/0275797 A1* | 9/2021 | Snyder ............... A61M 60/818 |
| 2021/0379353 A1* | 12/2021 | Botterbusch .......... A61M 60/88 |
| 2022/0016412 A1 | 1/2022 | Bourquin et al. |

FOREIGN PATENT DOCUMENTS

| | | | |
|---|---|---|---|
| CA | 2712945 A1 | | 7/2009 |
| CN | 1257006 A | | 6/2000 |
| CN | 1355715 A | | 6/2002 |
| CN | 1714759 A | | 1/2006 |
| CN | 101472627 A | | 7/2009 |
| CN | 101878049 A | | 11/2010 |
| CN | 102112744 A | | 6/2011 |
| CN | 102284092 A | | 12/2011 |
| CN | 106421939 A | | 2/2017 |
| CN | 106489026 A | | 3/2017 |
| CN | 107635602 A | | 1/2018 |
| CN | 108514661 A | | 9/2018 |
| CN | 114367029 A | * | 4/2022 |
| CN | 114470512 A | | 5/2022 |
| EP | 0412856 A1 | | 2/1991 |
| EP | 0415949 A1 | | 3/1991 |
| EP | 0412856 B1 | | 1/1994 |
| EP | 0445782 B1 | | 8/1994 |
| EP | 0925081 B1 | | 12/2003 |
| EP | 0961621 B1 | | 7/2004 |
| EP | 1551500 A2 | | 7/2005 |
| EP | 1233797 B1 | | 7/2006 |
| EP | 1337288 B1 | | 3/2008 |
| EP | 1981585 A2 | | 10/2008 |
| EP | 1644639 B1 | | 2/2009 |
| EP | 2152339 A1 | | 2/2010 |
| EP | 2249746 A1 | | 11/2010 |
| EP | 2310067 A1 | | 4/2011 |
| EP | 2600918 A1 | | 6/2013 |
| EP | 2517739 B1 | | 12/2013 |
| EP | 2704761 A1 | | 3/2014 |
| EP | 2310067 B1 | | 4/2014 |
| EP | 2753389 A1 | | 7/2014 |
| EP | 2152339 B1 | | 5/2015 |
| EP | 2891502 A1 | | 7/2015 |
| EP | 2704761 B1 | | 9/2015 |
| EP | 2736552 B1 | | 9/2015 |
| EP | 2891502 B1 | | 7/2016 |
| EP | 2164542 B1 | | 8/2016 |
| EP | 2856190 B1 | | 9/2016 |
| EP | 3141269 A1 | | 3/2017 |
| EP | 3145558 A2 | | 3/2017 |
| ES | 2587072 A1 | | 10/2016 |
| FR | 355700 A | | 11/1905 |
| FR | 2650862 B1 | | 11/1991 |
| FR | 2744769 A1 | | 8/1997 |
| FR | 2744769 B1 | | 2/1999 |
| FR | 2861910 B1 | | 1/2006 |
| FR | 2905147 A1 | | 2/2008 |
| FR | 3032917 A1 | | 8/2016 |
| GB | 662047 A | | 11/1951 |
| JP | 2011509801 A | | 3/2011 |
| KR | 20130068373 A | | 6/2013 |
| WO | WO-8910763 A1 | | 11/1989 |
| WO | WO-9008260 A1 | | 7/1990 |
| WO | WO-9729282 A1 | | 8/1997 |
| WO | WO-9959652 A1 | | 11/1999 |
| WO | WO-0037126 A1 | | 6/2000 |
| WO | WO-0074747 A1 | | 12/2000 |
| WO | WO-2007053881 A1 | | 5/2007 |
| WO | WO-2011056823 A2 | | 5/2011 |
| WO | WO-2016179262 A1 | | 11/2016 |
| WO | WO-2017087717 A1 | | 5/2017 |
| WO | WO-2017087785 A1 | | 5/2017 |
| WO | WO-2019019206 A1 | | 1/2019 |
| WO | WO-2019092175 A1 | | 5/2019 |
| WO | WO-2019154804 A1 | | 8/2019 |
| WO | WO-2020115607 A2 | | 6/2020 |

OTHER PUBLICATIONS

Ando, et al., Left ventricular decompression through a patent foramen ovale in a patient with hypertrophic cardiomyopathy: A case report, Cardiovascular Ultrasound, 2: 1-7 (2004).

Bozkurt, et al., Improving Arterial Pulsatility by Feedback Control of a Continuous Flow Left Ventricular Assist Device via in silico Modeling, International Journal of Artificial Organs, 37(10):773-785 (2014).

Castellanos, et al., Generations of Left Ventricular Assist Devices: The HeartMate Family, Dept. of Bioengineering. Florida Gulf Coast University, BME 3100C, pp. 1-6. (No date available).

Crow, et al., Gastrointestinal Bleeding Rates in Recipients of Nonpulsatile and Pulsatile Left Ventricular Assist Devices, The Journal of Thoracic and Cardiovascular Surgery, 137(1):208-215 (2009).

Extended European Search Report dated Aug. 25, 2021 in EP Patent Application Serial No. 21168340.4.

Fatullayev, et al., Continuous-Flow Left Ventricular Assist Device Thrombosis: A Danger Foreseen is a Danger Avoided, Medical Science Monitor Basic Research, 21:141-144 (2015).

Feier, et al., A Novel, Valveless Ventricular Assist Device: The Fish Tail Pump. First Experimental in Vivo Studies, Artificial Organs, (26)12:1026-1031 (2002).

Fliess, et al., Flatness and Defect of Nonlinear Systems: Introductory Theory and Examples, International Journal of Control, 61(6):1327-1361 (1995).

Fraser et al., A Quantitative Comparison of Mechanical Blood Damage Parameters in Rotary Ventricular Assist Devices: Shear Stress, Exposure Time and Hemolysis Index, Journal of Biomechanical Engineering, 134(8):018002-1 to 018002-11 (2012).

Harris, et al., Ventricular Assist Devices, Continuing Education in Anesthesia, Critical Care & Pain, 12(3):145-151 (2012).

International Search Report & Written Opinion dated Mar. 4, 2019 in Int'l PCT Patent Appl. No. PCT/IB2018/059199, 13 pages.

International Search Report & Written Opinion dated May 14, 2021 in Int'l PCT Patent Appl. Serial No. PCT/IB2021/051879.

(56) References Cited

OTHER PUBLICATIONS

International Search Report & Written Opinion dated Jun. 28, 2017 in Int'l PCT Patent Application Serial No. PCT/IB2017/052068.
International Search Report & Written Opinion dated Jul. 15, 2020 in Int'l PCT Patent Appl. Serial No. PCT/IB2019/060144.
International Search Report & Written Opinion dated Aug. 22, 2017 in Int'l PCT Patent Application Serial No. PCT/IB2017/052069.
International Search Report and Written Opinion dated Apr. 16, 2019 in Int'l PCT Patent Appl. Serial No. PCT/EP2018/080749 (English Translation of ISR only).
International Search Report and Written Opinion dated Jun. 25, 2020 in International PCT Patent Application Serial No. PCT/IB2020/052337.
International Search Report and Written Opinion dated Aug. 3, 2018 in Int'l PCT Patent Appl. Serial No. PCT/IB2018/052215.
Ising, M., RPM and Flow Modulation for a Continuous Flow Left Ventricular Assist Device to Increase Vascular Pulsatility: A Computer Simulation, Mock Circulation, and In-Vivo Animal Study, University of Louisville, Think IR: The University of Louisville's Institutional Repository, Electronic Theses and Dissertations (Jul. 2011).
Islam et al., Left Ventricular Assist Devices and Gastrointestinal Bleeding: A Narrative Review of Case Reports and Case Series, Clinical Cardiology, 36(4):190-200 (2013).
Jorde, et al., Identification and Management of Pump Thrombus in the HeartWare Left Ventricular Assist Device System, JACC: Heart Failure, 3(11):849-856 (2015).
Latham, et al., Parameter Estimation and a Series of Nonlinear Observers for the System Dynamics of a Linear Vapor Compressor, IEEE Transactions on Industrial Electronics, 63(11):6736-6744 (2016).
Leverett, et al., Red Blood Cell Damage by Shear Stress, Biophysical Journal, 12(3):257-273 (1972).
Malehsa, et al., Acquired von Willebrand Syndrome After Exchange of the HeartMate XVE to the HeartMate II Ventricular Assist Device, European Journal of Cardio-Thoracic Surgery, 35(6):1091-1093 (2009).
Mancini, et al., Left Ventricular Assist Devices, A Rapidly Evolving Alternative to Transplant, Journal of the American College of Cardiology, 653:2542-2555 (2015).
Mboup, et al., Numerical Differentiation With Annihilators in Noisy Environment, Numerical Algorithms, 50(4):439-467 (2009).
Menhour, et al., An Efficient Model-Free Setting for Longitudinal and Lateral Vehicle Control: Validation Through the Interconnected Pro-SiVIC/RTMaps Prototyping Platform, IEEE Transactions on Intelligent Transportation Systems, 19(2):461-475 (2018).
Mercorelli, P., A Motion-Sensorless Control for Intake Valves in Combustion Engines, IEEE Transactions on Industrial Electronics, 64(4):3402-3412 (2017).
Mercorelli, P., An Adaptive and Optimized Switching Observer for Sensorless Control of an Electromagnetic Valve Actuator in Camless Internal Combustion Engines, Asian Journal of Control, 16(4):959-973 (2014).
Mohite, et al., Does CircuLite Synergy Assist Device as Partial Ventricular Support have a Place in Modern Management of Advanced Heart Failure?, Expert Rev. Med. Devices, published online Dec. 2, 2014 (pp. 1-12).
Najjar, et al., An Analysis of Pump Thrombus Events in Patients in HeartWare Advance Bridge to Transplant and Continued Access Protocol Trial, The Journal of Heart and Lung Transplantation, 33(1):23-34 (2014).
Pagani, Francis D., Md, Phd, Department of Cardiac Surgery, University of Michigan, "Technology 101: Review of Current Technologies, Types of Flow, Pump Parameters," American Association for Thoracic Surgery, Annual Meeting (2014), Cardiothoracic Transplant and Mechanical Circulatory Support of Heart and Lung Failure.
Perschall, et al., The Progressive Wave Pump: Numerical Multiphysics Investigation of a Novel Pump Concept With Potential to Ventricular Assist Device Application, Artificial Organs, 35(9):E179-E190 (2012).
Rahman, et al., Position Estimation in Solenoid Actuators, IEEE Transactions on Industry Applications, 32(3):552-559 (1996).
Rigatos, G., Differential Flatness Theory ad Flatness-Based Control, in Nonlinear Control and Filtering Using Differential Flatness Approaches, 25(2):47-101 (2015).
Wang, et al., Rotary Blood Pump Control Strategy for Preventing Left Ventricular Suction, ASAIO Journal, 61(1):21-30(2015).
Wang., Quadrotor Analysis and Model Free Control with Comparisons, Universite Paris Sud—Paris XI, (2013).
Weidemann, Daniel., Thesis entitled, Permanent Magnet Reluctance Actuators for Vibration Testing, Completed at the Institute of Applied Mechanics, Technische Universitat Munchen, Apr. 2013.
Yuan, et al., The Spectrum of Complications Following Left Ventricular Assist Device Placement, Journal of Cardiac Surgery, 27:630-638 (2012).
Zhang, et al., Study on Self-Sensor of Linear Moving Magnet Compressor's Piston Stroke, IEEE Sensors Journal, 9(2):154-158 (2009).
International Search Report & Written Opinion dated Oct. 9, 2023 in Int'l PCT Patent Appl. Serial No. PCT/IB2023/054203.
Invitation to Pay Additional Fees and Partial Search Report dated Feb. 7, 2024 in Int'l PCT Patent Appl. Serial No. PCT/IB2023/061509.
International Search Report & Written Opinion dated Apr. 2, 2024 in Int'l PCT Patent Appl. Serial No. PCT/IB2023/061509.

* cited by examiner

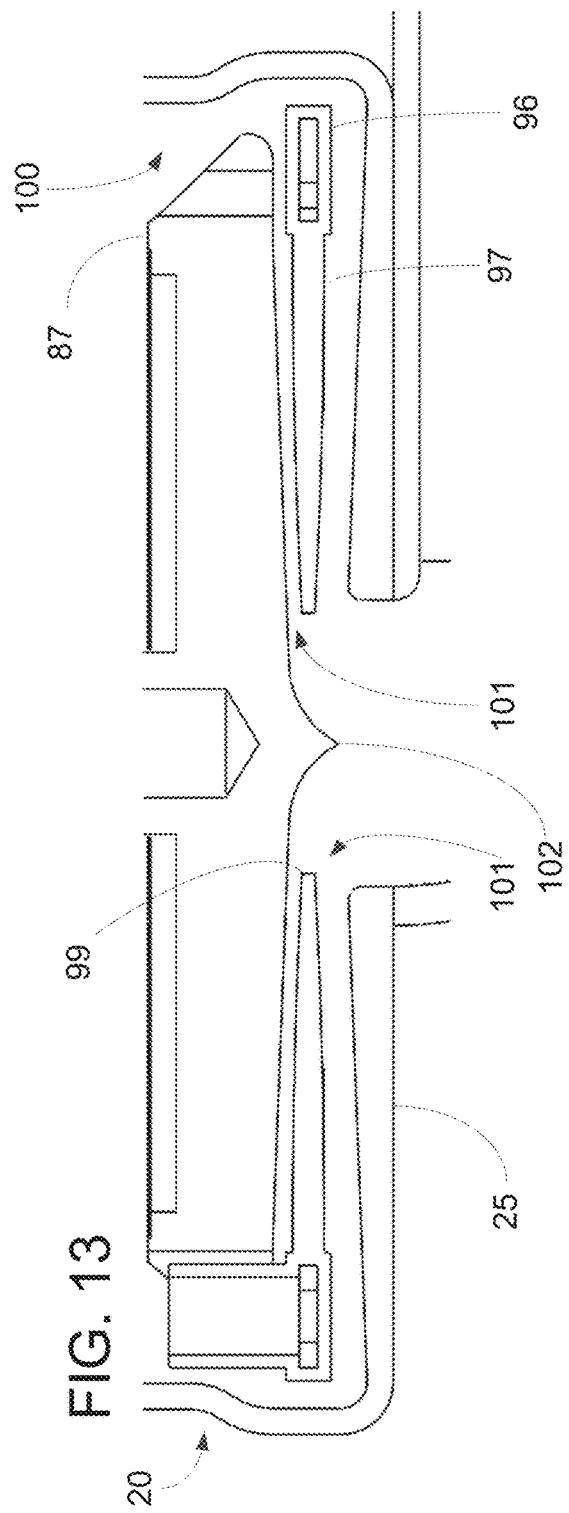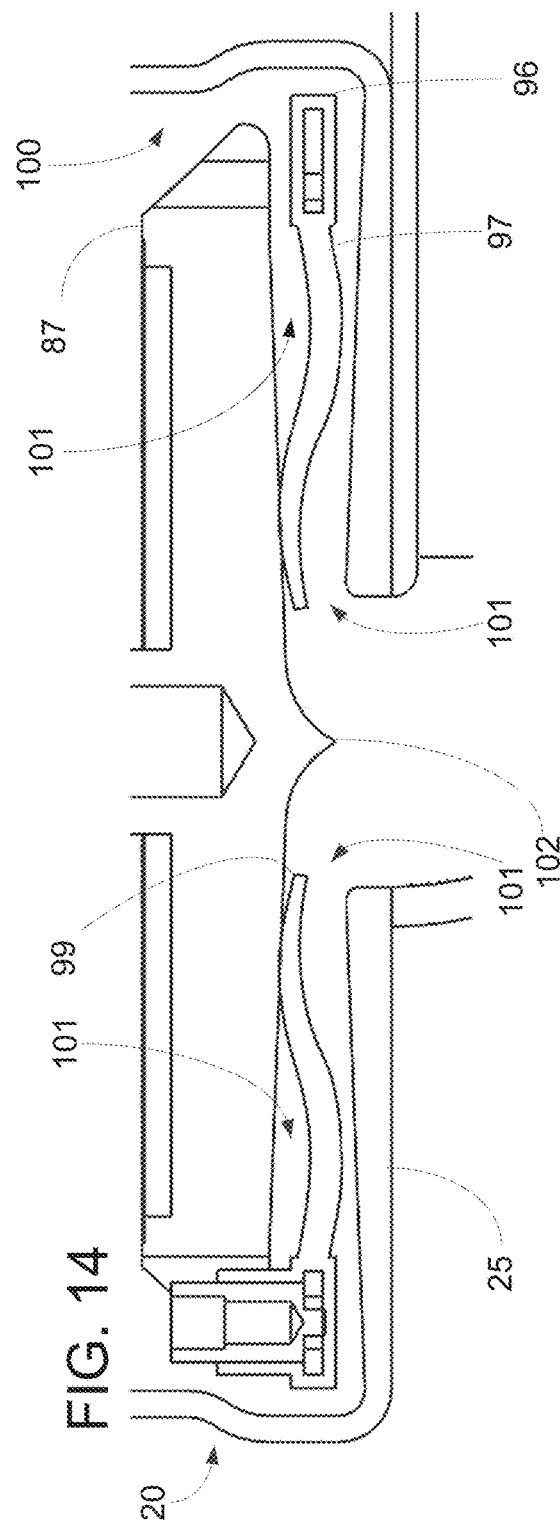

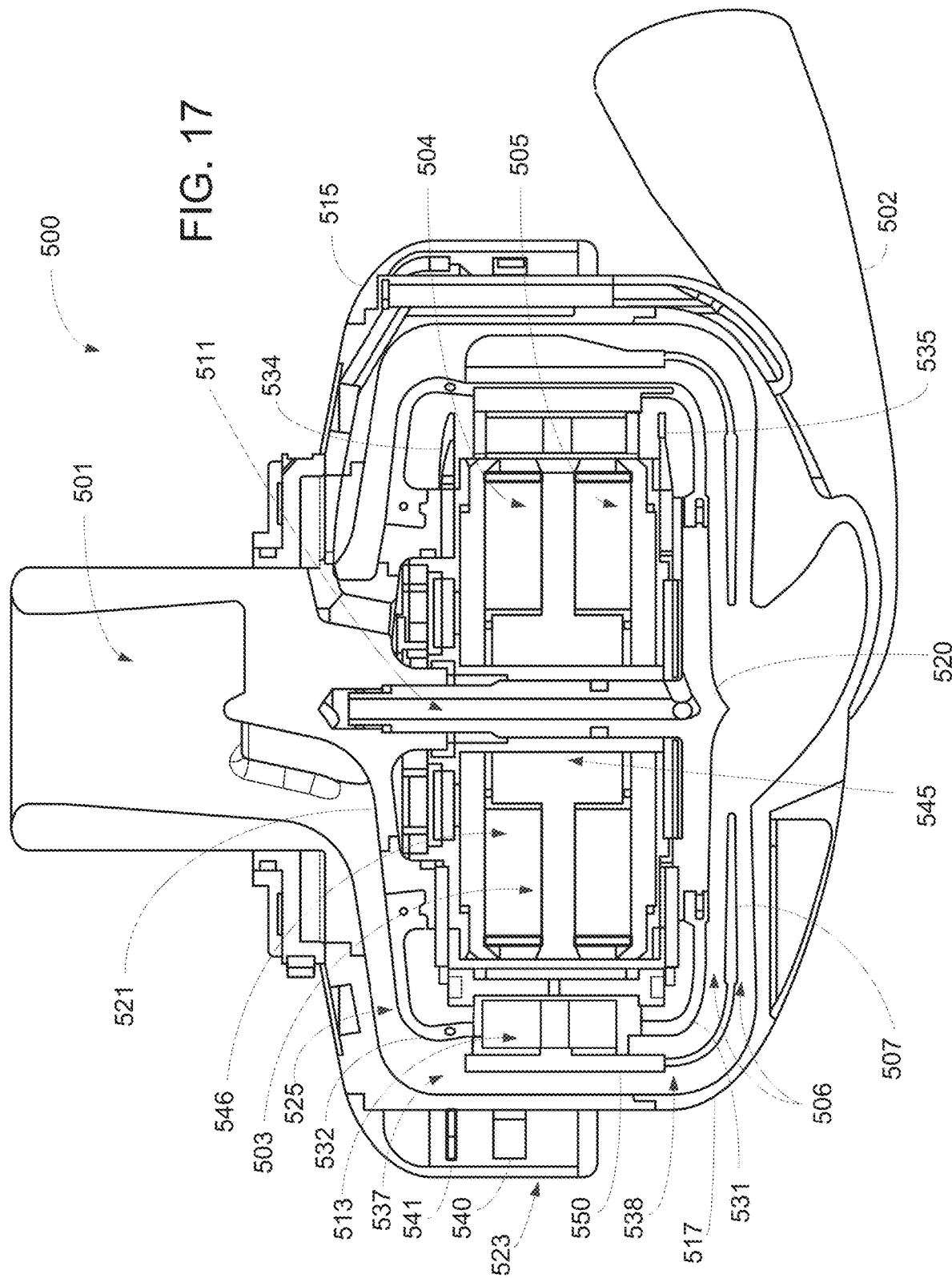

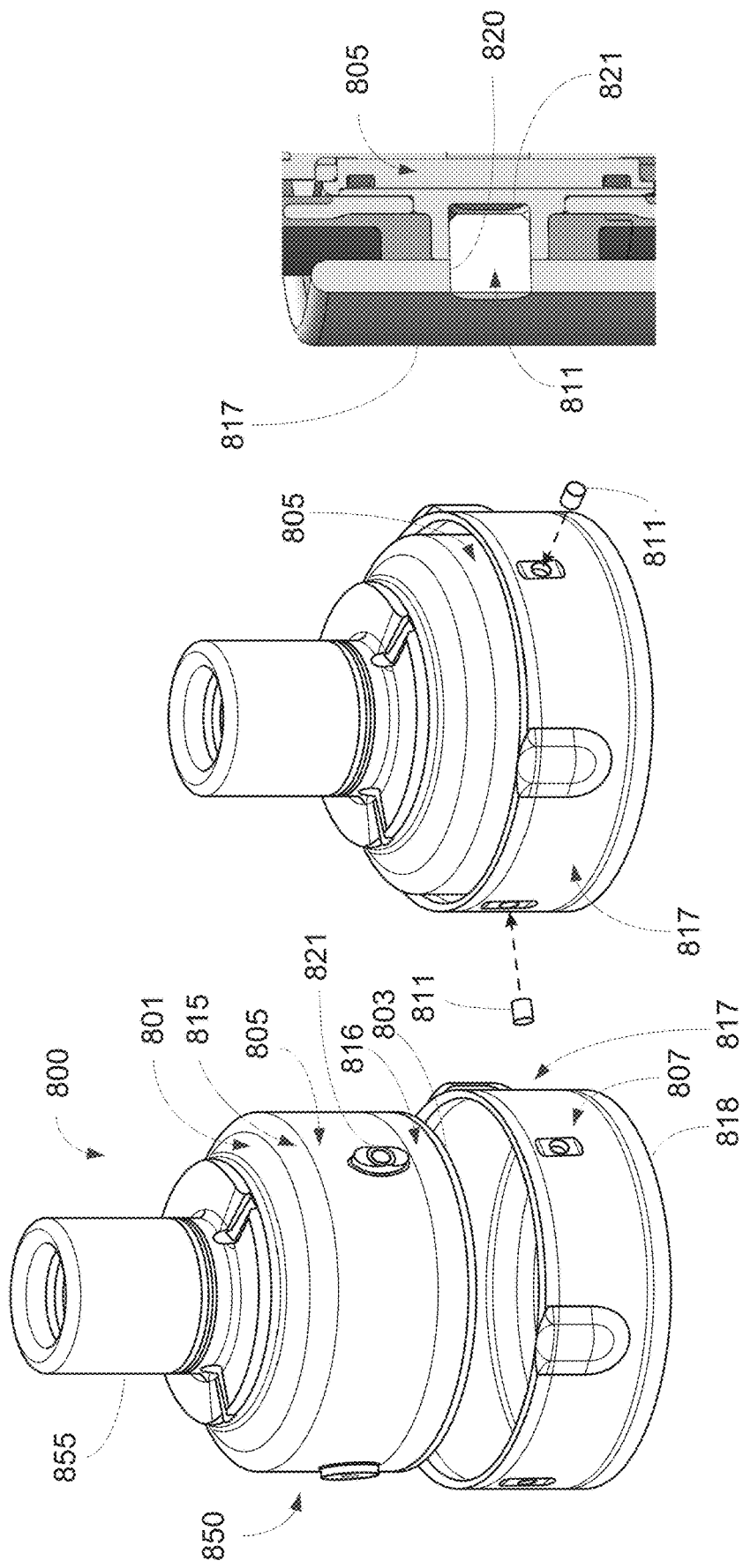

BLOOD PUMPS HAVING AN ENCAPSULATED ACTUATOR

CROSS-REFERENCE TO RELATED APPLICATION

This application claims priority to U.S. Provisional Application Ser. No. 63/363,635, filed Apr. 26, 2022, and EP Patent Application Serial No. 22315090.5, filed Apr. 26, 2022, the entire contents of each of which are incorporated herein by reference.

FIELD OF THE INVENTION

The present invention relates generally to blood pumps. For example, systems and methods are provided herein including an implantable heart pump with improved hydraulic performance designed to reduce hemolysis and platelet activation, for example, by encapsulating an actuator assembly.

BACKGROUND

The human heart is comprised of four major chambers with two ventricles and two atria. Generally, the right-side heart receives oxygen-poor blood from the body into the right atrium and pumps it via the right ventricle to the lungs. The left-side heart receives oxygen-rich blood from the lungs into the left atrium and pumps it via the left ventricle to the aorta for distribution throughout the body. Due to any of a number of illnesses, including coronary artery disease, high blood pressure (hypertension), valvular regurgitation and calcification, damage to the heart muscle as a result of infarction or ischemia, myocarditis, congenital heart defects, abnormal heart rhythms or various infectious diseases, the left ventricle may be rendered less effective and thus unable to pump oxygenated blood throughout the body.

The American Heart Association estimates that about 6 million people in the United States suffer from some form of heart failure. Heart failure is generally categorized into four different stages with the most severe being end stage heart failure. Patients with end stage heart failure may experience heart failure symptoms at rest in spite of medical treatment. Patients at this stage experience heart failure, characterized by decreasing ejection fraction. In patients with systolic heart failure, the walls of the ventricle, which are typically thick in a healthy patient, become thin and weak. Consequently, during systole a reduced volume of oxygenated blood is ejected into circulation, a situation that continues in a downward spiral until death. A patient diagnosed with end stage heart failure has a one-year mortality rate of approximately 50%.

For patients that have reached end stage heart failure, treatment options are limited. In addition to continued use of drug therapy commonly prescribed during earlier stages of heart failure, the treatment options are cardiac transplantation and implantation of a mechanical assist device. While a cardiac transplant may significantly prolong the patient's life, there are only 3,000-3,500 transplants performed in the United States, due to a lack of available donor organs. Thus, patients frequently remain on the transplant waitlist for several months to years awaiting a suitable donor heart. Presently, one alternative to a cardiac transplant is a circulatory assist device. While in recent years circulatory assist devices have improved in design, typically such implants will prolong a patient's life by a few years at most, and include a number of co-morbidities.

One type of circulatory assist device available for patients with end stage heart failure is a left ventricular assist device (LVAD). The LVAD is a surgically implanted pump that draws oxygenated blood from the left ventricle and pumps it directly to the aorta, thereby off-loading (reducing) the pumping work of the left ventricle. LVADs typically are used as a "bridge-to-transplant therapy", "bridge-to-recovery", or "destination therapy." When used for bridge-to-transplant therapy, the LVAD is used to prolong the life of a patient who is waiting for a heart transplant. In bridge-to-recovery therapy, the patient's native heart recovers sufficient function during the period of mechanical circulatory support, the device can be removed from the patient or "de-commissioned," partially remaining in situ. When a patient is not suitable for a heart transplant, the LVAD may be used as a destination therapy to prolong the life, or improve the quality of life, of the patient, but generally such prolongation is for only a couple years.

Generally, a LVAD includes an inlet cannula, a pump, and an outlet cannula, and is coupled to an extracorporeal battery and control unit. The inlet cannula is typically directly connected to the left ventricle, e.g. at the apex, and delivers blood from the left ventricle to the pump. The outlet cannula is typically connected to the aorta distal to the aortic valve and delivers blood from the pump to the aorta. Typically, the outlet cannula of the pump is extended using a hose-type structure, such as a Dacron graft, to reach a proper delivery location on the aorta. Early LVAD designs were of the reciprocating type but more recently rotary and centrifugal pumps have been used.

U.S. Pat. No. 4,277,706 to Isaacson, entitled "Actuator for Heart Pump," describes a LVAD having a reciprocating pump. The pump described in the Isaacson patent includes a housing having an inlet and an outlet, a cavity in the interior of the pump connected to the inlet and the outlet, a flexible diaphragm that extends across the cavity, a plate secured to the diaphragm, and a ball screw that is configured to be reciprocated to drive the plate and connected diaphragm from one end of the cavity to the other end to simulate systole and diastole. The ball screw is actuated by a direct current motor. The Isaacson patent also describes a controller configured to manage the revolutions of the ball screw to control the starting, stopping and reversal of directions to control blood flow in and out of the pump.

Previously-known reciprocating pump LVADs have a number of drawbacks. Such pumps often are bulky, heavy and may require removal of tissue in the chest for implantation. They also require a significant amount of energy to displace the blood by compressing the cavity. Moreover, the pump subjects the blood to significant pressure fluctuations as it passes through the pump as well as high shear forces and risk of hemolysis (e.g., due to valves and/or flow construction). These pressure fluctuations may be exaggerated at higher blood flow rates. Further, depending on the geometry of the pump, areas of little or no flow may result in flow stagnation, which can lead to thrombus formation and potentially fatal medical conditions, such as stroke. Moreover, blood flowing through such a device may become damaged upon contacting moving components. For example, shear-induced damage may contribute to hemolysis. Finally, many positive displacement pumps like the one described in the Isaacson patent are incapable of achieving pulsatility similar to that of the natural heart, e.g., roughly 60 to 100 beats per minute, while maintaining physiological pressure gradients.

LVADs utilizing rotary and centrifugal configurations also are known. For example, U.S. Pat. No. 3,608,088 to Reich, entitled "Implantable Blood Pump," describes a centrifugal pump to assist a failing heart. The Reich patent describes a centrifugal pump having an inlet connected to a rigid cannula that is coupled to the left ventricular cavity and a Dacron graft extending from the pump diffuser to the aorta. A pump includes an impeller that is rotated at high speeds to accelerate blood, and simulated pulsations of the natural heart by changing rotation speeds or introducing a fluid oscillator.

U.S. Pat. No. 5,370,509 to Golding, entitled "Sealless Rotodynamic Pump with Fluid Bearing," describes an axial blood pump capable for use as a heart pump. One embodiment described involves an axial flow blood pump with impeller blades that are aligned with the axes of the blood inlet and blood outlet. U.S. Pat. No. 5,588,812 to Taylor, entitled "Implantable Electrical Axial-Flow Blood Pump," describes an axial flow blood pump similar to that of the Golding patent. The pump described in the Taylor patent has a pump housing that defines a cylindrical blood conduit through which blood is pumped from the inlet to the outlet, and rotor blades that rotate along the axis of the pump to accelerate blood flowing through the blood conduit.

While previously-known LVAD devices have improved, those pump designs are not without problems. Like reciprocating pumps, rotary and centrifugal pumps are often bulky and difficult to implant. Rotary pumps, while mechanically different from positive displacement pumps, also exhibit undesirable characteristics. Like positive displacement pumps, rotary pumps apply significant shear forces to the blood, thereby posing a risk of hemolysis and platelet activation. The very nature of a disk or blade rotating about an axis results in areas of high velocity and low velocity as well as vibration and heat generation. The areas near the leading and trailing edges of the blades and the gap between the blade tip and the housing experience the highest shear forces. In addition, stagnation or low flow rates near the axis of rotation may result in thrombus formation.

While centrifugal pumps may be capable generating pulsatile flow by varying the speed of rotation of the associated disk or blades, this only exacerbates the problems resulting from steep radial velocity profiles and high shear force. In common practice, the output of currently available rotary pumps, measured as flow rate against a given head pressure, is controlled by changing the rotational speed of the pump. Given the mass of the rotating member, the angular velocity of the rotating member, and the resulting inertia, a change in rotational speed may not be instantaneous but instead gradual. Accordingly, while centrifugal pumps may mimic pulsatile flow with speed changes, the resulting pulse may produce physiological pressure changes.

Moreover, rotary pumps typically result in the application of non-physiologic pressure changes on the blood. If the rotational speed of a pump is varied to simulate pulsatile flow or increase flow rate, the rotary pump is less likely to be operated at its optimal operating point, reducing efficiency and increasing energy losses and heat generation.

LVADs may also be configured to increase blood flow to match the demand of the patient. Numerous publications and patents describe methods for adjusting LVAD pump flow to match that demanded by the patient. For example, U.S. Pat. No. 7,520,850 to Brockway, entitled "Feedback control and ventricular assist devices," describes systems and methods for employing pressure feedback to control a ventricular assist device. The system described in the Brockway patent attempts to maintain a constant filling of the ventricle by measuring ventricular pressure and/or ventricular volume. While such systems can achieve flow rates as high as 8 or 9 liters per minute, these flow rates generally are outside of the efficient range of operation for current rotary pumps, which are typically tuned to operate in a range of 4 to 6 liters per minute. Thus, increasing the flow rate in rotary pumps to match patient demanded results in non-optimal pump performance.

Pumps other than of the rotary and positive displacement types are known in the art for displacing fluid. For example, U.S. Pat. Nos. 6,361,284 and 6,659,740, both to Drevet, entitled "Vibrating Membrane Fluid Circulator," describe pumps in which a deformable membrane is vibrated to propel fluid through a pump housing. In these patents, vibratory motion applied to the deformable membrane causes wave-like undulations in the membrane that propel the fluid along a channel. Different flow rates may be achieved by controlling the excitation applied to the membrane.

U.S. Pat. No. 7,323,961 to Drevet, entitled "Electromagnetic Machine with a Deformable Membrane," describes a device in which a membrane is coupled in tension along its outer edge to an electromagnetic device arranged to rotate around the membrane. As the electromagnetic device rotates, the outer edge of the membrane is deflected slightly in a direction normal to the plane of the membrane. These deflections induce a wave-like undulation in the membrane that may be used to move a fluid in contact with the membrane.

U.S. Pat. No. 9,080,564 to Drevet, entitled "Diaphragm Circulator," describes a tensioned deformable membrane in which undulations are created by electromechanically moving a magnetized ring, attached to an outer edge of a deformable membrane, over a coil. Axial displacement of magnetized ring causes undulations of membrane. Like in the '961 patent, the membrane undulations can be controlled by manipulating the magnetic attraction. U.S. Pat. No. 8,714,944 to Drevet, entitled "Diaphragm pump with a Crinkle Diaphragm of Improved Efficiency" and U.S. Pat. No. 8,834,136 to Drevet, entitled "Crinkle Diaphragm Pump" teach similar types of vibrating membrane pumps.

None of the foregoing patents to Drevet describe a vibratory membrane pump suitable for use in a biological setting, or capable of pumping blood over extended periods that present a low risk of flow stagnation leading to thrombus formation.

U.S. Patent Publication Nos. 2017/0290966 and 2017/0290967 to Botterbusch, the entire contents of each of which are incorporated herein by reference, describe implantable cardiovascular blood pumps having a flexible membrane coupled to an electromagnetic actuator assembly that causes wavelike undulations to propagate along the flexible membrane to propel blood through the pump while avoiding thrombus formation, hemolysis and/or platelet activation. The Botterbusch pumps generate hydraulic power—flow and pressure—by translating the linear motion of the electromagnetic actuator, to the flexible membrane, which deforms through its interaction with the blood, translating energy to the blood. The flexible membrane is oriented at a 90° angle to the motion of the linear actuator such that the outer edge of the membrane is the first element to engage the blood. As a result, there is a risk of energy loss at the inlet to the membrane, which affects the hydraulic power generation by the pump.

What is needed is an energy efficient implantable pump having light weight, small size, and fast start and stop response that can operate efficiently and with improved hydraulic performance and minimal blood damage over a wide range of flow rates.

SUMMARY OF THE INVENTION

Provided herein are systems and methods for providing a blood pump for circulatory assistance. The pump system herein may be implanted in a patient's body or be used extracorporeally. The pump system may be used for circulatory assistance, and may, for example, be atrial, ventricular, and/or vascular, for example. The pump system may be an implantable pump system. The pump system may have an undulating membrane capable of producing a wide range of physiological flow rates while applying low shear forces to the blood, thereby reducing hemolysis and platelet activation relative to previously-known systems. The pump system may include a stator assembly, an electromagnetic assembly, a magnetic assembly and a membrane assembly, as well as one or more encapsulator portions to encapsulate the electromagnetic assembly and avoid damaging the blood with the moving components of the pump. The pump system herein may also minimizes areas that may be prone to formation of thrombus within the pump.

In accordance with one aspect of the present invention, a blood pump may include a housing having an inlet and an outlet and designed to be implanted at a patient's heart, a membrane disposed within the housing, an actuator disposed within the housing, the actuator designed to cause the membrane to reciprocate to pump blood, and an encapsulation assembly designed to encapsulate the actuator such that blood does not contact the actuator, the encapsulation assembly disposed within the housing to define a flow channel between the housing and the encapsulation assembly. During operation, blood may enter the inlet, flow between the housing and the encapsulation assembly in the flow channel, and may be propelled across the membrane to the outlet to pump the blood. The pump may further include a magnetic assembly designed to move with respect to the actuator assembly. The magnetic assembly is annular and disposed around the actuator. The blood pump may further include at least one spring coupled to the magnetic assembly and to the actuator. The encapsulation assembly may include the magnetic assembly and the encapsulation assembly also encapsulates at least one spring. The encapsulation assembly isolates the actuator from the blood path which may reduce blood exposure to higher shear conditions in the actuator. The flow channel may be configured to minimize damage to von Willebrand Factor multimers in the blood. The flow channel may be sized and configured to facilitate blood flow towards the outlet and resist blood flow towards the inlet and/or configured to reduce recirculation of the blood. The flow channel may be sized and configured to reduce a risk of shear conditions of the blood in the flow channel.

In accordance with another aspect of the present invention, a blood pump may include a housing having an inlet and an outlet and designed to be implanted at a heart, an actuator disposed within the housing, the actuator comprising an electromagnetic assembly designed to generate a magnetic field, an upper stator coupled to a first side of the actuator, a lower stator coupled to a second side of the actuator, a magnetic assembly including at least one magnet, the magnetic assembly designed to reciprocate responsive to the magnetic field, a first encapsulation portion coupled to the upper stator and the magnetic assembly, a second encapsulation portion coupled to the lower stator and the magnetic assembly, and a flexible membrane coupled to the magnetic assembly and configured to reciprocate responsive to the magnetic assembly. The first encapsulation portion, magnetic assembly and second encapsulation portion may encapsulate the actuator such that, during operation, blood enters the inlet, flows between an inner wall of the housing and the first encapsulation portion, magnetic assembly and second encapsulation portion and is propelled across the flexible membrane to the outlet.

In accordance with another aspect of the present invention, a blood pump may include a housing having an inlet and an outlet, the outlet designed to be in fluid communication with a patient's left ventricle, an actuator assembly comprising a stator assembly and an electromagnetic assembly designed to generate a magnetic field; the actuator assembly disposed within the housing, a magnetic assembly designed to reciprocate responsive to the magnetic field, and an encapsulation assembly coupled to the magnetic assembly and the stator assembly, the encapsulation assembly encapsulate the actuator, and a flexible membrane coupled to the magnetic assembly and designed to reciprocate responsive to the magnetic assembly. During operation, blood may enter the inlet, flow between an inner wall of the housing and the magnetic assembly, stator assembly and the encapsulation assembly and may be propelled across the flexible membrane to the outlet.

In accordance with another aspect of the present invention, a method of pumping blood using a blood pump is provided. The method of pumping blood may include providing a blood pump designed to be positioned at the patient's ventricle and sending an electrical signal to the actuator to excite the electromagnetic assembly to generate the magnetic field. The blood pump may include a housing having an inlet and an outlet, the outlet designed to be in fluid communication with the patient's ventricle, an actuator comprising a stator assembly and an electromagnetic assembly designed to generate a magnetic field, the actuator assembly disposed within the housing, a magnetic assembly configured to reciprocate responsive to the magnetic field, an encapsulation assembly coupled to the magnetic assembly and the stator assembly, the encapsulation assembly designed to encapsulate the actuator, and a flexible membrane coupled to the magnetic assembly and configured to reciprocate responsive to the magnetic assembly. The magnetic field may cause the flexible membrane to reciprocate, thereby propagating a wave along the flexible membrane causing blood to move from the inlet, between an inner wall of the housing and the magnetic assembly, stator assembly and the encapsulation assembly, across the flexible member, and out the outlet.

BRIEF DESCRIPTION OF THE DRAWINGS

FIG. 13 is a cross-sectional view of a lower portion of the blood pump depicting the flow channel and membrane assembly in a resting position.

FIG. 14 is a cross-sectional view of a lower portion of the blood pump depicting the flow channel and membrane assembly with the membrane undulating.

FIG. 16A illustrates blood flow across a planar ring membrane support, whereas FIG. 16C illustrates a blood pump with an integrated portion incorporating a magnetic assembly featuring linear bearing elements and magnets within the housing, whereas

FIG. 17 is a cross-sectional view of a blood pump with an encapsulated actuator assembly.

FIGS. 20A and 20B are perspective views of a membrane assembly and an actuator assembly. FIG. 20C is a cross-sectional view of a portion of an actuator assembly and membrane assembly.

DETAILED DESCRIPTION

The blood pump system of the present invention is particularly well-suited for use as an implantable left ventricular assist device (LVAD), and includes an undulating membrane pump suitable for long-term implantation in a patient having end term heart failure. A blood pump system constructed in accordance with the principles of the present invention includes a blood pump and an extracorporeal battery, controller and programmer. The blood pump system of the present invention may be implantable and/or may be a heart pump (e.g., LVAD). The blood pump includes a housing having an inlet, and outlet, a flexible membrane, and an encapsulated actuator assembly. When configured as an LVAD, the housing includes an inlet cannula that is inserted into a patient's left ventricle near the apex and an outlet cannula that is surgically placed in fluid communication with the patient's aorta. By activating the actuator assembly within the blood pump, the membrane is induced to undulate, thereby causing blood to be drawn into the pump through the inlet cannula and expelled through the outlet cannula into the aorta. Flow rate and pulsatility may be manipulated by changing one or more of the frequency, amplitude and duty cycle of the actuator assembly.

For improved hydraulic performance, the blood pump may include a membrane assembly including a membrane and skirt disposed within the housing to guide blood flow from the inlet of the pump towards the outlet. The skirt may be positioned within the housing such that blood flows across opposing sides of the skirt and towards the undulating membrane upon activation of the pump. For enhanced protection of blood flowing through the blood pump, the actuator assembly may be encapsulated using an encapsulation assembly such that a blood flow channel between the inlet cannula and the outlet cannula of the blood pump is defined by the encapsulation assembly and an interior surface of the housing of the blood pump.

Figure 1:
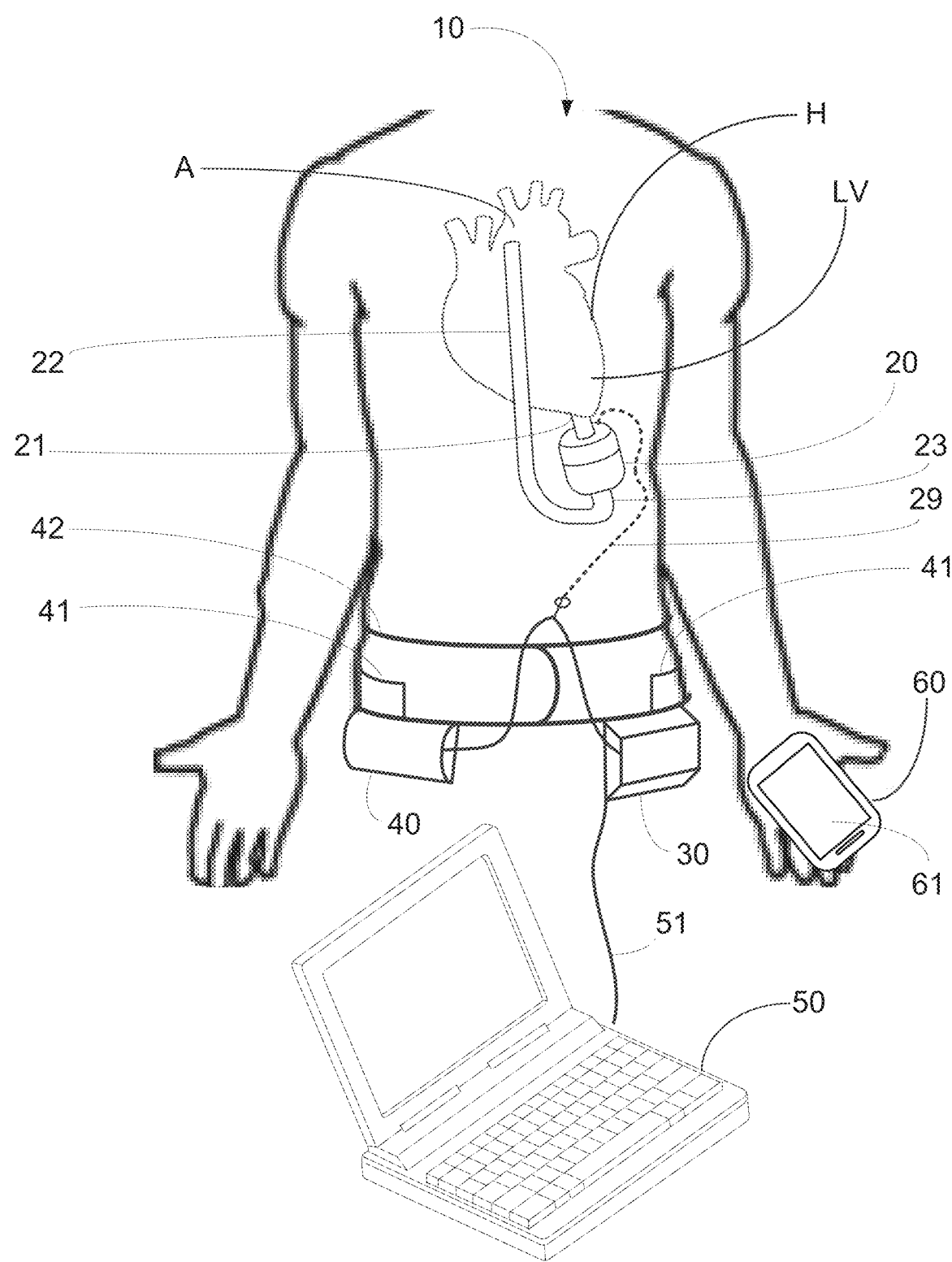
FIG. 1 depicts an exemplary embodiment of the pump system of the present invention comprising a blood pump, controller, battery, programmer and mobile device in accordance with some aspects of the present invention.

Referring now to FIG. 1, pump system 10 constructed in accordance with the principles of the present invention is described. Blood pump system 10 includes pump 20, controller 30, battery 40, programmer 50 and optionally, a software module programmed to run on mobile device 60. Pump 20 is configured to be implanted within a patient's chest so that inlet cannula 21 is coupled to left ventricle LV of heart H. Outlet cannula 22 of pump 20 is configured to be coupled to aorta A. Inlet cannula 21 preferably is coupled to the apex of left ventricle LV, while outlet cannula 22 is coupled to aorta A in the vicinity of the ascending aorta, above the level of the cardiac arteries. Pump 20 may be affixed within the patient's chest using a ring-suture or other conventional technique. Outlet cannula 22, which may comprise a Dacron graft or other synthetic material, is coupled to outlet 23 of implantable pump 20.

Figure 2:
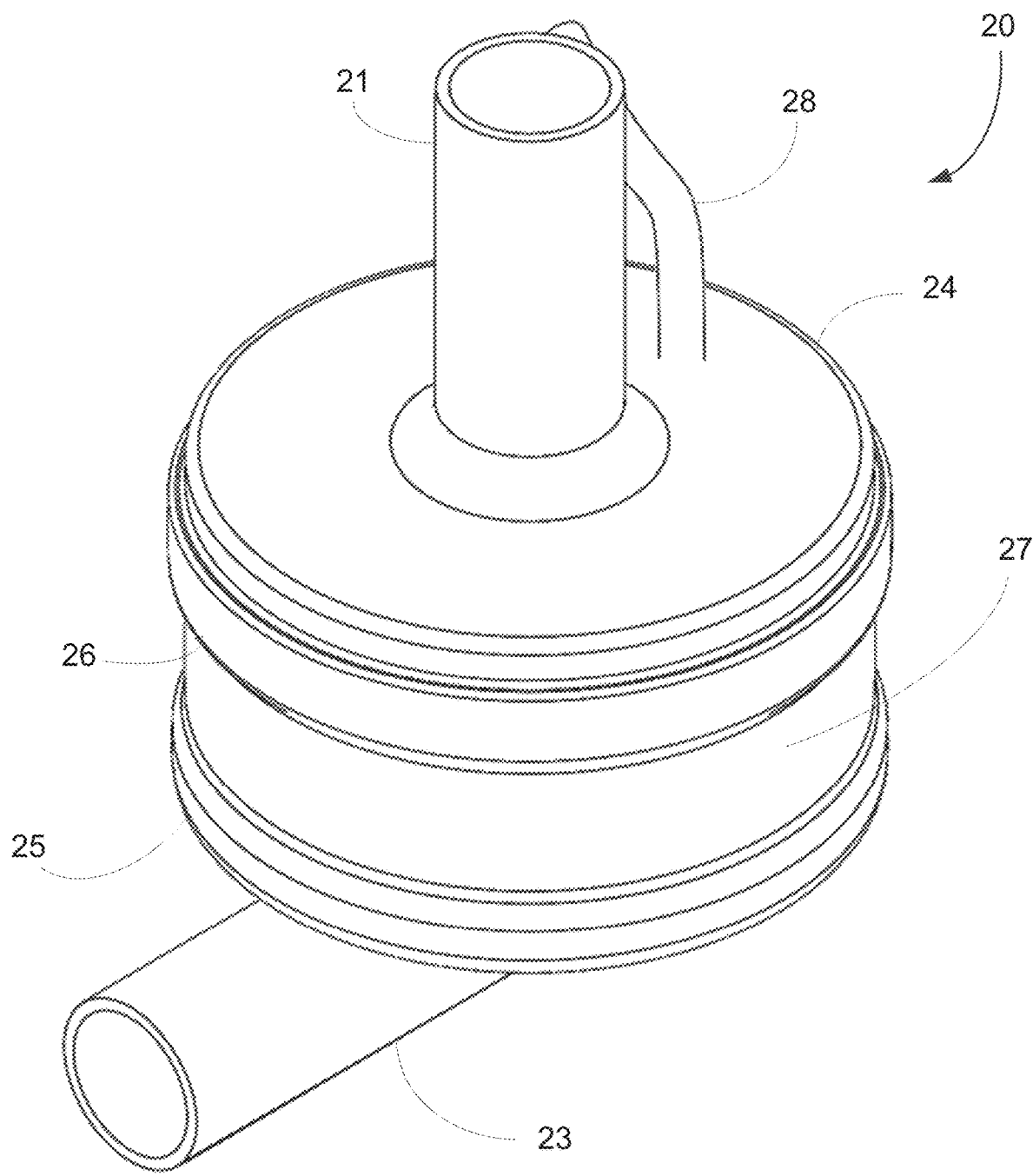
FIG. 2 is a perspective view of the blood pump of FIG. 1.

Referring now also to FIG. 2, pump 20 in a preferred embodiment consists of upper housing portion 24 joined to lower housing portion 25 along interface 26, for example, by threads or welding, to form fluid tight pump housing 27 that may have a cylindrical shape. Upper housing portion 24 includes inlet cannula 21 and electrical conduit 28 for receiving electrical wires from controller 30 and battery 40. Lower housing portion 25 includes outlet 23 that couples to outlet cannula 22, as shown in FIG. 1. Pump housing 27 is made of a biocompatible material, such as stainless steel or titanium, and is sized to be implanted within a patient's chest.

Referring again to FIG. 1, in one embodiment, controller 30 and battery 40 are extracorporeal, and are sized so as to be placed on a belt or garment worn by the patient. Both controller 30 and battery 40 are electrically coupled to pump 20, for example, via cable 29 that extends through a percutaneous opening in the patient's skin and into electrical conduit 28 of pump housing 27. Illustratively, battery 40 is electrically coupled to controller 30 via cable 41 that is integrated into belt 42. In an alternative embodiment, controller 30 may be enclosed within a biocompatible housing and sized to be implanted subcutaneously in the patient's abdomen. In this alternative embodiment, controller 30 may include a wireless transceiver for bi-directional communications with an extracorporeal programming device and also includes a battery that is continuously and inductively charged via extracorporeal battery 40 and an extracorporeal charging circuit. As will be understood, the foregoing alternative embodiment avoids the use of percutaneous cable 29, and thus eliminates a frequent source of infection for conventional LVAD devices.

Battery 40 preferably comprises a rechargeable battery capable of powering pump 20 and controller 30 for a period of several hours, e.g., 4-12 hours, before needing to be recharged. Battery 40 may include a separate charging circuit, not shown, as is conventional for rechargeable batteries. Battery 40 preferably is disposed within a housing suitable for carrying on a belt or holster, so as not to interfere with the patient's daily activities.

Programmer 50 may consist of a conventional laptop computer that is programmed to execute programmed software routines, for use by a clinician or medical professional, for configuring and providing operational parameters to controller 30. The configuration and operational parameter data are stored in a memory associated with controller 30 and used by the controller to control operation of pump 20. As described in further detail below, controller 30 directs pump 20 to operate at specific parameters determined by programmer 50. Programmer 50 preferably is coupled to controller 30 via cable 51 only when the operational parameters of the pump are initially set or periodically adjusted, e.g., when the patient visits the clinician.

In accordance with another aspect of the invention, mobile device 60, which may a conventional smartphone, may include an application program for bi-directionally and wirelessly communicating with controller 30, e.g., via WiFi or Bluetooth communications. The application program on mobile device 60 may be programmed to permit the patient to send instructions to controller to modify or adjust a limited number of operational parameters of pump 20 stored in controller 30. Alternatively or in addition, mobile device 60 may be programmed to receive from controller 30 and to display on screen 61 of mobile device 60, data relating to operation of pump 20 or alert or status messages generated by controller 30.

Figure 3A:
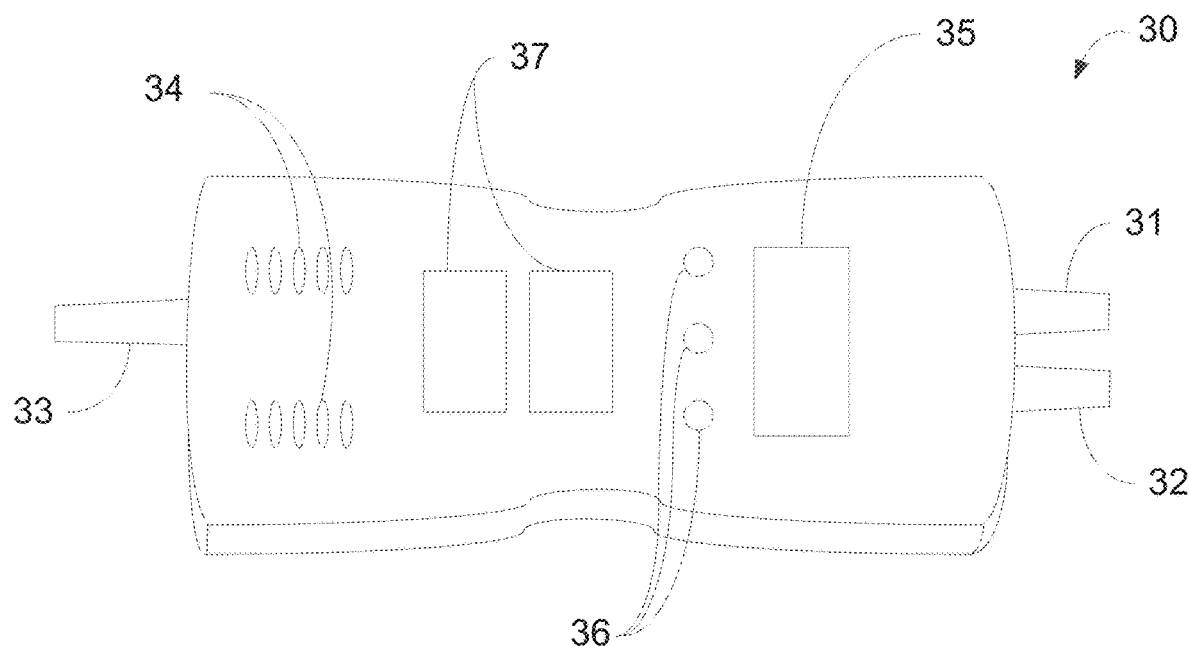
FIGS. 3A and 3B are, respectively, a perspective view and a schematic view of the electronic components of an exemplary embodiment of the controller of the present invention.
Figure 3B:
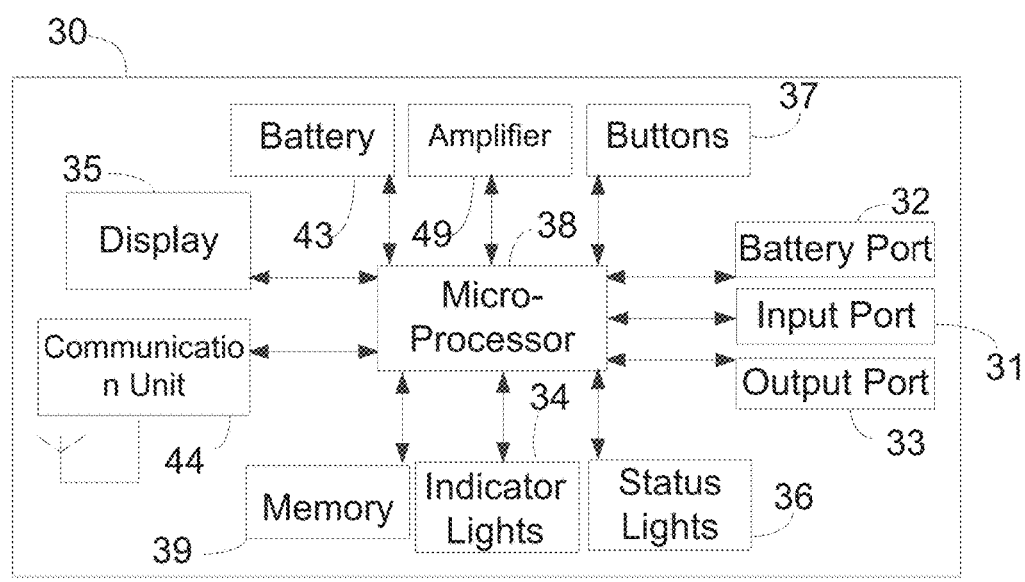

With respect to FIGS. 3A and 3B, controller 30 is described in greater detail. As depicted in FIG. 1, controller 30 may be sized and configured to be worn on the exterior of the patient's body and may be incorporated into a garment such as a belt or a vest. Controller 30 includes input port 31, battery port 32, output port 33, indicator lights 34, display 35, status lights 36 and buttons 37.

Input port 31 is configured to periodically and removably accept cable 51 to establish an electrical connection between programmer 50 and controller 30, e.g., via a USB connection. In this manner, a clinician may couple to controller 30 to set or adjust operational parameters stored in controller 30 for controlling operation of pump. In addition, when programmer 50 is coupled to controller 30, the clinician also may download from controller 30 data relating to operation of the pump, such as actuation statistics, for processing and presentation on display 55 of programmer 50, illustrated in FIG. 5A. Alternatively, or in addition, controller 30 may include a wireless transceiver for wirelessly communicating such information with programmer 50. In this alternative embodiment, wireless communications between controller 30 and programmer 50 may be encrypted with an encryption key associated with a unique identification number of the controller, such as a serial number.

Battery port 32 is configured to removably accept cable 41, illustratively shown in FIG. 1 as integrated with belt 42, so that cable 41 routed through the belt and extends around the patient's back until it couples to controller 30. In this manner, battery 40 may be removed from belt 42 and disconnected from controller 30 to enable the patient to periodically replace the battery with a fully charged battery. It is expected that the patient will have available to him or her at least two batteries, so that while one battery is coupled to controller 30 to energize the controller and pump, the other battery may be connected to a recharging station. Alternatively, or in addition, battery port 32 may be configured to accept a cable that is coupled directly to a power supply, such a substantially larger battery/charger combination that permits the patient to remove battery 40 while lying supine in a bed, e.g., to sleep.

Output port 33 is electrically coupled to cable 29, which in turn is coupled to pump 20 through electrical conduit 28 of pump housing 27. Cable 29 provides both energy to energize pump 20 in accordance with the configuration settings and operational parameters stored in controller 30, and to receive data from sensors disposed in pump 20. In one embodiment, cable 29 may comprise an electrical cable having a biocompatible coating and is designed to extend percutaneously. Cable 29 may be impregnated with pharmaceuticals to reduce the risk of infection, the transmission of potentially hazardous substances or to promote healing where it extends through the patient's skin and tissue.

As mentioned above, controller 30 may include indicator lights 34, display 35, status lights 36 and buttons 37. Indicator lights 34 may visually display information relevant to operation of the system, such as the remaining life of battery 40. Display 35 may be a digital liquid crystal display that displays real time pump performance data, physiological data of the patient, such as heart rate, or operational parameters of the pump, such as the target pump pressure or flow rate, etc. When it is determined that certain parameter conditions exceed preprogrammed thresholds, an alarm may be sounded, an alert may be displayed on display 35 and/or an internal vibrating element may vibrate controller 30 to provide tactile stimulation. Status lights 36 may comprise light emitting diodes (LEDs) that are turned on or off to indicate whether certain functionality of the controller or pump is active. Buttons 37 may be used to wake up display 35, to set or quiet alarms, etc.

With respect to FIG. 3B, the components of the illustrative embodiment of controller 30 of FIG. 3A are described. In addition to the components of controller 30 described in connection with FIG. 3A, controller 30 further includes microprocessor 38, memory 39, battery 43, optional transceiver 44 and amplifier circuitry 45. Microprocessor may be a general purpose microprocessor, for which programming to control operation of pump 20 is stored in memory 39.

Memory 39 also may store configuration settings and operational parameters for pump 20. Battery 43 supplies power to controller 30 to provide continuity of operation when battery 40 is periodically swapped out. Optional transceiver 44 (e.g., communication unit) facilitates wireless communication with programmer 50 and/or mobile device 60 via any of a number of well-known communications standards, including BLUETOOTH™, ZigBee, and/or any IEEE 802.11 wireless standard such as Wi-Fi or Wi-Fi Direct. Controller 30 further may include amplifier circuitry 49 for amplifying electrical signals transferred between controller 30 and pump 20.

Figure 4:
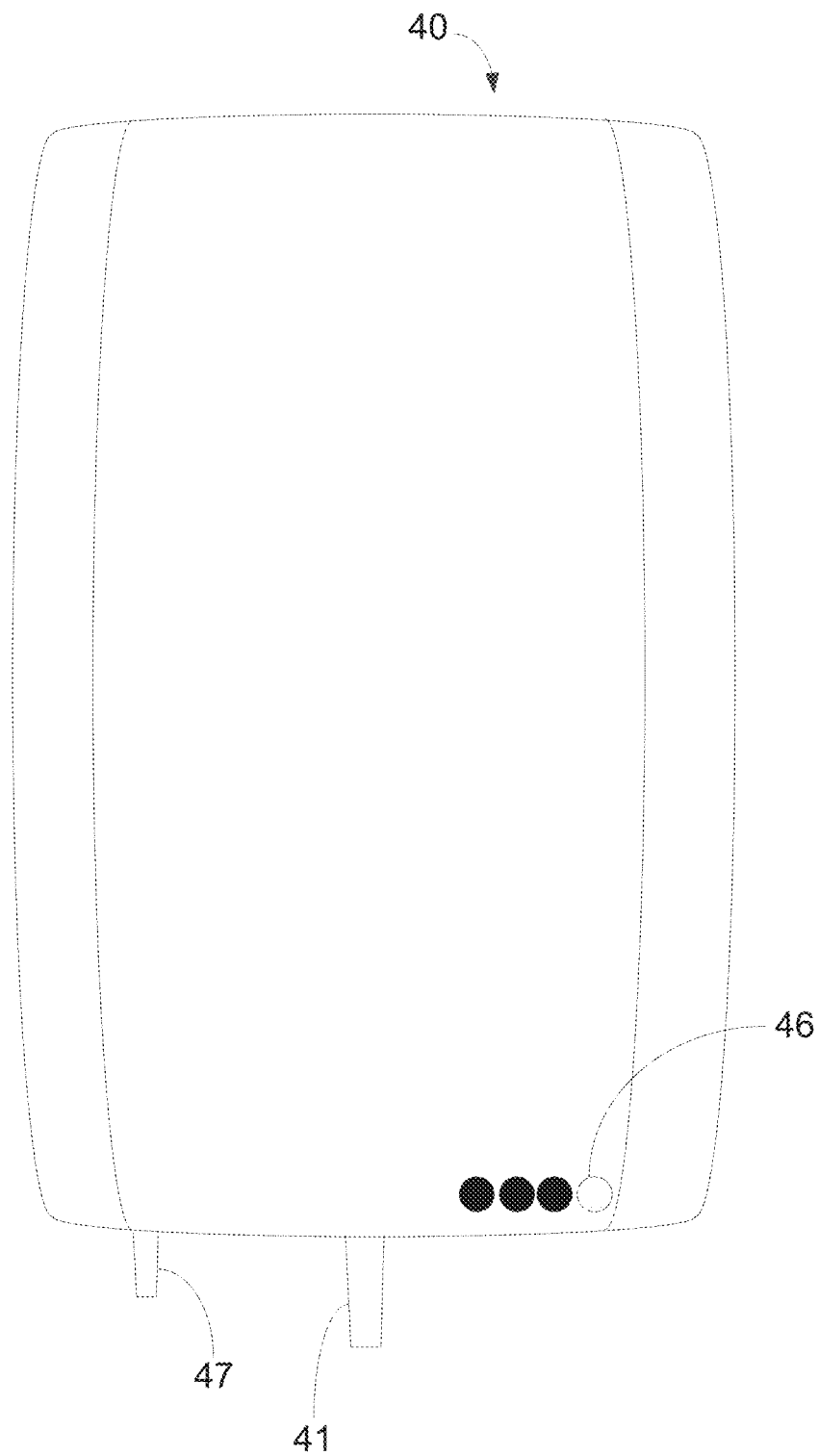
FIG. 4 is a plan view of an extracorporeal battery for use in the pump system of the present invention.

Referring now to FIG. 4, battery 40 is described. Battery 40 provides power to pump 20 and also may provide power to controller 30. Battery 40 may consist of a single battery or a plurality of batteries disposed within a housing, and preferably is sized and configured to be worn on the exterior of the patient's body, such as on belt 42. Battery life indicator 46 may be provided on the exterior of battery 40 to indicate the amount of the remaining charge of the battery. Cable 41 may have one end removably coupled to battery 40 and the other end removably coupled to battery port 32 of controller 30 to supply power to energize pump 20. In one embodiment, battery 40 may be rechargeable using a separate charging station, as is known in the art of rechargeable batteries. Alternatively, or in addition, battery 40 may include port 47 which may be removably coupled to a transformer and cable to permit the battery to be recharged using a conventional residential power outlet, e.g., 120 V, 60 Hz AC power.

Figure 5A:
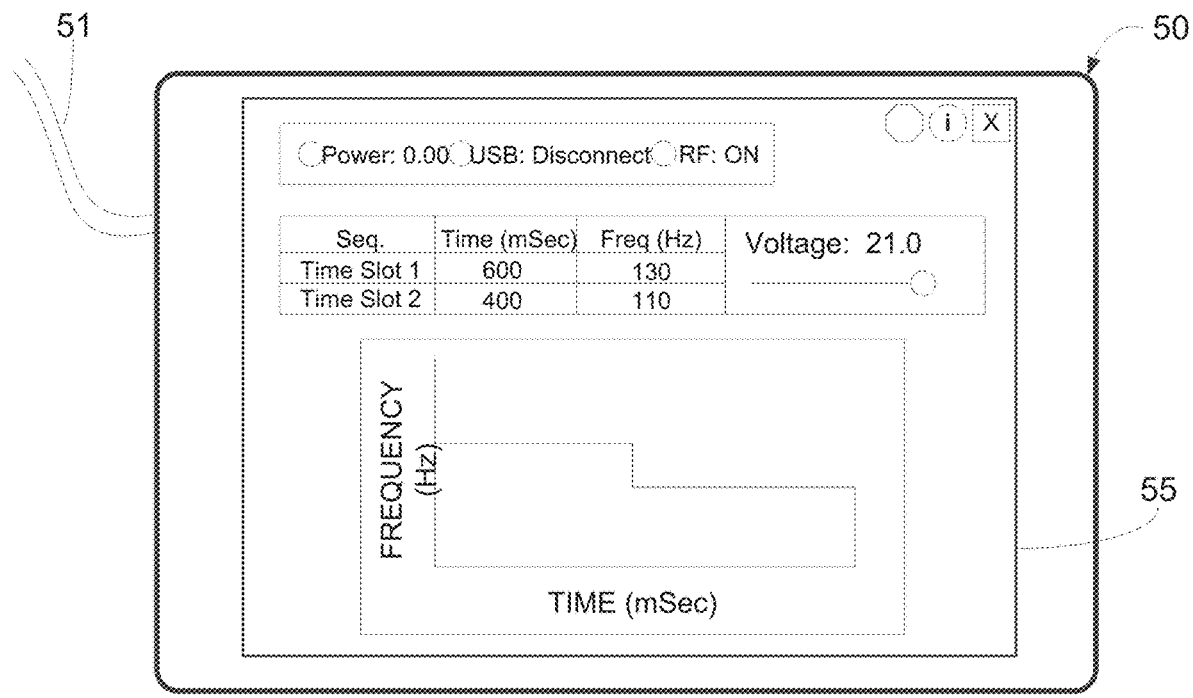
FIGS. 5A and 5B are, respectively, a perspective view and a schematic view of the electronic components of an exemplary embodiment of the programmer of the present invention.
Figure 5B:
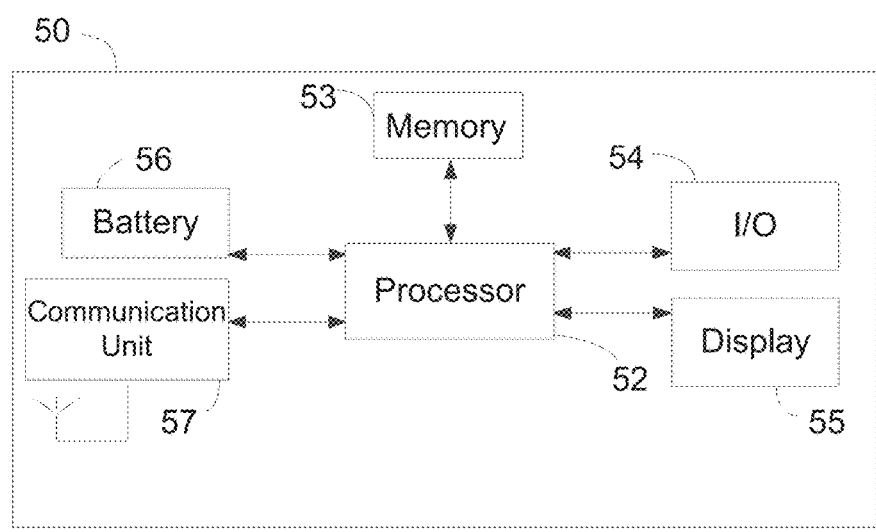

Referring now to FIGS. 5A-5B, programmer 50 is described. Programmer 50 may be a conventional laptop or tablet computer loaded with programmed software routines for configuring controller 30 and setting operational parameters that controller 30 uses to control operation of pump 20. As discussed above, programmer 50 typically is located in a clinician's office or hospital, and is coupled to controller 30 via cable 51 or wirelessly to initially set up controller 30, and then periodically thereafter as required to adjust the operational parameters as may be needed. The operation parameters of controller 30 set using the programmed routines of programmer 50 may include but are not limited to pump operating mode, applied voltage, pump frequency, pump amplitude, target flow rate, pulsatility, etc. When first implanted, the surgeon or clinician may use programmer 50 to communicate initial operating parameters to controller 30. Following implantation, the patient periodically may return to the clinician's office for adjustments to the operational parameters which may again be made using programmer 50.

Programmer 50 may be any type of conventional personal computer device such as a laptop or a tablet computer having touch screen capability. As illustrated in FIG. 5B, programmer 50 preferably includes processor 52, memory 53, input/output device 54, display 55, battery 56 and communication unit 57. Memory 53 may include the operating system for the programmer, as well as the programmed routines needed to communicate with controller 30. Communication unit 57 may include any of a number of well-known communication protocols, such as BLUETOOTH™, ZigBee, and/or any IEEE 802.11 wireless standard such as Wi-Fi or Wi-Fi Direct. As illustrated in FIG. 5A, the programmed routines used to program and communicate with controller 30 also may provide data for display on the screen of programmer 50 identifying operational parameters with which controller 30 controls pump 20. The programmed routines also may enable programmer 50 to download from controller 30 operational data or physiologic data communicated by the pump and to display that information in real time while the programmer is coupled to the controller via a wired or wireless connection. The transferred data may then be processed and displayed on the screen of programmer 50.

Figure 6:
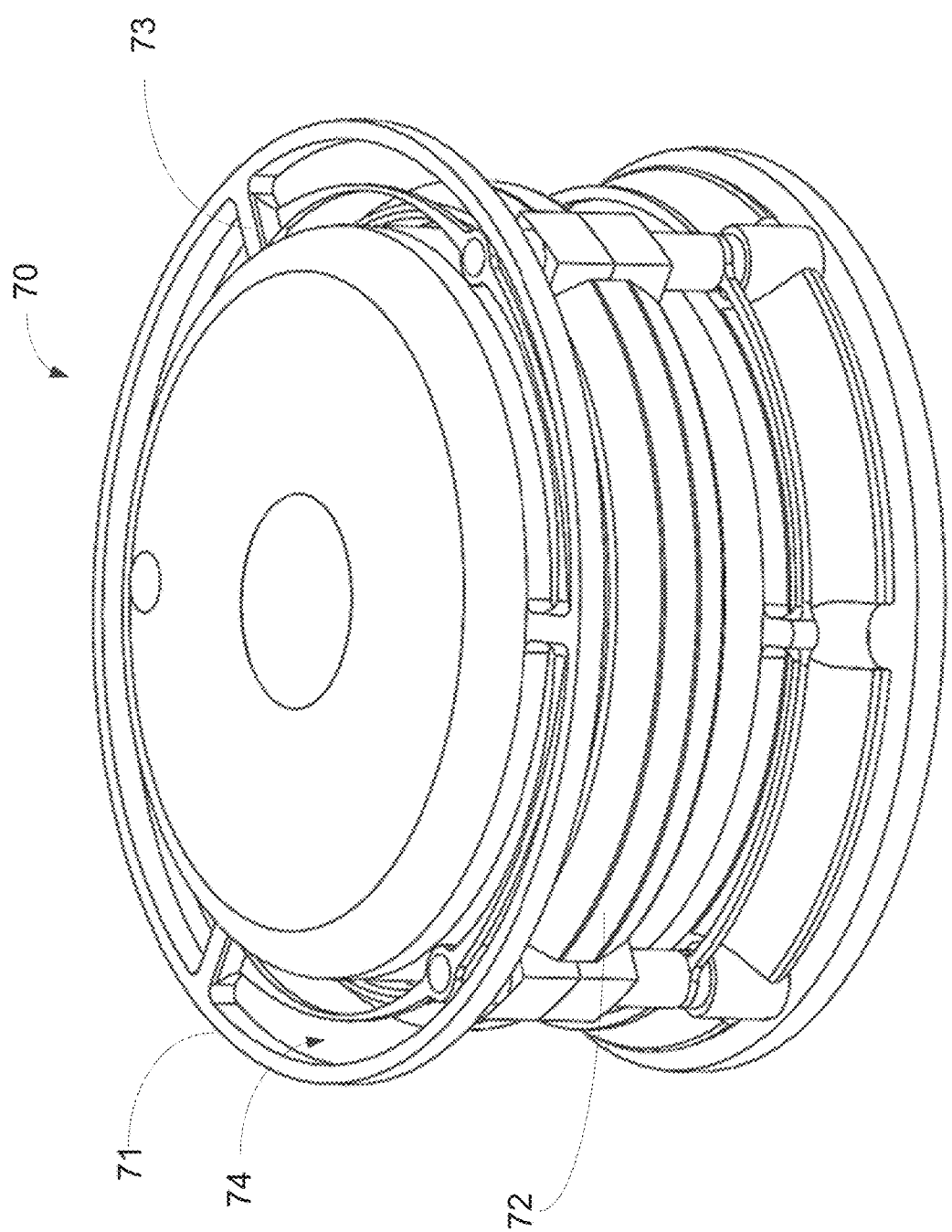
FIG. 6 is a perspective view of the pump assembly of the present invention.
Figure 7:
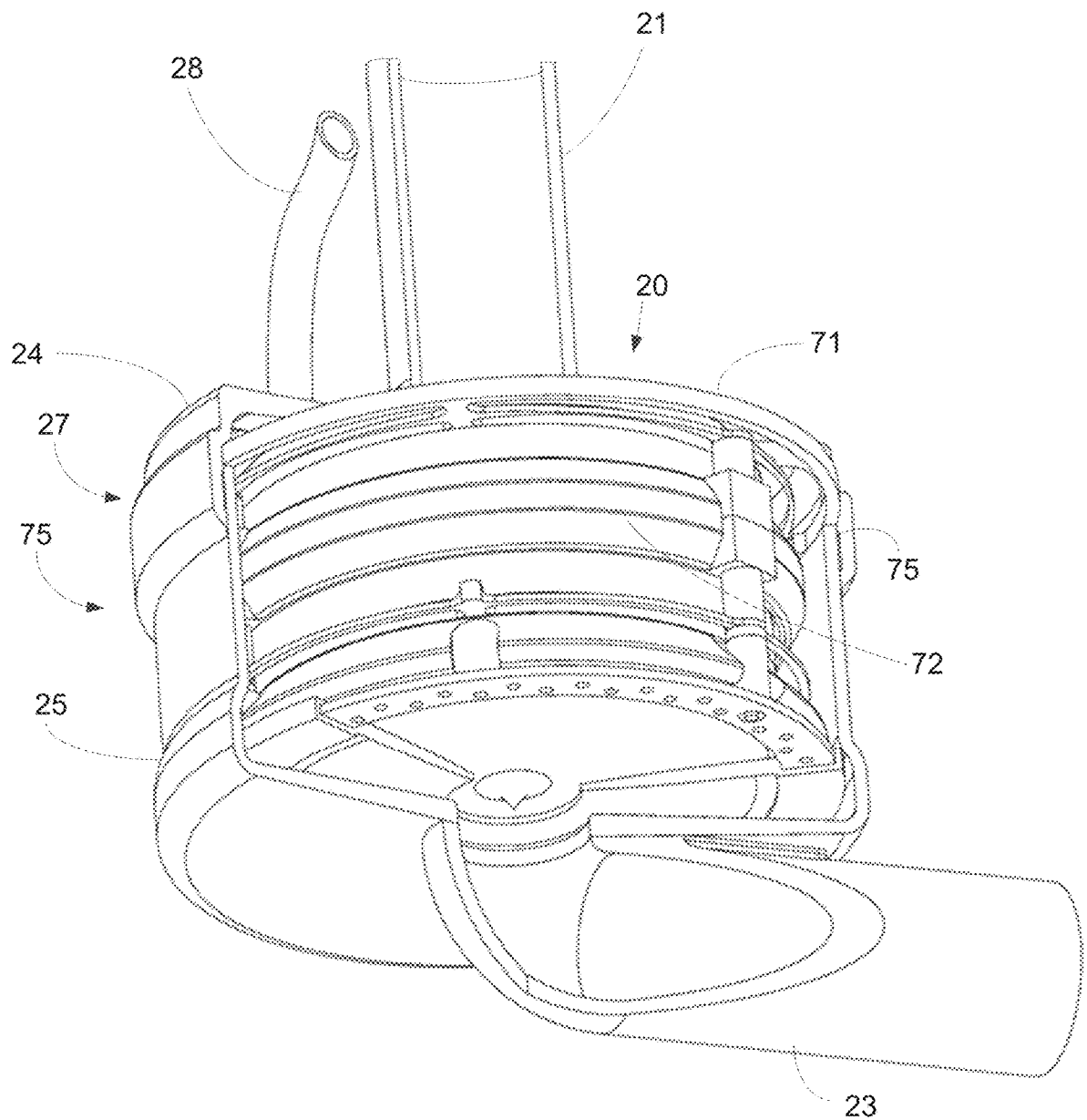
FIG. 7 is a perspective, cut-away view of the blood pump of the present invention.

Referring now to FIGS. 6 and 7, a preferred embodiment of pump assembly 70 and pump 20 are illustrated. However, it is understood that pump assemblies and pumps, and components included therein, may have different shapes and sizes than those illustrated in FIGS. 6 and 7 without departing from the invention described herein. As is illustrated in FIG. 7, pump assembly 70 is configured to fit within pump housing 27. To fix pump assembly 70 within pump housing 27, pump assembly 70 may include fixation ring 71, which may extend from and around stator assembly 72, and may be captured between upper housing portion 24 and lower housing portion 25 when the housing portions are assembled, as illustrated in FIG. 7. In this manner, stator assembly 72 may be suspended within the pump housing in close-fitting relation to the interior walls of the pump housing. Fixation ring 71 preferably is a rigid annular structure that is disposed concentrically around stator assembly 72, having a larger diameter than stator assembly 72. Fixation ring 71 may be rigidly coupled to stator assembly 72 via struts 73. Struts 73 may create gap 74 between fixation ring 71 and stator assembly 72, which preferably is about 0.05 mm at its most restricted point.

As shown in FIG. 7, pump assembly 70 may be disposed in pump housing 27 such that fixation ring 71 is captured on step 75 formed between upper housing portion 24 and lower housing portion 25. In this manner, stator assembly 72 may be suspended within, and prevented from moving within, pump housing 27. Pump housing 27 preferably is sized and configured to conform to pump assembly 70 such that, stator assembly 72 does not contact the interior of the pump housing at any location other than at fixation ring 71.

Figure 8:
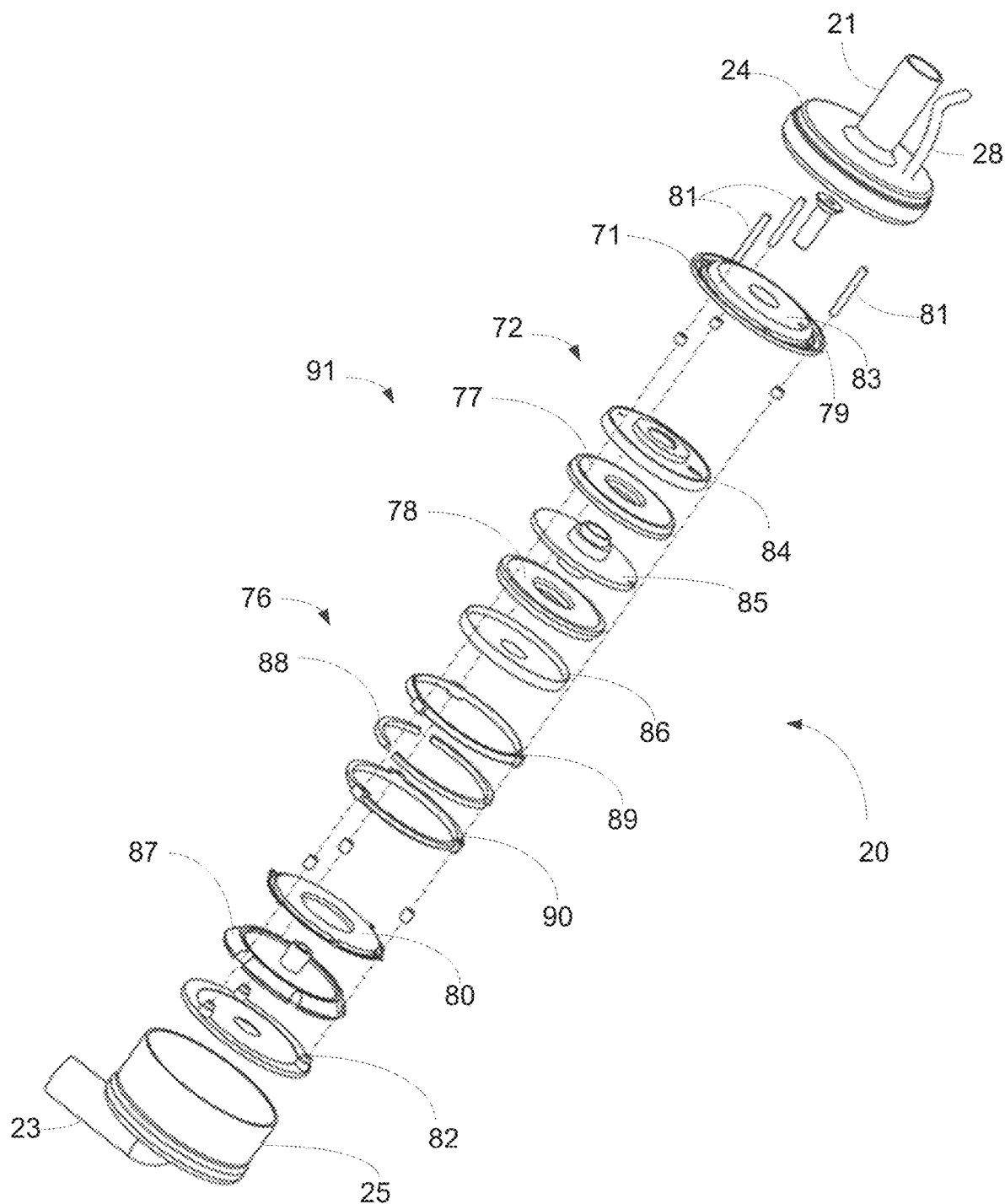
FIG. 8 is an exploded view of the blood pump of the present invention.

FIG. 8 is an exploded view of pump 20, depicting the arrangement of the internal components of pump assembly 70 arranged between upper housing portion 24 and lower housing portion 25. In particular, pump assembly 70 may comprise stator assembly 72, magnetic ring assembly 76, first electromagnetic coil 77, second electromagnetic coil 78, fixation ring 71, first suspension ring 79, second suspension ring 80, posts 81 and membrane assembly 82. Stator assembly 72 may comprise tapered section 83, electromagnetic coil holder portions 84, 85 and 86, and flanged portion 87. Magnetic ring assembly 76 may comprise magnetic ring 88 and magnetic ring holder portions 89 and 90. First and second electromagnetic coils 77 and 78, together with electromagnetic coil holder portions 84, 85 and 86 may form electromagnetic assembly 91. Electromagnetic assembly 91 together with stator assembly 72 form an actuator assembly. The actuator assembly together with magnetic ring assembly 76 in turn forms the actuator system of pump 20.

First electromagnetic coil 77 and second electromagnetic coil 78 may be concentrically sandwiched between electromagnetic coil holder portions 84, 85 and 86 to form electromagnetic assembly 91. Tapered section 83, which may be coupled to fixation ring 71 and first suspension spring 79, may be located concentrically atop electromagnetic assembly 91. Magnetic ring 88 may be disposed with magnetic ring holder portions 89 and 90 to form magnetic ring assembly 76, which may be concentrically disposed for reciprocation over electromagnetic assembly 91. Second suspension ring 80 may be disposed concentrically beneath electromagnetic assembly 91. Flanged portion 87 may be concentrically disposed below second suspension ring 80. Posts 81 may engage first suspension ring 79, magnetic ring assembly 76 and second suspension ring 80 at equally spaced locations around the actuator assembly. Membrane assembly 82 may be positioned concentrically below flanged portion 87 and engaged with posts 81.

Figure 9:
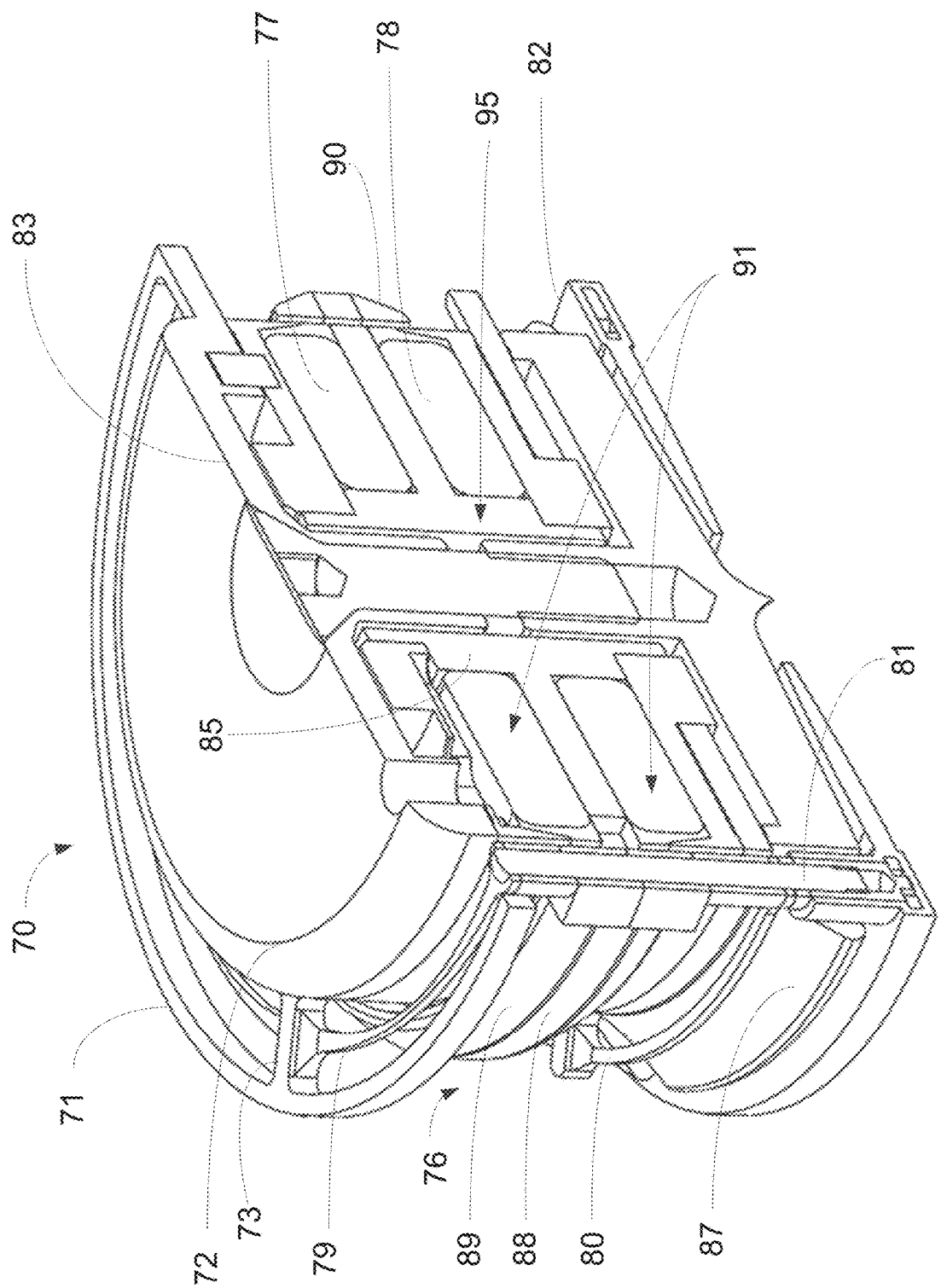
FIG. 9 is a perspective cross-sectional view of the pump assembly of the present invention.

Further details of pump assembly 70 are provided with respect to FIG. 9. Specifically, actuator assembly 95 comprises stator assembly 72 and electromagnetic assembly 91, including first and second electromagnetic coils 77 and 78. During use of pump 20, actuator assembly 95 remains stationary relative to pump housing 27. First electromagnetic coil 77 and second electromagnetic coil 78 may be separated by electromagnetic holder portion 85. Controller 30 and battery 40 are electrically coupled to electromagnetic coils 77 and 78 via cable 29 that extends through electrical conduit 28 of pump housing 27 to supply current to electromagnetic coils 77 and 78. First electromagnetic coil 77 and second electromagnetic coil 78 may be in electrical communication with one another or may be configured to operate independently and have separate wired connections to controller 30 and battery 40 via cable 29.

Electromagnetic coils 77 and 78 may be made of any electrically conductive metallic material such as copper and further may comprise of one or more smaller metallic wires wound into a coil. The wires of the electromagnetic coils are insulated to prevent shorting to adjacent conductive material. Other components of pump assembly 70, such as stator assembly 72, preferably also are insulated and/or made of non-conductive material to reduce unwanted transmission of the electrical signal.

Actuator assembly 95 may be surrounded by first suspension ring 79 and second suspension ring 80. Suspension rings 79 and 80 may be annular in shape and fit concentrically around actuator assembly 95. First suspension ring 79 preferably is rigidly affixed to tapered section 83 near a top portion of stator assembly 72 via struts 73 extending from the suspension ring to the stator assembly. As discussed above, struts 73 may also affix fixation ring 71 to stator assembly 72. Fixation ring 71 and first suspension spring 79 may be sized and positioned such that a gap of no less than 0.5 mm exists between first suspension ring 79 and fixation ring 71. Second suspension ring 80 similarly may be rigidly affixed via struts near the bottom of stator assembly 72, below electromagnetic assembly 91. Suspension rings 79 and 80 preferably are sized and shaped such that when suspension rings 79 and 80 are positioned surrounding actuator assembly 95, a gap of no less than 0.5 mm exists between actuator assembly 95 and suspension rings 79 and 80.

First suspension ring 79 and second suspension ring 80 may comprise stainless steel, titanium, or cobalt chromium alloys having elastic properties and which exhibits a spring force when deflected in a direction normal to the plane of the spring. First suspension ring 79 and second suspension ring 80 may be substantially rigid with respect to forces applied tangential to the suspension ring. In this manner, first suspension ring 79 and second suspension ring 80 may exhibit a spring tension when deformed up and down relative to a vertical axis of the actuator assembly but may rigidly resist movement along any other axis, e.g., tilt or twist movements.

Magnetic ring assembly 76 may be annular in shape and concentrically surrounds actuator assembly 95. Magnetic ring 88 may comprise one or more materials exhibiting magnetic properties such as iron, nickel, cobalt or various alloys. Magnetic ring 88 may be made of a single unitary component or comprise several magnetic components that are coupled together. Magnetic ring assembly 76 may be sized and shaped such that when it is positioned concentrically over actuator assembly 95, a gap of no less than 0.5 mm exists between an outer lateral surface of actuator assembly 95 and an interior surface of magnetic ring assembly 76.

Magnetic ring assembly 76 may be concentrically positioned around actuator assembly 95 between first suspension ring 79 and second suspension ring 80, and may be rigidly coupled to first suspension ring 79 and second suspension ring 80. Magnetic ring assembly 76 may be rigidly coupled to the suspension rings by more than one post 81 spaced evenly around actuator assembly 95 and configured to extend parallel to a central axis of pump assembly 70. Suspension rings 79 and 80 and magnetic ring assembly 76 may be engaged such that magnetic ring assembly 76 is suspended equidistant between first electromagnetic coil 77 and second electromagnetic coil 78 when the suspension rings are in their non-deflected shapes. Each of suspension rings 79 and 80 and magnetic ring holder portions 89 and 90 may include post receiving regions for engaging with posts 81 or may be affixed to posts 81 in any suitable manner that causes suspension rings 79 and 80 and magnetic ring assembly 76 to be rigidly affixed to posts 81. Posts 81 may extend beyond suspension rings 79 and 80 to engage other components, such as flanged portion 87 and membrane assembly 82.

First electromagnetic coil 77 may be activated by controller applying an electrical signal from battery 40 to first electromagnetic coil 77, thus inducing current in the electromagnetic coil and generating a magnetic field surrounding electromagnetic coil 77. The direction of the current in electromagnetic coil 77 and the polarity of magnetic ring assembly 76 nearest electromagnetic coil 77 may be configured such that the first electromagnetic coil magnetically attracts or repeals magnetic ring assembly 76 as desired. Similarly, a magnetic field may be created in second electromagnetic coil 78 by introducing a current in the second electromagnetic coil. The direction of the current in second electromagnetic coil 78 and the polarity of magnetic ring assembly 76 nearest the second electromagnetic coil also may be similarly configured so that first electromagnetic coil 77 magnetically attracts or repels magnetic ring assembly 76 when an appropriate current is induced in second electromagnetic coil 78.

Because magnetic ring assembly 76 may be rigidly affixed to posts 81, which in turn may be rigidly affixed to first suspension ring 79 and second suspension ring 80, the elastic properties of the suspension rings permit magnetic ring assembly 76 to move up towards first electromagnetic coil 77 or downward toward second electromagnetic coil 78, depending upon the polarity of magnetic fields generated by the electromagnetic rings. In this manner, when magnetic ring assembly 76 experiences an upward magnetic force, magnetic ring assembly 76 deflects upward towards first electromagnetic coil 77. As posts 81 move upward with magnetic ring assembly 76, posts 81 cause the suspensions rings 79 and 80 to elastically deform, which creates a spring force opposite to the direction of movement. When the magnetic field generated by the first electromagnetic coil collapses, when the electrical current ceases, this downward spring force causes the magnetic ring assembly to return to its neutral position. Similarly, when magnetic ring assembly 76 is magnetically attracted downward, magnetic ring assembly 76 deflects downward towards second electromagnetic ring 78. As posts 81 move downward with magnetic ring assembly 76, posts 81 impose an elastic deformation of the first and second suspension rings, thus generating a spring force in the opposite direction. When the magnetic field generated by the second electromagnetic ring collapses, when the electrical current ceases, this upward spring force causes the magnetic ring assembly to again return to its neutral position.

Electromagnetic coils 77 and 78 may be energized separately, or alternatively, may be connected in series to cause the electromagnetic coils to be activated simultaneously. In this configuration, first magnetic coil may be configured to experience a current flow direction opposite that of the second electromagnetic coil. Accordingly, when current is induced to first electromagnetic coil 77 to attract magnetic ring assembly 76, the same current is applied to second electromagnetic coil 78 to induce a current that causes second electromagnetic coil 78 to repel magnetic ring assembly 76. Similarly, when current is induced to second electromagnetic coil 78 to attract magnetic ring assembly 76, the current applied to first electromagnetic coil 77 causes the first electromagnetic coil to repel magnetic ring assembly 76. In this manner, electromagnetic coils 77 and 78 work together to cause deflection of magnetic ring assembly 76.

By manipulating the timing and intensity of the electrical signals applied to the electromagnetic coils, the frequency at which magnetic ring assembly 76 deflects towards the first and second electromagnetic coils may be altered. For example, by alternating the current induced in the electromagnetic coils more frequently, the magnetic ring assembly may be caused to cycle up and down more times in a given period. By increasing the amount of current, the magnetic ring assembly may be deflected at a faster rate and caused to travel longer distances.

Alternatively, first electromagnetic coil 77 and second electromagnetic coil 78 may be energized independently. For example, first electromagnetic coil 77 and second electromagnetic coil 78 may be energized at varying intensities; one may be coordinated to decrease intensity as the other increases intensity. In this manner, intensity of the signal applied to second electromagnetic coil 78 to cause downward magnetic attraction may simultaneously be increased as the intensity of the signal applied to first electromagnetic coil 77 causes an upward magnetic attraction that decreases.

In accordance with one aspect of the invention, movements of magnetic ring assembly 76 may be translated to membrane assembly 82 which may be disposed concentrically below stator assembly 72. Membrane assembly 82 preferably is rigidly attached to magnetic ring assembly 76 by posts 81. In the embodiment depicted in FIG. 9, posts 81 may extend beyond second suspension ring 80 and coupled to membrane assembly 82.

Figure 10:
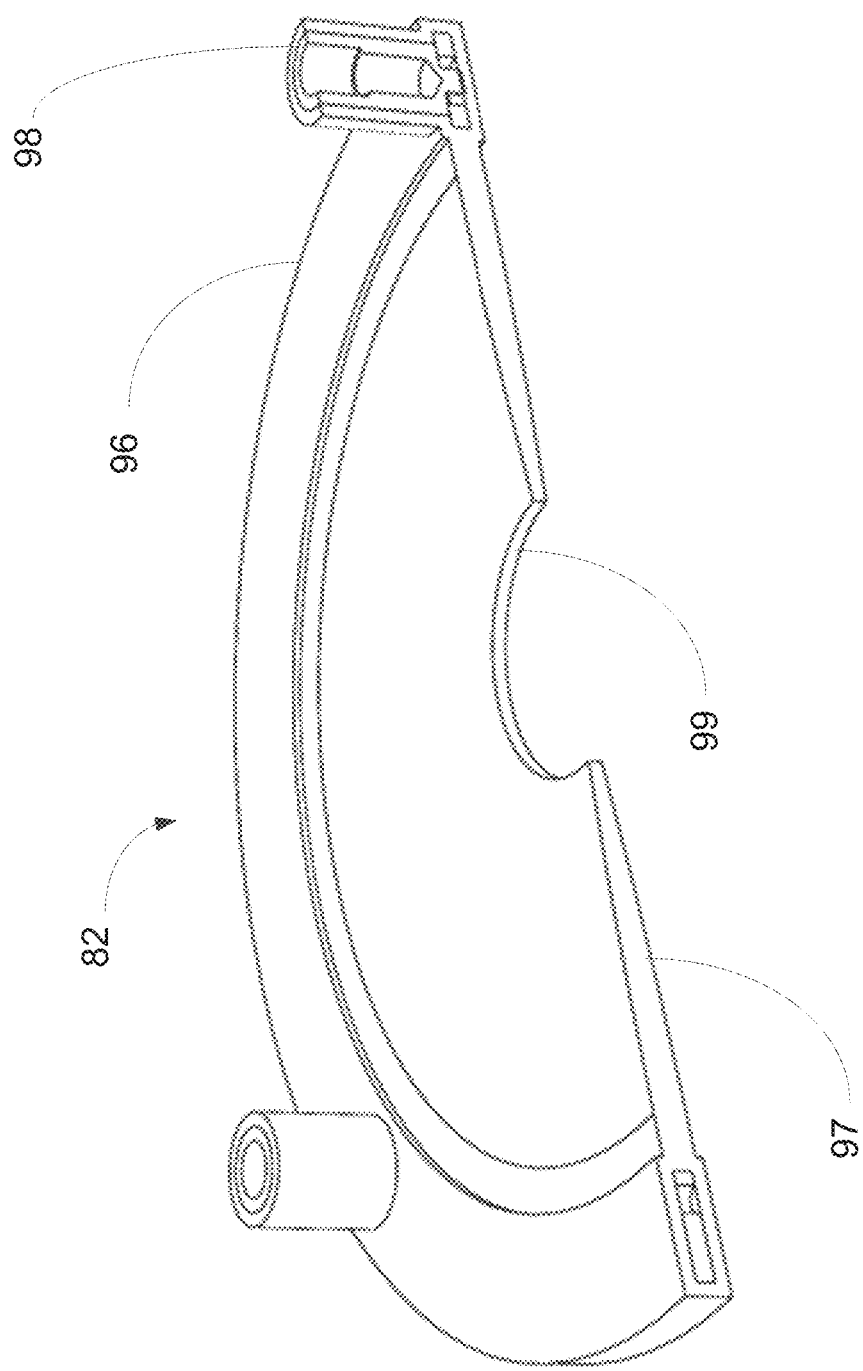
FIG. 10 is a perspective cross-sectional view of the membrane assembly of the present invention.

Referring now to FIG. 10, one embodiment of membrane assembly 82 is described in greater detail. Membrane assembly 82 may comprise rigid membrane ring 96 and membrane 97. Rigid membrane ring 96 exhibits rigid properties under typical forces experienced during the full range of operation of the present invention. Post reception sites 98 may be formed into rigid membrane ring 96 to engage membrane assembly 82 with posts 81. Alternatively, posts 81 may be attached to rigid membrane ring 96 in any other way which directly translates the motion of magnetic ring assembly 76 to rigid membrane ring 96. Rigid membrane ring 96 may be affixed to membrane 97 and hold the membrane in tension. Membrane 97 may be molded directly onto rigid membrane ring 96 or may be affixed to rigid membrane ring 96 in any way that holds membrane 97 uniformly in tension along its circumference. Membrane 97 alternatively may include a flexible pleated structure where it attaches to rigid membrane ring 96 to increase the ability of the membrane to move where the membrane is affixed to rigid membrane ring 96. Membrane 97 may further include circular aperture 99 disposed in the center of the membrane.

In a preferred embodiment, membrane 97 has a thin, planar shape and is made of an elastomer having elastic properties and good durability. Alternatively, membrane 97 may have a uniform thickness from the membrane ring to the circular aperture. As a yet further alternative, membrane 97 may vary in thickness and exhibit more complex geometries. For example, as shown in FIG. 10, membrane 97 may have a reduced thickness as the membrane extends from rigid membrane ring 96 to circular aperture 99. Alternatively, or in addition to, membrane 97 may incorporate metallic elements such as a spiral spring to enhance the spring force of the membrane in a direction normal to plane of the membrane, and this spring force may vary radially along the membrane. In yet another embodiment, membrane 97 may be pre-formed with an undulating shape.

Figure 11:
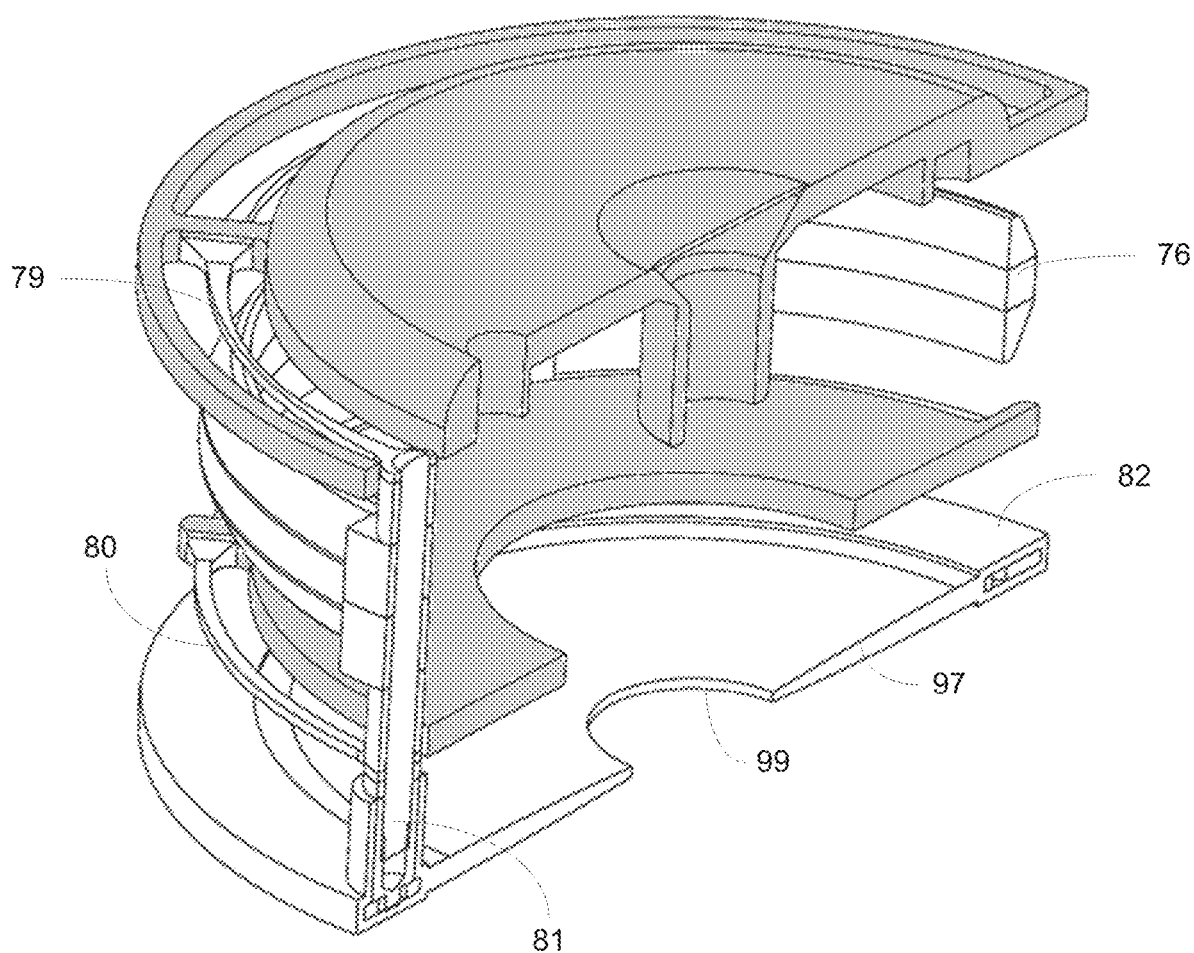
FIG. 11 is a perspective cross-sectional view of the moving components of the pump assembly according to a first embodiment of the present invention.

FIG. 11 depicts moving portions of the embodiment of pump assembly 70 shown in FIGS. 6-9 as non-grayed out elements. Non-moving portions of the pump assembly, including actuator assembly 95 and electromagnetic assembly 91 (partially shown) may be fixed to pump housing 27 by fixation ring 71. Moving portions of pump assembly 70 may include posts 81, first suspension spring 79, magnetic ring assembly 76, second suspension spring 80 and membrane assembly 82. As magnetic ring assembly 76 moves up and down, the movement is rigidly translated by posts 81 to membrane assembly 82. Given the rigidity of the posts, when magnetic ring assembly 76 travels a certain distance upward or downward, membrane assembly 82 may travel the same distance. For example, when magnetic ring assembly 76 travels 2 mm from a position near first electromagnetic coil 77 to a position near second electromagnetic coil 78, membrane assembly 82 may also travel 2 mm in the same direction. Similarly, the frequency at which magnetic ring assembly 76 traverses the space between the first and second electromagnetic coils may be the same frequency at which membrane assembly 82 travels the same distance.

Figure 12:
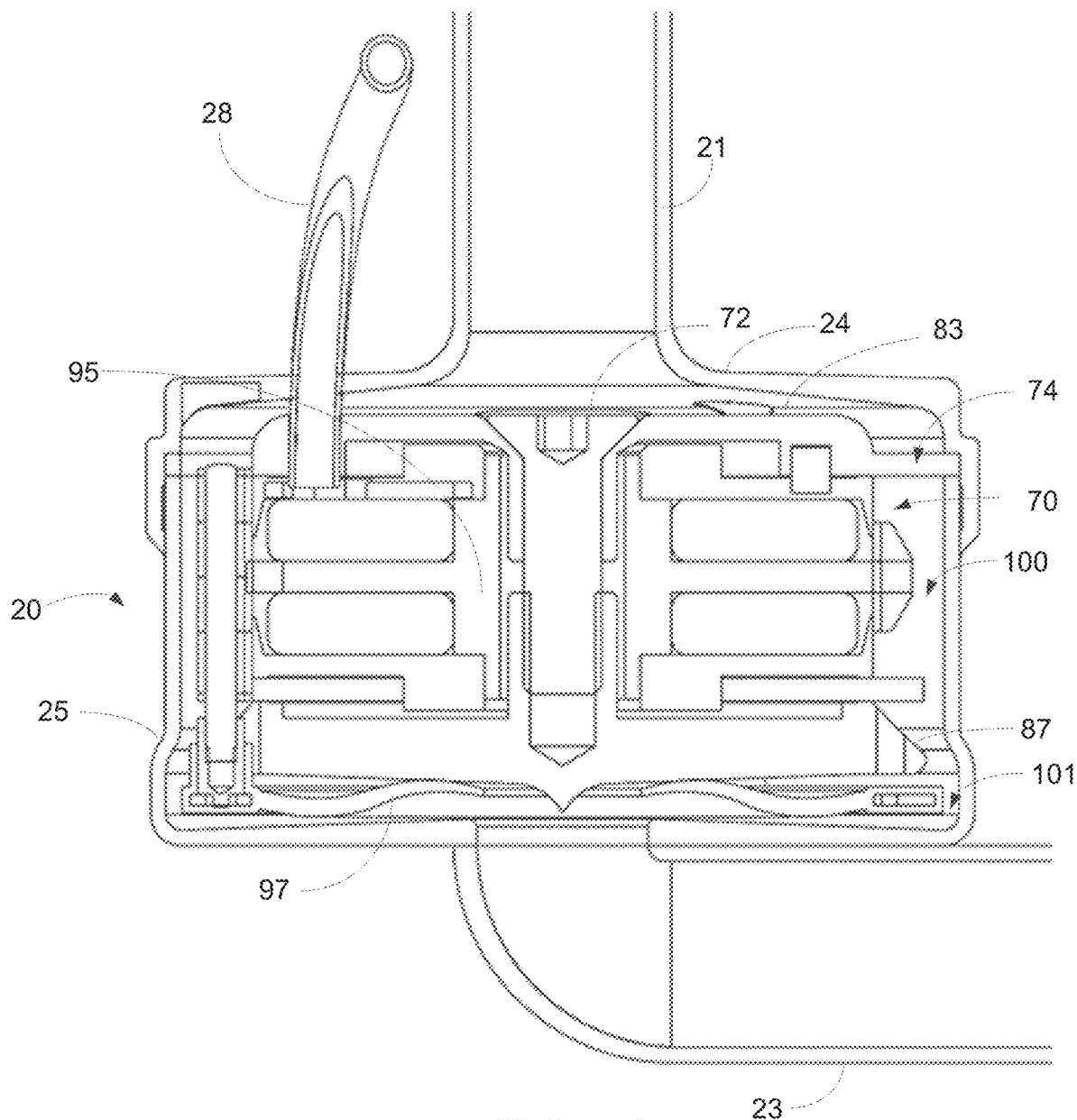
FIG. 12 is a cross-sectional view of the blood pump of the present invention.

Referring now to FIG. 12, in the embodiment of pump 20 described in FIGS. 6-9, blood may enter pump 20 from the left ventricle through inlet cannula 21 and flow downward along pump assembly 70 into delivery channel 100, defined by the interior surface of pump housing 27 and exterior of pump assembly 70. Delivery channel 100 begins at the top of stator assembly 72 and extends between tapered section 83 and the interior of pump housing 27. As the blood moves down tapered section 83, it is directed through gap 74 and into a vertical portion of delivery channel 100 in the area between pump housing 27 and actuator assembly 95, and including in the gap between magnetic ring assembly 76 and electromagnetic assembly 91. Delivery channel 100 extends down to flanged portion 87 of stator assembly 72, which routes blood into flow channel 101, within which membrane assembly 82 is suspended. By directing blood from inlet cannula 21 through delivery channel 100 to flow channel 101, delivery channel 100 delivers blood to membrane assembly 82. By actuating electromagnetic coils 77 and 78, membrane 97 may be undulated within flow channel 101 to induce wavelike formations in membrane 97 that move from the edge of the membrane towards circular aperture 99. Accordingly, when blood is delivered to membrane assembly 82 from delivery channel 100, it may be propelled radially along both the top and bottom of membrane 97 towards circular aperture 99, and from there out of outlet 23.

In accordance with one aspect of the present invention, the undulating membrane pump described herein reduces thrombus formation by placing moving parts directly within the primary flow path, thereby reducing the risk of flow stagnation. Specifically, the moving components depicted in FIG. 11, including magnetic ring assembly 76, suspension rings 79 and 80, posts 81 and membrane assembly 82 all are located within delivery channel 100 and flow channel 101. Flow stagnation may further be avoided by eliminating secondary flow paths that may experience significantly slower flow rates. The width of the fluid passages, i.e., delivery channel 100 and flow channel 101, may be optimized to minimize blood exposure to shear conditions. The flow channels may be sized and shaped to optimize hydraulic performance. Specifically, flow channel 101 may be sized and configured to facilitate blood flow towards the outlet and resist blood flow towards the inlet. It is understood that the size and shape of flow channels may affect blood flow through the pump and that an optimal size and shape may be selected to optimize hydraulic performance. For example, the size and shape of flow channels may be optimized to resist backflow and recirculation while permitting forward flow; thus, backflow is resisted without choking of the forward flow.

Turning now to FIGS. 13 and 14, a lower portion of pump 20, including flanged portion 87, membrane assembly 82 and lower housing portion 25 is shown. Delivery channel 100 may be in fluid communication with membrane assembly 82 and flow channel 101 which is defined by a bottom surface of flanged portion 87 and the interior surface of lower housing portion 25. Flanged portion 87 may comprise feature 102 that extends downward as the bottom of flanged portion 87 moves radially inward. The interior surface of lower housing portion 25 may also slope upward as it extends radially inward. The combination of the upward slope of the interior surface of lower housing portion 25 and the bottom surface of flanged portion 87 moving downward narrows flow channel 101 as the channel moves radially inwards from delivery channel 100 to circular aperture 99 of membrane 97, which is disposed about pump outlet 23.

As explained above, membrane assembly 82 may be suspended by posts 81 within flow channel 101 below the bottom surface of flanged portion 87 and above the interior surface of lower housing portion 25. Membrane assembly 82 may be free to move up and down in the vertical direction within flow channel 101, which movement is constrained only by suspension rings 79 and 80. Membrane assembly 82 may be constrained from twisting, tilting or moving in any direction in flow channel 101 other than up and down by rigid posts 81 and by the suspension rings.

Flow channel 101 is divided by membrane 97 into an upper flow channel and a lower flow channel by membrane 97. The geometry of membrane 97 may be angled such that when membrane assembly 82 is at rest, the top surface of membrane 97 is parallel to the bottom surface of flanged portion 87 and the bottom surface of membrane 97 is parallel to the opposing surface of lower housing portion 25. Alternatively, membrane 97 may be sized and shaped such that when membrane assembly 82 is at rest, the upper and lower flow channels narrow as they move radially inward from delivery channel 100 to circular aperture 99 in membrane 97.

Referring now also to FIG. 14, as rigid membrane ring 96 is caused by posts 81 to move up and down in flow channel 101, the outermost portion of membrane 97 nearest rigid membrane ring 96, moves up and down with rigid membrane ring 96. Membrane 97, being flexible and having elastic properties, gradually translates the up and down movement of the membrane portion nearest rigid membrane ring 96 along membrane 97 towards circular aperture 99. This movement across flexible membrane 97 causes wave-like deformations in the membrane which may propagate inwards from rigid membrane ring 96 towards aperture 99.

The waves formed in the undulating membrane may be manipulated by changing the frequency at which rigid membrane ring 96 moves up and down as well as the distance rigid membrane ring 96 moves up and down. As explained above, the amplitude and frequency at which rigid membrane ring 96 moves up and down is determined by the amplitude and frequency at which magnetic ring assembly 76 reciprocates over electromagnetic assembly 91. Accordingly, the waves formed in the undulating membrane may be adjusted by changing the frequency and amplitude at which magnetic ring assembly 76 is reciprocated.

When blood is introduced into flow channel 101 from delivery channel 100, the undulations in membrane 97 cause blood to be propelled toward circular aperture 99 and out of pump housing 27 via outlet 23. The transfer of energy from the membrane to the blood is directed radially inward along the length of the membrane towards aperture 99, and propels the blood along the flow channel towards outlet 23 along both sides of membrane 97.

For example, when rigid membrane ring 96 moves downward in unison with magnetic ring assembly 76, the upper portion of flow channel 101 near delivery channel 100 expands, causing blood from delivery channel 100 to fill the upper portion of the flow channel near the outer region of membrane 97. As rigid membrane ring 96 moves upward, the upper portion of flow channel 101 begins to narrow near rigid membrane ring 96, causing wave-like deformations to translate across the membrane. As the wave propagates across membrane 97, blood in the upper portion of flow channel 101 is propelled towards circular aperture and ultimately out of pump housing 27 through outlet 23. Simultaneously, as rigid membrane ring 96 moves upwards, the lower portion of flow channel 101 nearest the outer portion of membrane 97 begins to enlarge, allowing blood from delivery channel 100 to flow into this region. Subsequently, when rigid membrane ring 96 is again thrust downwards, the region of lower portion of flow channel 101 nearest outer portion of membrane 97 begins to narrow, causing wave-like deformations to translate across the membrane that propel blood towards outlet 23.

By manipulating the waves formed in the undulating membrane by changing the frequency and amplitude at which magnetic ring assembly 76 moves up and down, the pressure gradient within flow channel 101 and ultimately the flow rate of the blood moving through flow channel 101 may be adjusted. Appropriately controlling the movement of magnetic ring assembly 76 permits oxygen-rich blood to be effectively and safely pumped from the left ventricle to the aorta and throughout the body as needed.

In addition to merely pumping blood from the left ventricle to the aorta, pump 20 of the present invention may be operated to closely mimic physiologic pulsatility, without loss of pump efficiency. In the embodiment detailed above, pulsatility may be achieved nearly instantaneously by changing the frequency and amplitude at which magnetic ring assembly 76 moves, to create a desired flow output, or by ceasing movement of the magnetic ring assembly for a period time to create a period of low or no flow output. Unlike typical rotary pumps, which require a certain period of time to attain a set number of rotations per minute to achieve a desired fluid displacement and pulsatility, pump 20 may achieve a desired flow output nearly instantaneously and similarly may cease output nearly instantaneously due to the very low inertia generated by the small moving mass of the moving components of the pump assembly. The ability to start and stop on-demand permits rapid changes in pressure and flow. Along with the frequency and amplitude, the duty cycle, defined by the percentage of time membrane 97 is excited over a set period of time, may be adjusted to achieve a desired flow output and pulsatility, without loss of pump efficiency. Even holding frequency and amplitude constant, flow rate may be altered by manipulating the duty cycle between 0 and 100%.

In accordance with another aspect of the invention, controller 30 may be programmed by programmer 50 to operate at selected frequencies, amplitudes and duty cycles to achieve a wide range of physiologic flow rates and with physiologic hemodynamics. For example, programmer 50 may direct controller 30 to operate pump 20 at a given frequency, amplitude and/or duty cycle during a period of time when a patient is typically sleeping and may direct controller 30 to operate pump 20 at a different frequency, amplitude and or duty cycle during time periods when the patient is typically awake. Controller 30 or pump also may include an accelerometer or position indicator to determine whether the patient is supine or ambulatory, the output of which may be used to move from one set of pump operating parameters to another. When the patient experiences certain discomfort or a physician determines that the parameters are not optimized, physician may alter one or more of at least frequency, amplitude and duty cycle to achieve the desired functionality. Alternatively, controller 30 or mobile device 60 may be configured to alter one or more of frequency, amplitude and duty cycle to suit the patient's needs.

Pump 20 further may comprise one or more additional sensors for adjusting flow output and pulsatility according to the demand of the patient. Sensors may be incorporated into pump 20 or alternatively or in addition to may be implanted elsewhere in or on the patient. The sensors preferably are in electrical communication with controller 30, and may monitor operational parameters that measure the performance of pump 20 or physiological sensors that measure physiological parameters of the patients such as heart rate or blood pressure. By using one or more physiological sensors, pulsatile flow may be synchronized with a cardiac cycle of the patient by monitoring blood pressure or muscle contractions, for example, and synchronizing the duty cycle according to the sensed output.

Controller 30 may compare physiological sensor measurements to current pump output. If it is determined by analyzing sensor measurements that demand exceeds current output, frequency, amplitude and/or duty cycle may be automatically adjusted to meet current demand. Similarly, the controller may determine that current output exceeds demand and thus alter output by changing frequency, amplitude and/or duty cycle. Alternatively, or in addition to, when it is determined that demand exceeds current output, an alarm may sound from controller 30. Similarly, operational measurements from operational sensors may be compared against predetermined thresholds and where measurements exceed predetermined thresholds or a malfunction is detected, an alarm may sound from controller 30.

Pump 20 is sized and shaped to produce physiological flow rates, pressure gradients and pulsatility at an operating point at which maximum efficiency is achieved. Specially, pump 20 may be sized and shaped to produce physiological flow rates ranging from 2 to 15 liters per minute at pressure gradients lower than a threshold value associated with hemolysis. Also, to mimic a typical physiological pulse of 60 beats per minute, pump 20 may pulse about once per second. To achieve such pulsatility, a duty cycle of 20-50% may be utilized with an "on" or "high" period of 0.2-0.5 seconds and an "off" or "low" period of 0.5-0.8 seconds, for example, where a "high" setting represents an operating point of frequency and amplitude resulting in increased blood flow rates against physiologic pressure, whereas a "low" setting represents an operating point of frequency and amplitude resulting in lower blood flow rates against physiologic pressures. For a given system, maximum efficiency at a specific operating frequency, amplitude and voltage may be achieved while producing a flow rate of 2 to 15 liters per minute at a duty cycle of 20-50% by manipulating one or more of the shape and size of blood flow channels, elastic properties of the suspension rings, mass of the moving parts, membrane geometries, and elastic properties and friction properties of the membrane. In this manner, pump 20 may be designed to produce desirable physiological outputs while continuing to function at optimum operating parameters.

By adjusting the duty cycle, pump 20 may be configured to generate a wide range of output flows at physiological pressure gradients. For example, for an exemplary LVAD system configured to produce 2 to 15 liters per minute at a duty cycle of 20-50%, optimal operating frequency may be 25-70 Hz or even 120 Hz. For this system, flow output may be increased to 10 liters per minute or decreased to 4 liters per minute, for example, by changing only the duty cycle. As duty cycle and frequency operate independent of one another, duty cycle may be manipulated between 0 and 100% while leaving the frequency unaffected.

The pump system described herein, tuned to achieve physiological flow rates, pressure gradients and pulsatility, also avoids hemolysis and platelet activation by applying low to moderate shear forces on the blood, similar to those encountered by blood elements in the normal, non-diseased vascular system. In the embodiment detailed above, delivery channel 100 may be sized and configured to also avoid friction between moving magnetic ring assembly 76, suspension rings 79 and 80, posts 81 and lower housing portion 25 by sizing the channel such that clearances of at least 0.5 mm are maintained between all moving components. Similarly, magnetic ring assembly 76, suspension rings 79 and 80, and posts 81 all may be offset from stator assembly 72 by at least 0.5 mm to avoid friction between the stator assembly and the moving parts.

Figure 15A:
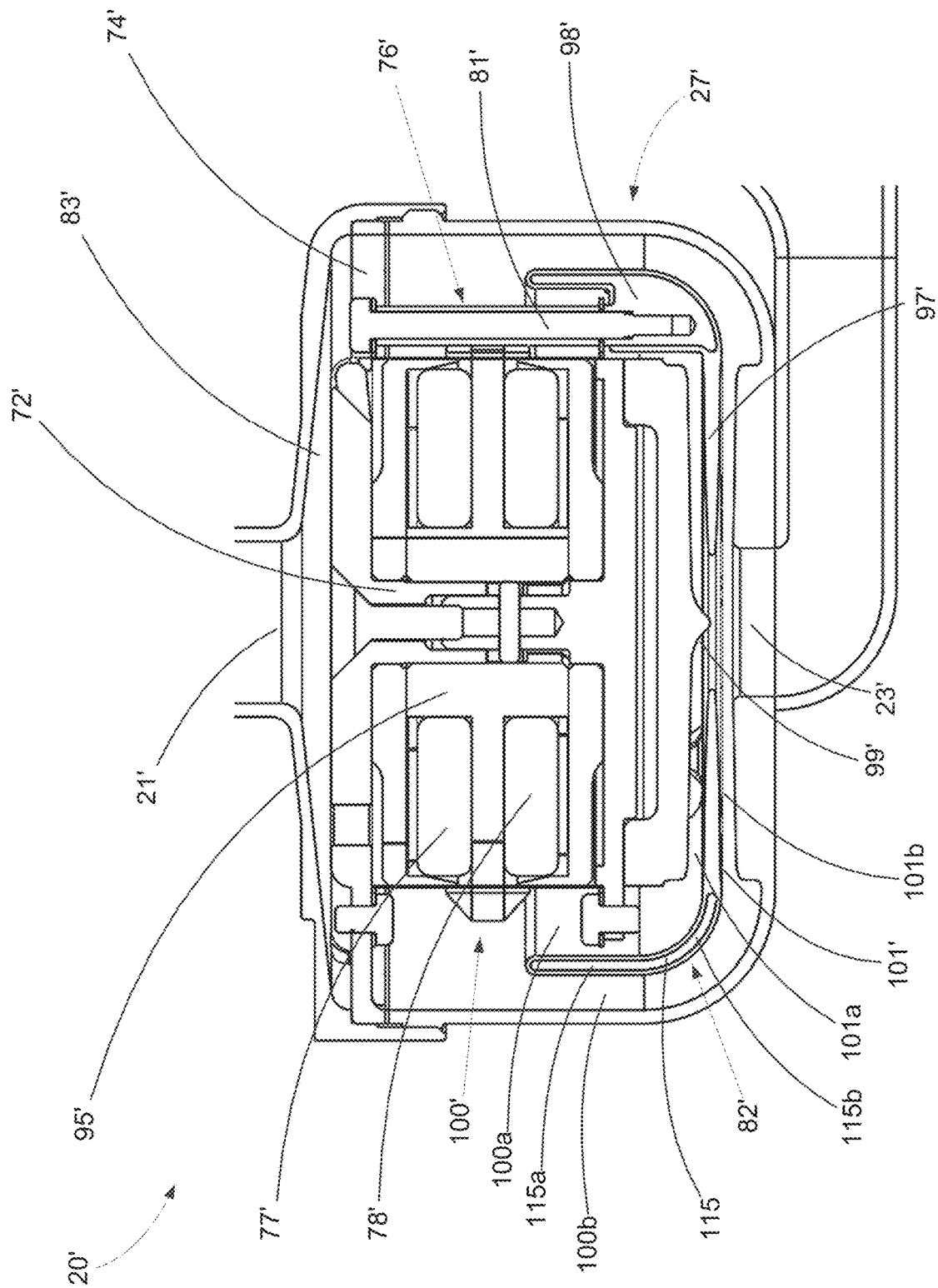
FIG. 15A is a cross-sectional view of an alternative exemplary embodiment of a blood pump of the present invention with improved hydraulic performance for use in the pump system of FIG. 1.
Figure 15B:
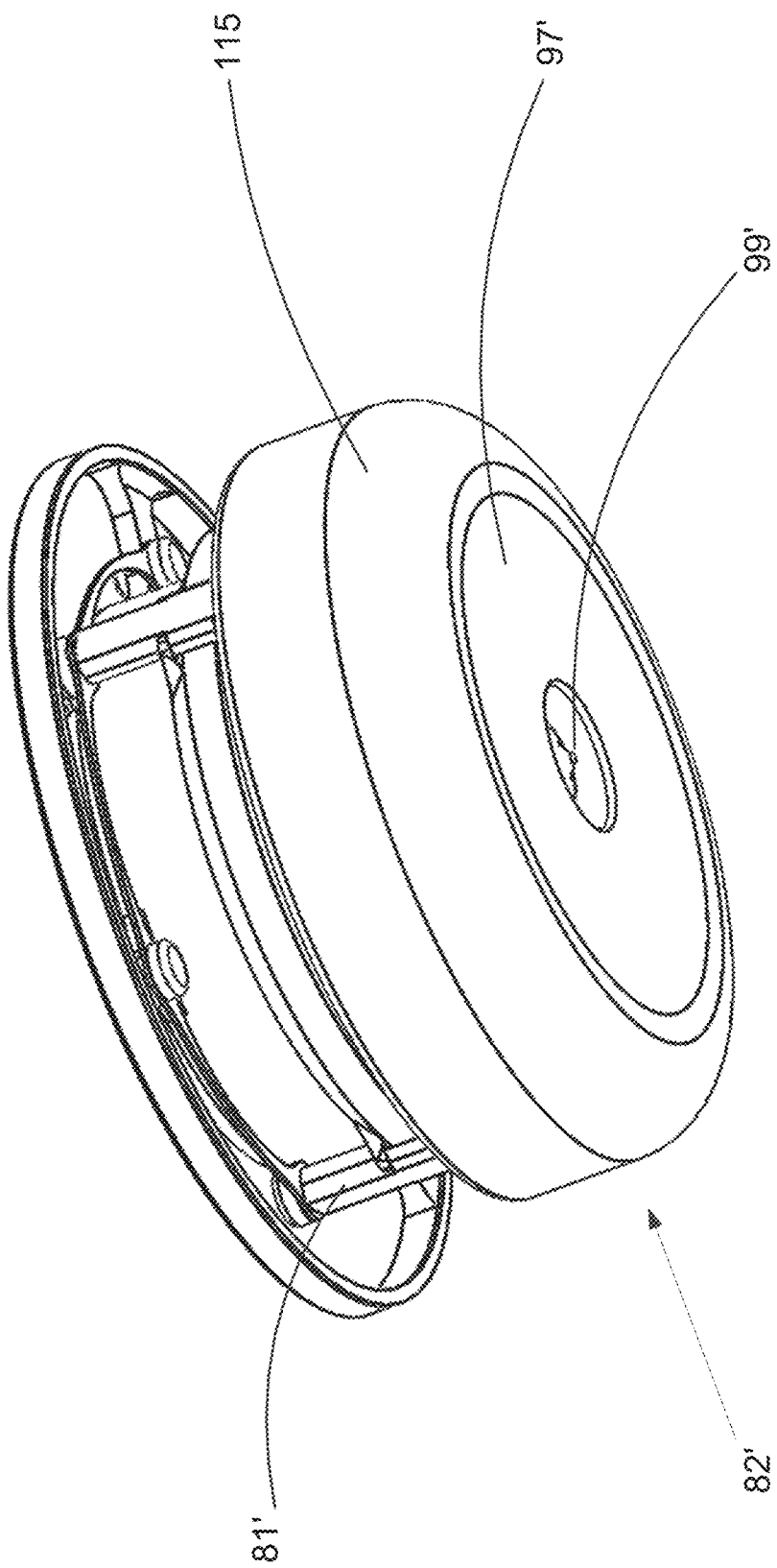
FIG. 15B is a perspective view of the blood pump of FIG. 15A.

Referring now to FIGS. 15A and 15B, an alternative exemplary embodiment of the pump assembly of the present invention is described. Pump 20' is constructed similar to pump 20 described in FIGS. 7, 8, and 12, in which similar components are identified with like-primed numbers. Pump 20' is distinct from pump 20 in that membrane assembly 82' includes skirt 115 coupled to membrane 97'. Skirt illustratively includes first portion 115a and second portion 115b. First portion 115a of skirt 115 extends upward within delivery channel 100' toward inlet 21' in a first direction, e.g., parallel to the longitudinal axis of stator assembly 72' and/or to the central axis of pump housing 27'. Second portion 115b of skirt 115 curves toward outlet 23' such that second portion 115b is coupled to membrane 97' so that membrane 97' is oriented in a second direction, e.g., perpendicular to first portion 115a of skirt 115. For example, skirt 115 may have a J-shaped cross-section, such that first portion 115a forms a cylindrical-shaped ring about stator assembly 72' and second portion 115b has a predetermined radius of curvature which allows blood to flow smoothly from delivery channel 100' across skirt 115 to the outer edge of membrane 97' and into flow channel 101', while reducing stagnation of blood flow. Skirt 115 breaks flow recirculation of blood within delivery channel 100' and improves hydraulic power generated for a given frequency while minimizing blood damage. In addition, the J-shape of skirt 115 around stator assembly 72' may be stiffer than a planar rigid membrane ring, thereby reducing flexing and fatigue, as well as drag as the blood moves across membrane 97'.

Skirt 115 exhibits rigid properties under typical forces experienced during the full range of operation of the present invention and may be made of a biocompatible metal, e.g., titanium. Skirt 115 is preferably impermeable such that blood cannot flow through skirt 115. Post reception sites 98' may be formed into skirt 115 to engage membrane assembly 82' with posts 81'. Alternatively, posts 81' may be attached to skirt 115 in any other way which directly translates the motion of magnetic ring assembly 76' to skirt 115.

As magnetic ring assembly 76' moves up and down, the movement is rigidly translated by posts 81' to J-shape of skirt 115 of membrane assembly 82'. Given the rigidity of the posts, when magnetic ring assembly 76' travels a certain distance upward or downward, membrane assembly 82' may travel the same distance. For example, when magnetic ring assembly 76' travels 2 mm from a position near first electromagnetic coil 77' to a position near second electromagnetic coil 78', membrane assembly 82' may also travel 2 mm in the same direction. Similarly, the frequency at which magnetic ring assembly 76' traverses the space between the first and second electromagnetic coils may be the same frequency at which membrane assembly 82' travels the same distance.

Skirt 115 may be affixed to membrane 97' and hold membrane 97' in tension. Membrane 97' may be molded directly onto skirt 115 or may be affixed to skirt 115 in any way that holds membrane 97' uniformly in tension along its circumference. For example, skirt 115 may be coated with the same material used to form membrane 97' and the coating on skirt 115 may be integrally formed with membrane 97'.

Blood may enter pump 20' from the left ventricle through inlet cannula 21' and flow downward along the pump assembly into delivery channel 100'. As the blood moves down tapered section 83', it is directed through gap 74' and into a vertical portion of delivery channel 100' in the area between pump housing 27' and actuator assembly 95'. As shown in FIG. 15A, skirt 115 divides delivery channel 100' into upper delivery channel 100a and lower delivery channel 100b such that blood flow through delivery channel 100' is divided into flow channel 101a via upper delivery channel 100a and flow channel 101b via lower delivery channel 100b, wherein flow channels 101a and 101b are separated by membrane 97'. As will be understood by one of ordinary skill in the art, the volume of blood flow through each of delivery channels 100a and 100b may depend on the diameter of first portion 115a of skirt 115. For example, the larger the diameter of first portion 115a of skirt 115, the larger the volume of delivery channel 100a and the smaller the volume of delivery channel 100b. The ratio of the volume of delivery channel 100a to the volume of delivery channel 100b may be, for example, 1:1, 1:2, 1:3, 1:4, 2:1, 3:1, 4:1, etc., depending on the amount of desired blood flow on each surface of membrane 97'.

Figure 16B:
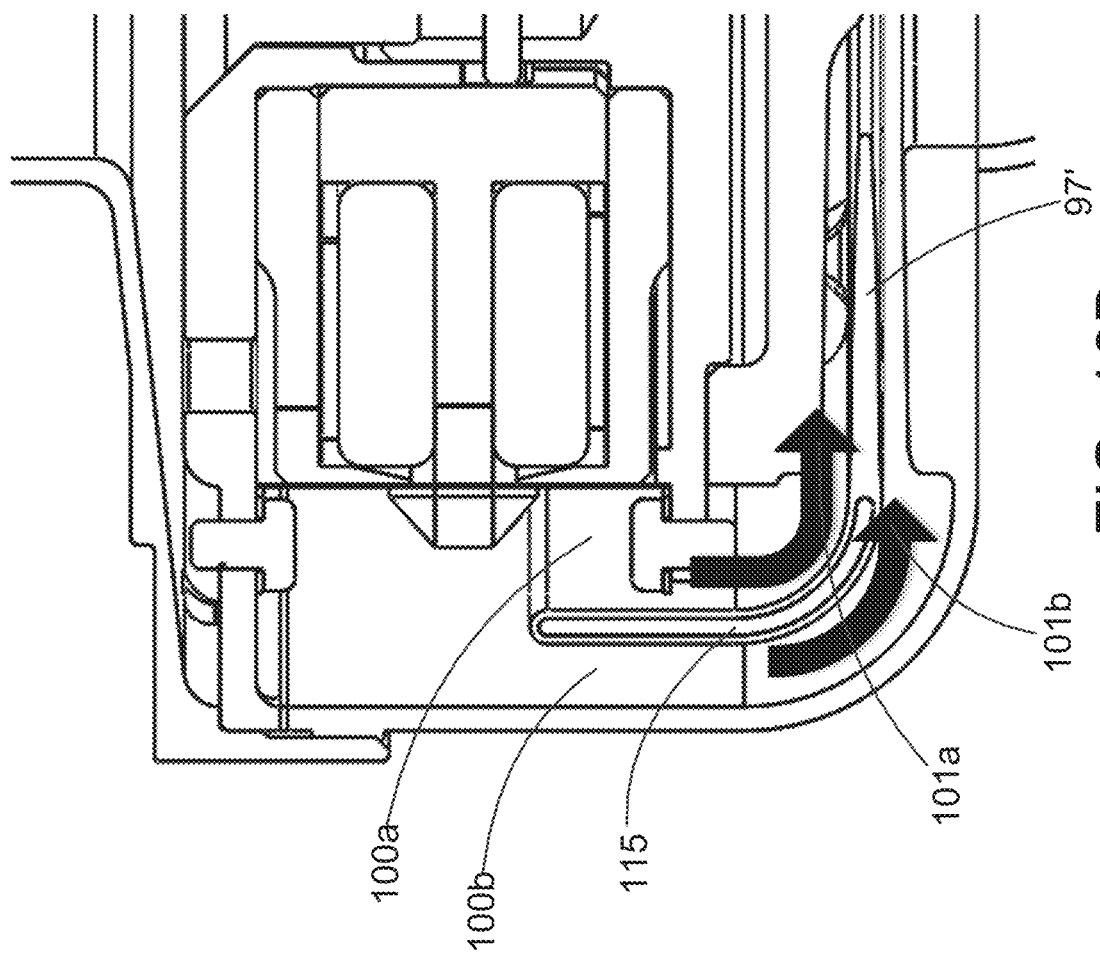
FIG. 16B illustrates blood flow using a pump assembly with a skirt in accordance with one aspect of the present invention.
Figure 16A:
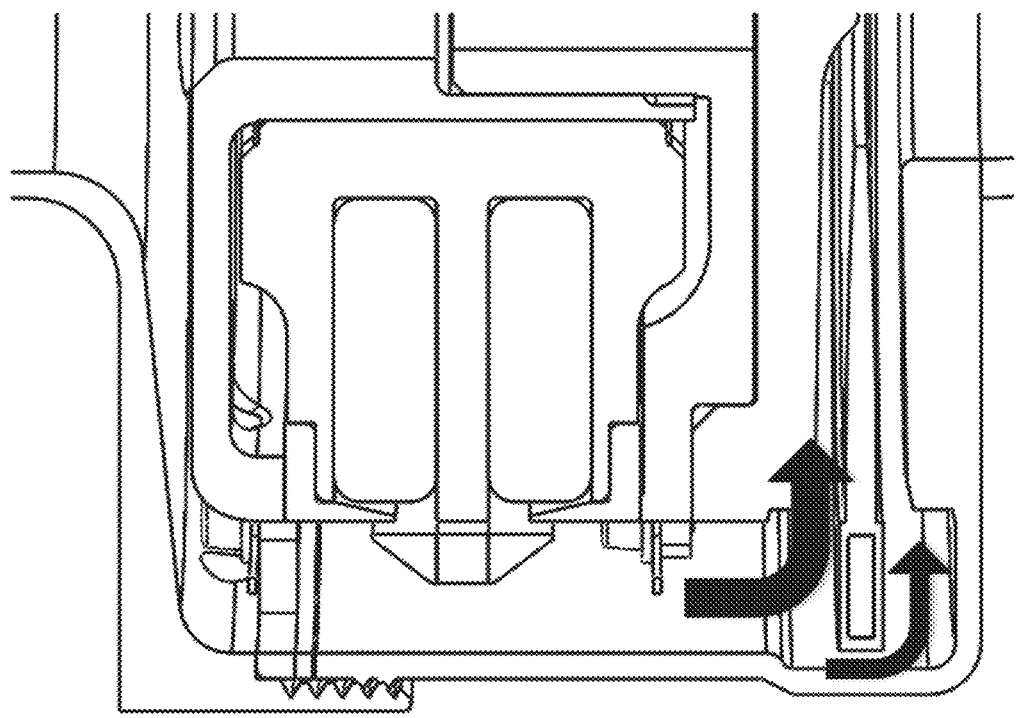

By directing blood from inlet cannula 21' across skirt 115 within delivery channel 100', blood flow is divided into delivery channel 100a and 100b and to flow channels 101a and 101b, respectively, such that blood flows across the upper and lower surfaces of membrane 97' of membrane assembly 82'. For example, as shown in FIG. 16A, blood flow through a pump having a planar rigid membrane ring spaced apart a relatively small distance from the pump housing may allow unrestricted blood flow across the upper surface of the flexible membrane while restricting blood flow across the lower surface of the flexible membrane. Whereas, as depicted in FIGS. 16B and 16C, blood flow through a pump having a J-shaped skirt or integrated portion may be distributed across both the upper and lower sides of the flexible membrane at a desired ratio.

Second portion 115b of skirt 115 curves toward outlet 23' such that second portion 115b is coupled to membrane 97' so that membrane 97' is oriented in a second direction, e.g., perpendicular to first portion 115a of skirt 115. For example, skirt 115 may have a J-shaped cross-section, such that first portion 115a forms a cylindrical-shaped ring about stator assembly 72' and second portion 115b has a predetermined radius of curvature which allows blood to flow smoothly from delivery channel 100' across skirt 115 to the outer edge of membrane 97' and into flow channel 101', while reducing stagnation of blood flow. Skirt 115 breaks flow recirculation of blood within delivery channel 100' and improves hydraulic power generated for a given frequency while minimizing blood damage. In addition, the J-shape of skirt 115 around stator assembly 72' may be stiffer than a planar rigid membrane ring, thereby reducing flexing and fatigue, as well as drag as the blood moves across membrane 97'.

Referring back to FIG. 15A, by actuating electromagnetic coils 77' and 78', membrane 97' may be undulated within flow channels 101a and 101b to induce wavelike formations in membrane 97' that move from the edge of membrane 97' towards circular aperture 99'. Accordingly, when blood is delivered to membrane assembly 82' from delivery channel 100', it may be propelled radially along both the upper and lower surfaces of membrane 97' towards circular aperture 99', and from there out of outlet 23'. The distribution of blood flow across the upper and lower surfaces of membrane 97' reduces recirculation of blood within delivery channel 101', and reduces repeated exposure of blood to high shear stress areas, which results in remarkably improved hydraulic performance of pump 20'.

Figure 16C:
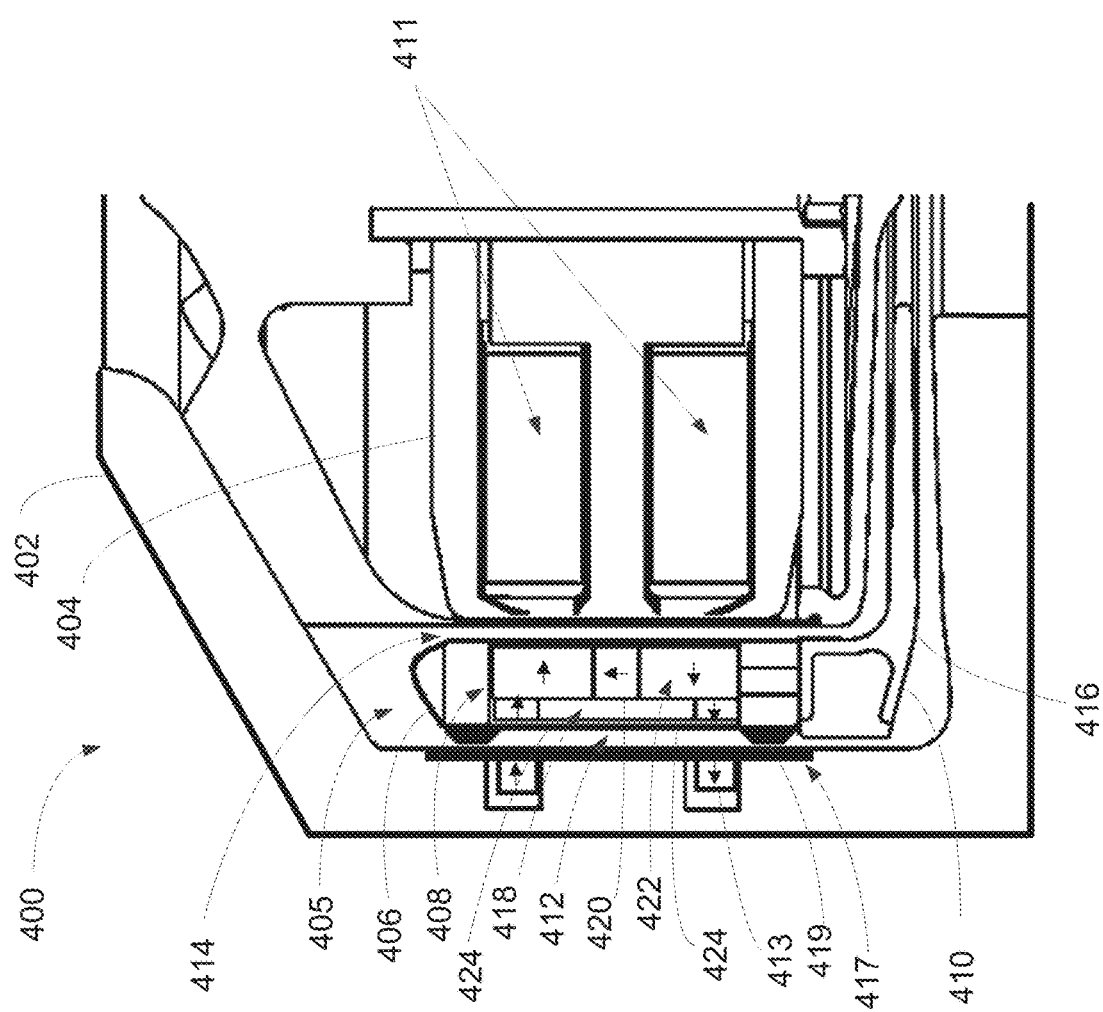

Referring now to FIG. 16C, pump 400 is illustrated which is similar to pump 20 and includes pump housing 402, integrated assembly 406, membrane 416 and actuator assembly 404 which may be the same or similar to actuator assembly 95. Integrated assembly 406 may be disposed around actuator assembly 404 and may include magnetic assembly 408 and transition portion 410. Magnetic assembly 408 may be similar to magnetic ring assembly 76 and/or may include one or more magnet 422 and/or iron portion 420. It is understood that magnetic assembly 408 may include a Halbach array. Integrated assembly 406 may further include outer cover 418 to permit hermetic sealing of the components in integrated assembly 406 (e.g., magnetic assembly 408) as well as magnet backing 424 to facilitate magnet alignment and assembly. Integrated assembly 406 may also include one or more bearing portions 419.

Integrated assembly 406 may be similar to skirt 115 in function, except that integrated assembly 406 may incorporate magnetic assembly 408. Integrated assembly 406 may extend upward within delivery channel 405 and further include transition portion 410 that extends toward membrane 416, which may be the same as or similar to membrane 97. Transition portion 410 may attach the integrated assembly 406 to membrane 416. Integrated assembly 406 may define a first blood channel 412 between integrated assembly 406 and pump housing 402 and may further define a second blood channel between integrated assembly 406 and actuator assembly 404. Similar to skirt 115, integrated assembly 406 may divert blood into first blood channel 412 and second blood channel 414 and ultimately to membrane 416.

Pump housing 402 may include one or more magnets 413 and one or more bearing portions 417. Bearing portion 417 may be in fluid communication (e.g., via blood in first blood channel 412) with bearing portion 419 and together may form a bearing that resists radial movement of moving assembly 406. Bearing portions 417 and 419 may be comprised of biocompatible materials, such as ceramics, alumina, zirconia, or zirconia-toughened alumina, or engineered plastics, such as poly-ether-ether-ketone (PEEK) and Delrin, or metallic alloys coated with tribologic coatings, such as titanium coated with titanium nitride (TiN) or zirconium nitride (ZrN). Magnets 413 and magnetic assembly 408 may interact to resist axial movement and cause moving assembly to return to a neutral position axially.

One or more magnets of magnetic assembly 408 may be enlarged to increase second blood channel 414, while maintaining attraction between one or more coils (e.g., coils 411) of actuator assembly 404 and magnetic assembly 408. The increased second blood channel 414 may reduce the risk of shear-induced damage to the blood and/or thermal injury. As shown in FIG. 16C, pump 400 may having a single moving assembly (e.g., integrated assembly 406) in addition to membrane 416.

Figure 16D:
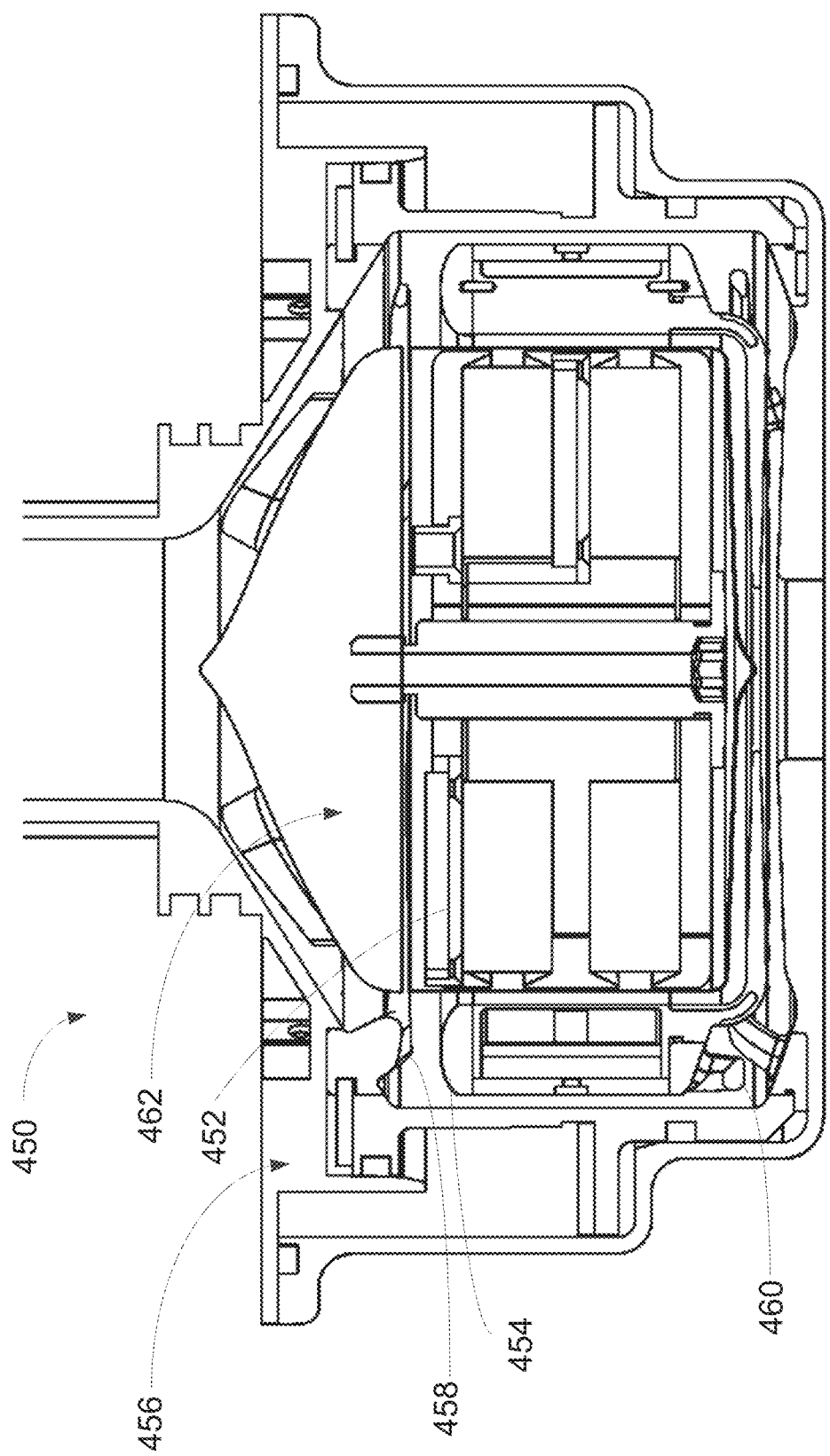
FIG. 16D illustrates a blood pump with an integrated portion incorporating a magnetic assembly and featuring mechanical springs.

Referring now to FIG. 16D, pump 450 including inlet spring 458 and outlet spring 460 is illustrated. Pump 450 may be similar to pump 400 and may include actuator assembly 452, which may be similar to actuator assembly 404, pump housing 456, which may be similar to pump housing 402, and integrated assembly 454, which may be similar to integrated assembly 406. As shown in FIG. 16, integrated assembly 454 may be coupled to inlet spring 458 and outlet spring 460. Inlet spring 456 and outlet spring 460 may be coupled at one end to integrated assembly 454 and at the other end to pump housing 456. Inlet spring 458 and outlet spring 460 may be monobloc springs, for example, or any other well-known springs. Inlet spring 458 and outlet spring 460, may be comprised of biocompatible metals, such as stainless steel, titanium, or cobalt chromium, for example, and/or may be processed by methods to remove surface defects or cold work the materials to increase durability and hemocompatibility. The inlet spring 458 and/or outlet spring 460 may be made by cutting shapes out of the flat sheet of the biocompatible metal. Alternatively, the inlet spring 458 and/or the outlet spring 460 may be machined out of a solid block of material, therefore allowing for a more contoured and/or three dimensional design. In preferred embodiments, the solid block of material is stainless steel or titanium. Inlet spring 458 and outlet spring 460 may resist both radial and axial movement of moving assembly 456 and may cause moving assembly 456 to return to a neutral position. It is understood that either the inlet spring 458 and/or outlet spring 460 may be optional (e.g., the pump 450 may include inlet spring 458 and/or outlet spring 460). As also shown in FIG. 16D, dampening structure 462 may be coupled to and/or extend from actuator assembly 452 and may facilitate in dampening vibration of pump 450 (e.g., caused by moving assembly 454). Dampening structure 462 may be comprised of polymer materials, such as biocompatible polyurethane, for example, with Shore Hardness values from 20 to 80A. It is understood that inlet spring 458 and outlet spring 460 may be the same or similar to suspension springs. Alternatively, an active dampening structure may be used. An active dampening structure may include or otherwise employ one or more moving mass or tuned mass damper for reducing vibration. In one example, the active dampening structure may be located on the outside surface of the pump, such as vibration dampening assembly 523 in FIG. 17.

Referring now to FIG. 17, pump 500 with an encapsulation assembly is illustrated. Pump 500 is similar to pump 20 described above with respect to FIGS. 7, 8, and 12. For example, pump 500 may include inlet cannula 501, which may be similar to inlet cannula 21, outlet cannula 502, which may be similar to outlet cannula 22, upper housing portion 515 which may be similar to upper housing portion 24, and lower housing portion 517, which may be similar to lower housing portion 25. Upper housing portion 515 may be coupled to lower housing portion 517 as well as outlet cannula 502. Lower housing portion 517 may be coupled outlet cannula 502. Upper housing portion 515 and/or inlet cannula 501 may be coupled to stator assembly 511, which may include upper stator portion 521 and lower stator portion 520 as well as core stator portion 545. Core stator portion 545 may be coupled to both upper stator portion 521 and lower stator portion 520 and may support electromagnetic coils (e.g. first electromagnetic coil 504 and second electronic magnetic coil 505).

As shown in FIG. 17, upper stator portion 521 and lower stator portion 520 may form stator assembly 511 and may be designed to house and secure electromagnetic assembly 503, which may be similar in structure and/or function to electromagnetic assembly 91. For example, electromagnetic assembly 503 may include first electromagnetic coil 504 and second electronic magnetic coil 505. It is understood that electromagnetic assembly 503 may be any electromagnetic assembly described herein and/or may include greater than or fewer than two electromagnetic coils. Electromagnetic assembly 503 together with stator assembly 511 form an actuator assembly.

Magnetic assembly 513, which may be similar in structure and function to magnetic ring assembly 76, may be suspended around electromagnetic assembly 503. For example, magnetic assembly 513 may be the magnetic assembly illustrated in FIG. 19. Magnetic assembly 513 may also be coupled to first spring 534, which may be similar to first suspension spring 79, and second suspension spring 535, which may be similar to second suspension spring 80. First suspension spring 534 may also be coupled to upper stator portion 521 and second suspension spring 535 may also be coupled to lower stator portion 520. First suspension spring 534 and second suspension spring 535 may bias magnetic assembly 513 towards a neutral position between first suspension spring 534 and second suspension spring 535 and/or may offset magnetic assembly 513 from actuator assembly 546. It is further understood that first suspension spring 534 and second suspension spring 535 may resist twist and/or tilt movement of magnetic assembly 513 and/or is provide a restoring force to return the magnet assembly 513 toward a center position. Specifically, first suspension spring 534 and second suspension spring 535 may assist in keeping the axial centerline of the stator and the magnetic ring parallel.

Upper stator portion 521 may be further coupled to top encapsulator 532 and lower stator portion 520 may be coupled to bottom encapsulator 531. Top encapsulator 532 and bottom encapsulator 531 may each be coupled to magnetic assembly 513. Top encapsulator 532 and bottom encapsulator 531 may be elastic membranes made from any well-known elastic or expandable material and/or structure. For example, top encapsulator 532 and/or bottom encapsulator 531 may be made from any well-known elastic and/or thermoplastic material and/or visco-elastic material (e.g., silicone) and/or any ridged material forming a structure designed to expand (e.g., a metallic structure having bellows). Top encapsulator 532 and bottom encapsulator 531 may exert a spring force on magnetic assembly 513 due to the elastic properties of each. Top encapsulator 532 and first suspension spring 534 may work together to collectively apply a spring force to magnetic assembly 513 and similarly bottom encapsulator 531 and second suspension spring 535 may work together to apply a spring force to magnetic assembly 513. First suspension spring 534 and/or second suspension spring 535 may be sized and otherwise designed to accommodate the spring force of top encapsulator 532 and/or bottom encapsulator 531. For example, first suspension spring 534 and/or second suspension spring 535 may be sized and otherwise shaped to achieve a desired neutral position of magnetic assembly 513 based at least in part on the elastic properties of top encapsulator 532 and bottom encapsulator 531.

Magnetic assembly 513, top encapsulator 532 and bottom encapsulator 531, and stator assembly 511 may collectively form encapsulation assembly 525 which may form a continuous surface thereby encapsulating actuator assembly 546, first suspension spring 534 and second suspension spring 535. In this manner, blood flow channel 537 may be defined between magnetic assembly 513, top encapsulator 532 and bottom encapsulator 531, and stator assembly 511 (i.e., the encapsulation assembly 525) on one side, and an interior surface of upper housing portion 515 and lower housing portion lower housing portion 517 on the other side.

Encapsulation assembly 525 may present a number of advantages. For example, because actuator assembly 546, first suspension spring 534 and second suspension spring 535 are encapsulated, blood is prevented from interacting with actuator assembly 546, first suspension spring 534 and second suspension spring 535 and therefore such encapsulation may prevent damage to the blood (e.g., hemolysis) that may occur when these components interact with the blood and magnetic assembly 513 during operation of pump 500. Moreover, the blood path may be smoother from a hydrodynamic standpoint with fewer areas with stagnation and turbulent flow thereby reducing the risk for thrombus formation. The blood path may be optimized to minimize blood exposure to shear conditions which can cause damage to blood elements, such as the adhesion protein, von Willebrand Factor.

Membrane assembly 538 may be coupled to magnetic assembly 513 such that membrane assembly 538 moves together with magnetic assembly 513. Membrane assembly 538 may include skirt 550 and membrane 507, which may be similar to skirt 115 and membrane 97', respectively, as described above with respect to FIG. 16B. Membrane 507 may be circular in shape and may include a circular aperture in the center. For example, skirt 550 may be disposed around encapsulation assembly 525 and may extend within delivery channel 537 in a vertical direction and may curve toward membrane 507, which may be oriented in a horizontal direction. For example, skirt 550 may have a J-shaped cross-section, such that a portion of skirt 550 forms a cylindrical-shaped structure about stator assembly and may have a predetermined radius of curvature which allows blood to flow smoothly from delivery channel 537 across skirt 550 to membrane 507, reducing stagnation of blood flow.

Skirt 550 may reduce or eliminate flow recirculation of blood within delivery channel 537 and improve hydraulic power generated for a given frequency while minimizing blood damage. In addition, the J-shape of skirt 550 may be stiffer than membrane 507, thereby reducing flexing and fatigue, as well as drag as the blood moves across membrane 507. Membrane assembly 538 may be rigidly coupled to magnetic assembly 513 via a plurality of rigid pins and/or via surface contact that may be welded. As magnetic assembly 513 moves up and down (e.g. reciprocates), so too will skirt 550, thereby causing wavelike undulations in membrane 507 that propels blood over and under membrane 507 splitting blood flow path 537 include blood flow paths 506 towards outlet cannula 502 of pump 500.

Upper housing portion 515 may include vibration dampening assembly 523 which may be designed to dampen vibration of pump 500 as magnetic assembly 513 reciprocates in operation. For example, vibration dampening assembly 523 may be a tuned mass damper, wherein a mass is tuned to oscillate in a 180 degree phase to the primary motion of the actuator. Vibration dampening assembly 523 may include mass 540 suspended by one or more vibration springs 541. For example, mass 540 may be an annular mass. Vibration dampening assembly 523 may be disposed around and/or positioned on an outer surface of upper housing portion 515, or otherwise incorporated into upper housing portion 515. Mass 540 and vibration spring 541 may be sized and shaped to reduce vibration levels of pump 500 due to magnetic assembly 513 reciprocating.

Figure 18:
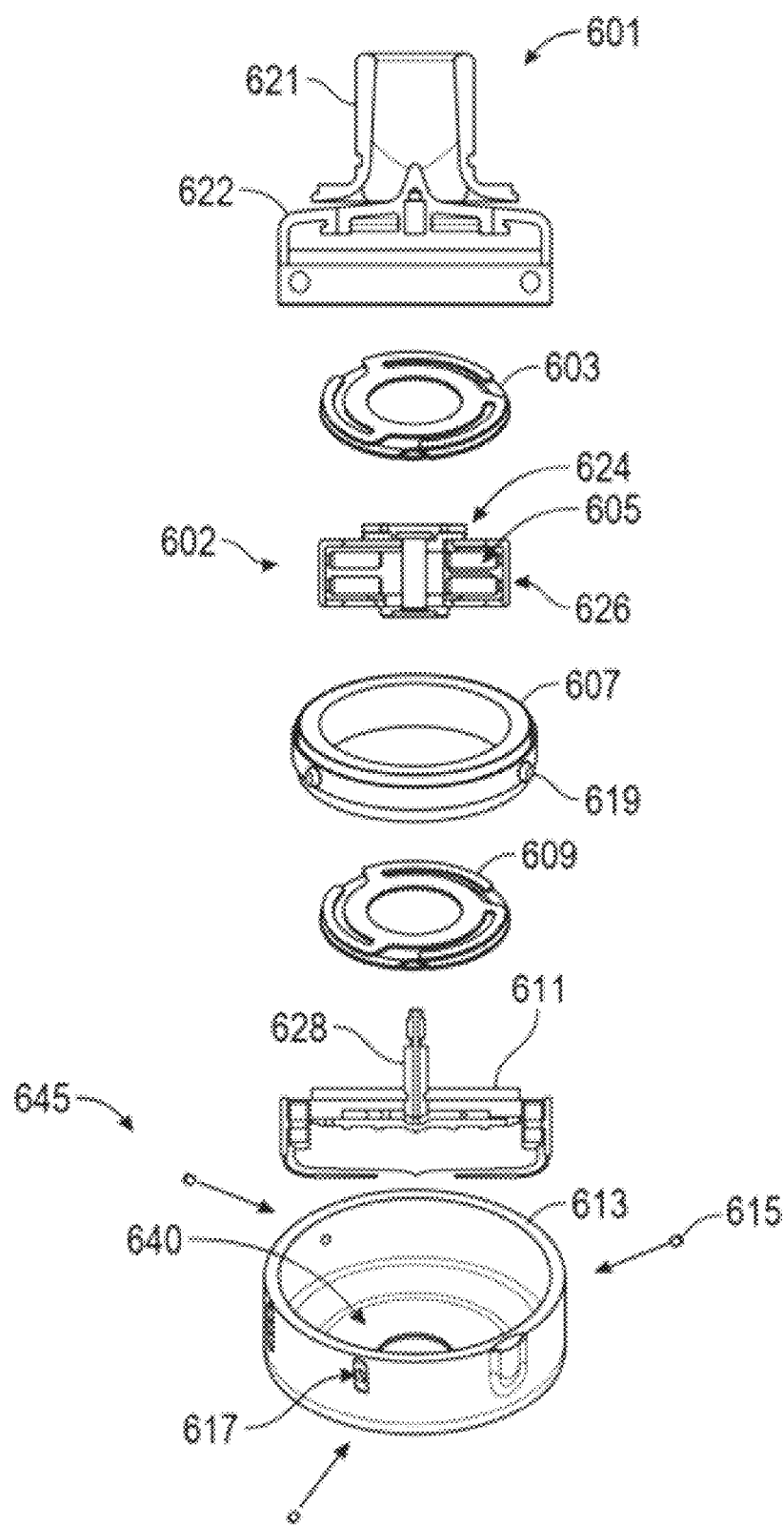
FIG. 18 is an exploded view of a blood pump with an encapsulated actuator assembly.

Referring now to FIG. 18, an exploded view of the actuator assembly, magnetic assembly, and membrane assembly is illustrated. As shown in FIG. 18, inlet block 601 may include inlet cannula 621, which may be similar to inlet cannula 501 of FIG. 17, as well as upper stator portion 622, which may be similar to upper stator portion 521 of FIG. 17. First suspension spring 603, which may be similar to first suspension spring 534 of FIG. 17, may be coupled to upper stator portion 622.

Core assembly 602 may be coupled to upper stator portion 622 and may be disposed below first suspension spring 603. Core assembly 602 may include electromagnetic assembly 605, which may be similar to actuator assembly 546 of FIG. 17, and core stator portion 624, which may be the same as core stator portion 545 of FIG. 17. Core stator portion 624 may support electromagnetic assembly 605. Core assembly 602 may include encapsulation portion 626, which may be a flexible membrane (e.g., silicone) that may cover all or a portion of electromagnetic assembly 605 and/or core stator portion 545. Magnetic assembly 607, which may be similar to magnetic assembly 513 of FIG. 17, may be disposed around core assembly 602 and may be coupled to inlet block 601 via first suspension spring 534. Magnetic assembly 607 may include pin receiving portion 619 sized and designed to receive and engage pin 615.

Second suspension spring 609, which may be similar to second suspension spring 535 of FIG. 17, may also be coupled to magnetic assembly 607 and also coupled to lower stator portion 611, which may similar to lower stator portion 520 of FIG. 17. In this manner, magnetic assembly 607 may be concentrically positioned between the first suspension spring 603 and second suspension spring 609 such that magnetic assembly 607 may oscillate between first suspension spring 603 and second suspension spring 609. First suspension spring 603 and second suspension spring 609 may be further coupled to core assembly 602. Lower stator portion 611 may further include protrusion 628, which may extend upward with respect to lower stator portion 611. For example, protrusion 628 may extend through core stator portion 624 and engage upper stator portion 622 to couple lower stator portion 611 and core stator portion 624 to upper stator portion 622. In one example, the engagement between protrusion 628 and upper stator portion 622 may be a threaded engagement.

Membrane assembly 645 may include skirt 613 and membrane 640. Skirt 613 may be similar to skirt 550 of FIG. 17 and membrane 640 may be similar to membrane 507 of FIG. 17. Skirt 613 may further include a plurality of pin receiving portions 617 that may be apertures that extend through skirt 613 and may be sized and shaped to receive pins 615. Pins 615 may be any type of well-known pin that may extend through skirt 613 and couple skirt 613 to magnetic assembly 607. In this manner, membrane assembly 645 may be rigidly coupled to magnetic assembly 607. It is understood that magnetic assembly 607 may alternatively be coupled to skirt 613 using any other well-known coupling technique (e.g., adhesive, threaded engagement, etc.)

Figure 19:
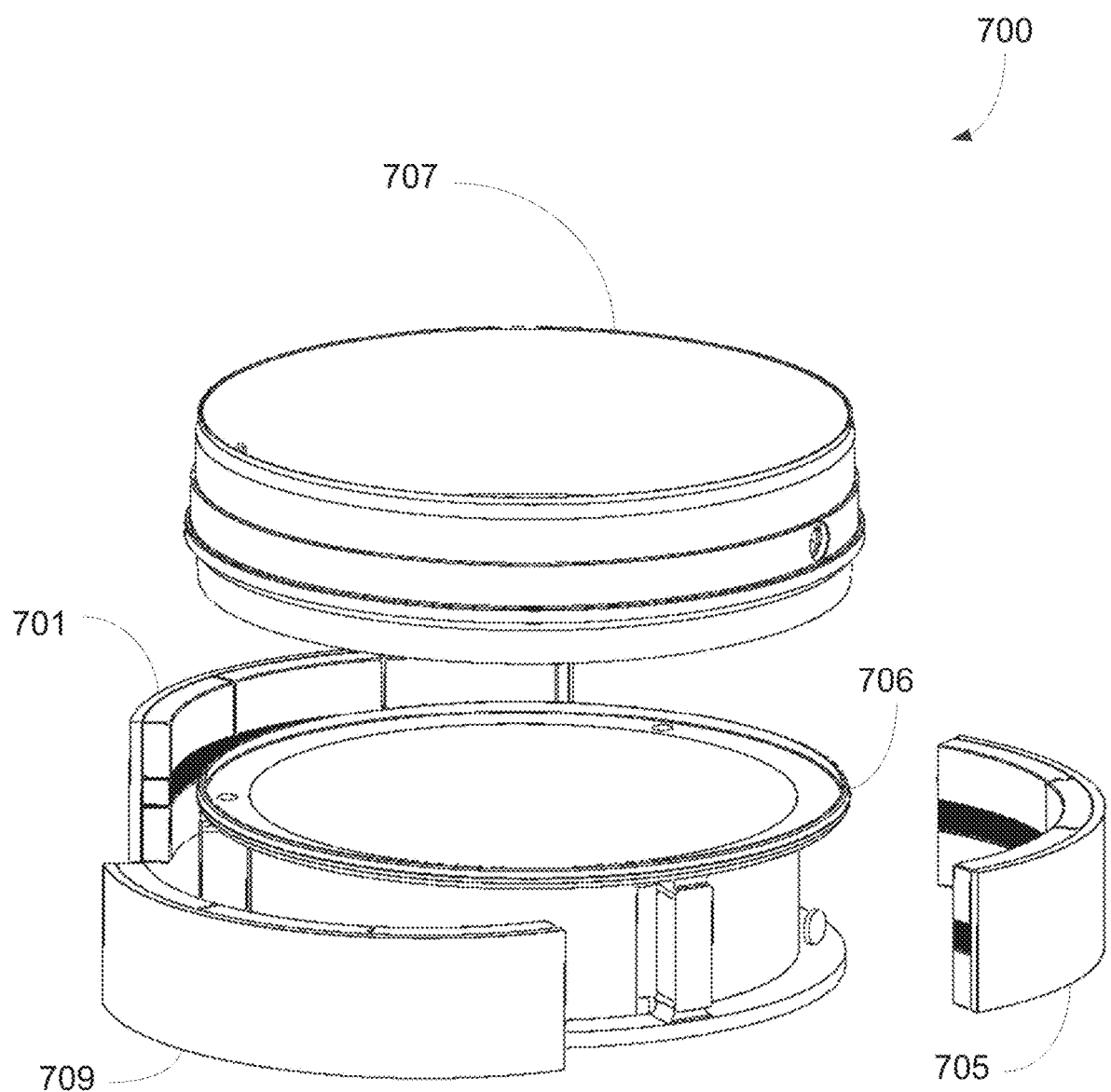
FIG. 19 is an exploded view of a moving magnet assembly.

Referring now to FIG. 19, magnetic ring assembly 700 is illustrated. As shown in FIG. 19, magnetic ring assembly 700 may include magnet 701, magnet 705 and magnet 709 which each may include one or more magnet portions that form a ring and/or have a general radius of curvature. It is understood that magnet portions 701, 705 and 709 may include one or more magnet and/or iron portions (e.g. iron cobalt). In embodiments, the magnetic portions 701, 705, and 709 are iron cobalt. In embodiments, magnetic ring assembly 700 may include three magnets of iron, neon, and/or boron with a back iron cover of iron-cobalt, for example. It is further understood that magnetic portions 701, 705 and/or 709 may be or include a Halbach array. Magnetic ring assembly 700 may further include inner housing 706 that may house or otherwise support moving magnet portions 701, 705 and 709. Outer housing 707 may be disposed over inner housing 706 and magnet portions 701, 705 and 709 and may couple to inner housing 706 to secure and seal magnet portions 701, 705 and 709 to inner housing 706. While three magnet portions 701, 705, and 709 are illustrated in FIG. 19, it is understood that greater or few magnet portions could be included in magnet ring assembly 700. It is understood that magnetic ring assembly 700 may include magnetic segments such as magnet portions 701, 705 and 709 arranged in a series. Alternatively, magnetic ring assembly 700 may include a single continuous cylindrical magnet or a series of magnets.

FIGS. 20A-20C, illustrate pump 800, encapsulation assembly 850 and membrane assembly 817. Referring now to FIG. 20A, encapsulation assembly 850 may be the same as encapsulation assembly 525 of FIG. 17. Specifically, encapsulation assembly 850 may include upper stator assembly 801, top encapsulator 815, magnetic assembly 805, bottom encapsulator 816, and lower stator assembly 803, which may be similar to upper stator portion 521, top encapsulator 519, magnetic assembly 513, bottom encapsulator 521, and lower stator portion 520 of FIG. 17, respectively. Upper stator assembly 801 may be coupled to inlet cannula 855. Magnetic assembly 805 may include pin receiving portions 821.

As shown in FIG. 20A, magnetic assembly 805 may be positioned between and coupled to top encapsulator 815 and bottom encapsulator 816. Top encapsulator 815 may engage upper stator portion 801. Encapsulation assembly 850 may be axially and concentrically aligned with membrane assembly 817 which may be similar to membrane assembly 538 of FIG. 17. For example, membrane assembly 817 may include skirt 807 and membrane 818, which may be similar to skirt 550 and membrane 507 of FIG. 17.

FIG. 20B illustrates how the membrane assembly 817 may be concentrically positioned around and offset from magnetic ring assembly 805. As illustrated in FIG. 20B, membrane assembly 817 may be rigidly coupled to magnetic ring assembly 805 via pins 811 that may extend through membrane assembly 817 and engage magnetic assembly 805. Referring now to FIG. 20C, a connection between membrane assembly 817 and magnetic assembly 805 is illustrated. As shown in FIG. 20C, membrane assembly 817 may include aperture 820 through which pin 811 may be inserted to engage with pin receiving portion 821 of magnetic assembly 805 sized and designed to receive pin 811.

Figure 21A:
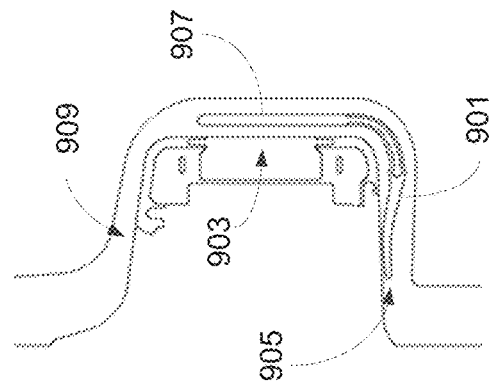
FIGS. 21A-21C are cross-sectional views showing movement of the membrane assembly.
Figure 21B:
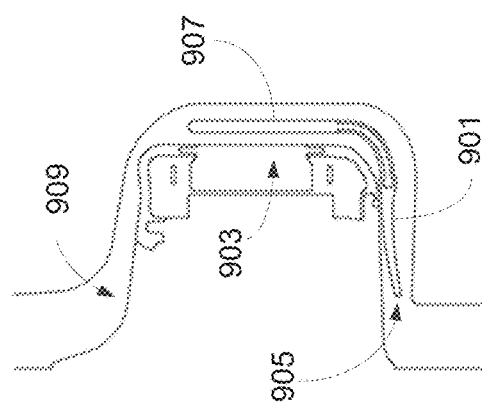
Figure 21C:
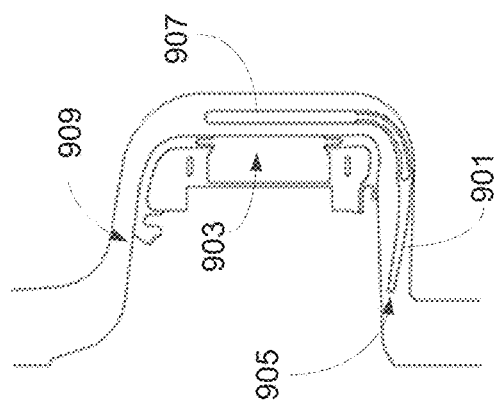

Referring now to FIGS. 21A-21C, movement of membrane 901 in operation of the pump are illustrated. As shown in FIG. 21A, magnetic assembly 903, which may be similar to magnetic assembly 513 of FIG. 17, has moved to an upper most position with respect stator assembly 909, which may be similar to stator assembly 511. As a result, membrane assembly 907, which may be similar to membrane assembly 538, may too move upward, causing membrane 901, which may be similar to membrane 507, to move upward. However, freestanding portion 905 of membrane 905 may remain at a lower position as membrane assembly 907 moves upward. As depicted in FIG. 21B and FIG. 21C, membrane assembly 907 may move downward to a second and third position, respectively, in which the portion of membrane 901 freestanding end 901 rises while membrane assembly 907 lowers. In this manner, a wave-like undulation may be generated toward the free standing end 905 which propels blood to free standing end 905. This process repeats and membrane 901 moves back upward to the first position as shown in FIG. 21A, before again moving to the second and third positions as shown in FIGS. 21B and 21C.

Figure 22B:
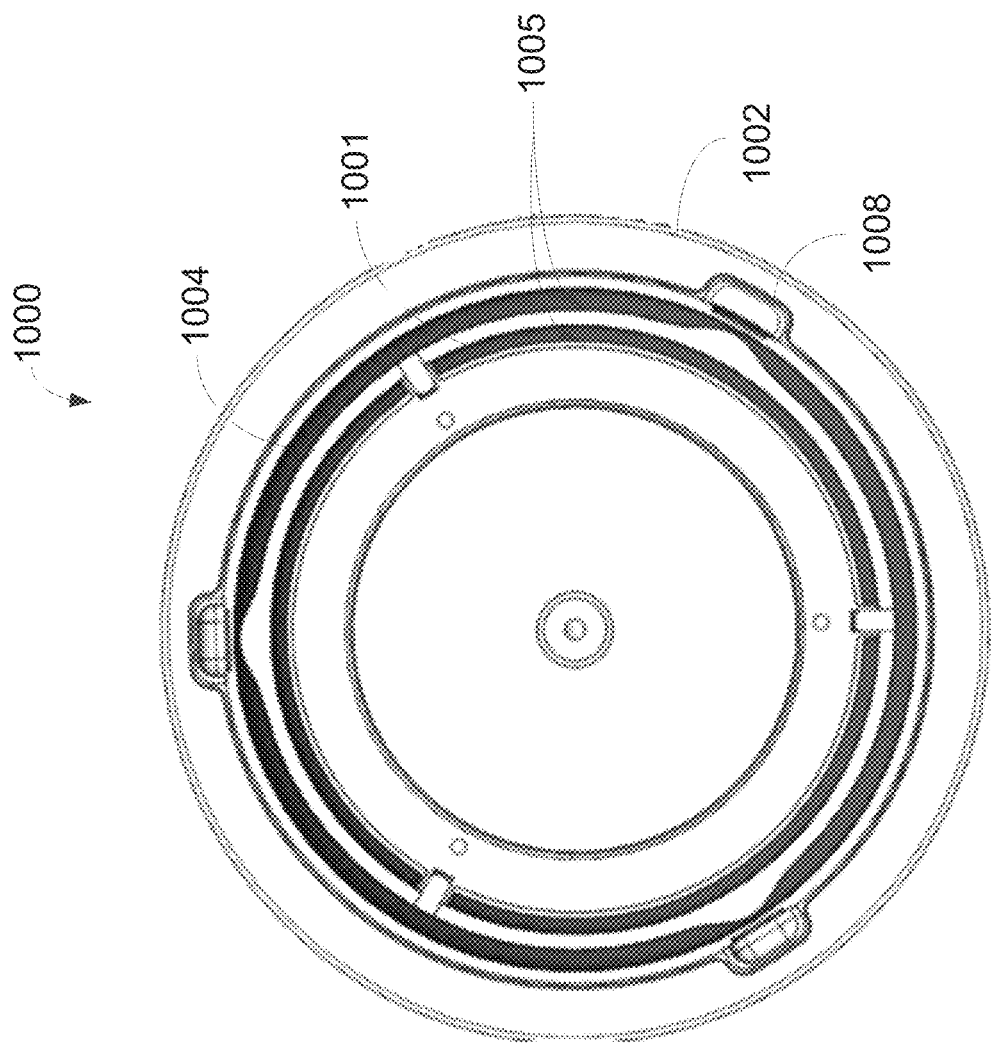
FIG. 22B is a top perspective view of a blood pump including an encapsulated actuator assembly showing surfaces in contact with blood.
Figure 22A:
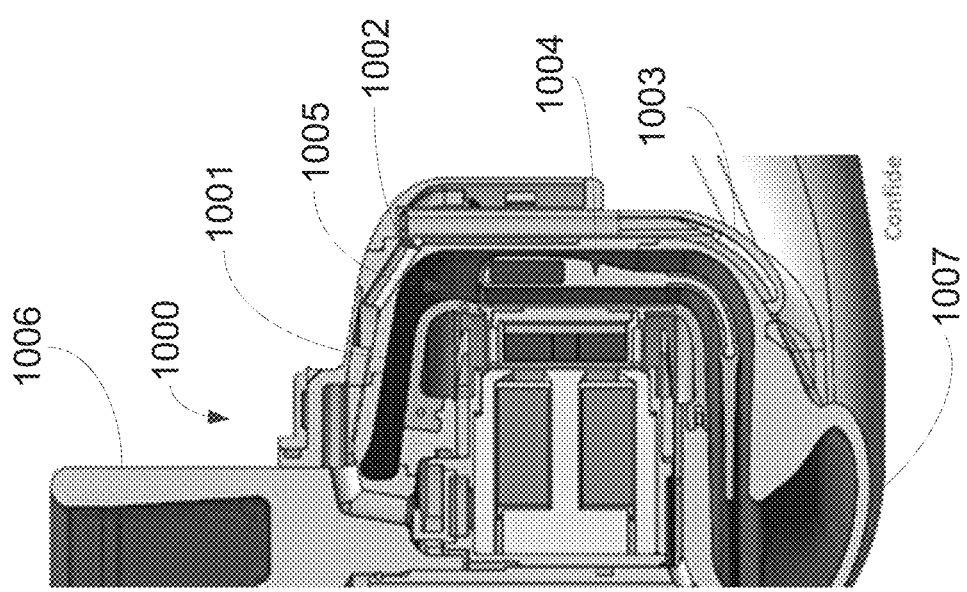
FIG. 22A is a cross-sectional view of a blood pump including an encapsulated actuator assembly.

Referring now to FIG. 22A and FIG. 22B, pump 1000 may be similar to pump 500 of FIG. 17. As shown in FIG. 22A, pump 1000 may include encapsulation assembly 1001, upper housing portion 1002, lower housing portion 1003, and membrane assembly 1004, which may be similar to encapsulation assembly 525, upper housing portion 515, lower housing portion 517, and membrane assembly 535. Encapsulation assembly 1001 on one side and upper housing portion 1002 and lower housing portion 1003 on the other side may form blood flow path 1005. As shown in FIG. 22A, blood may enter the components shown in red and thus may enter inlet cannula 1006, travel in blood flow path 1005 along membrane assembly 1004, and exit outlet cannula 1007.

FIG. 22B is a top-down view of pump 1000 depicting encapsulation assembly 1001, membrane assembly 1004, and a portion upper housing portion 1002. As shown in FIG. 22B, blood path 1005 is defined by encapsulation assembly 1001 and an interior surface of upper housing portion 1002 and is split into two blood flow paths by membrane assembly 1004. Upper housing portion 1002 may further include positioning sensors 1008 that may determine certain operational information about the pump and/or position of membrane assembly 1005.

Figure 23:
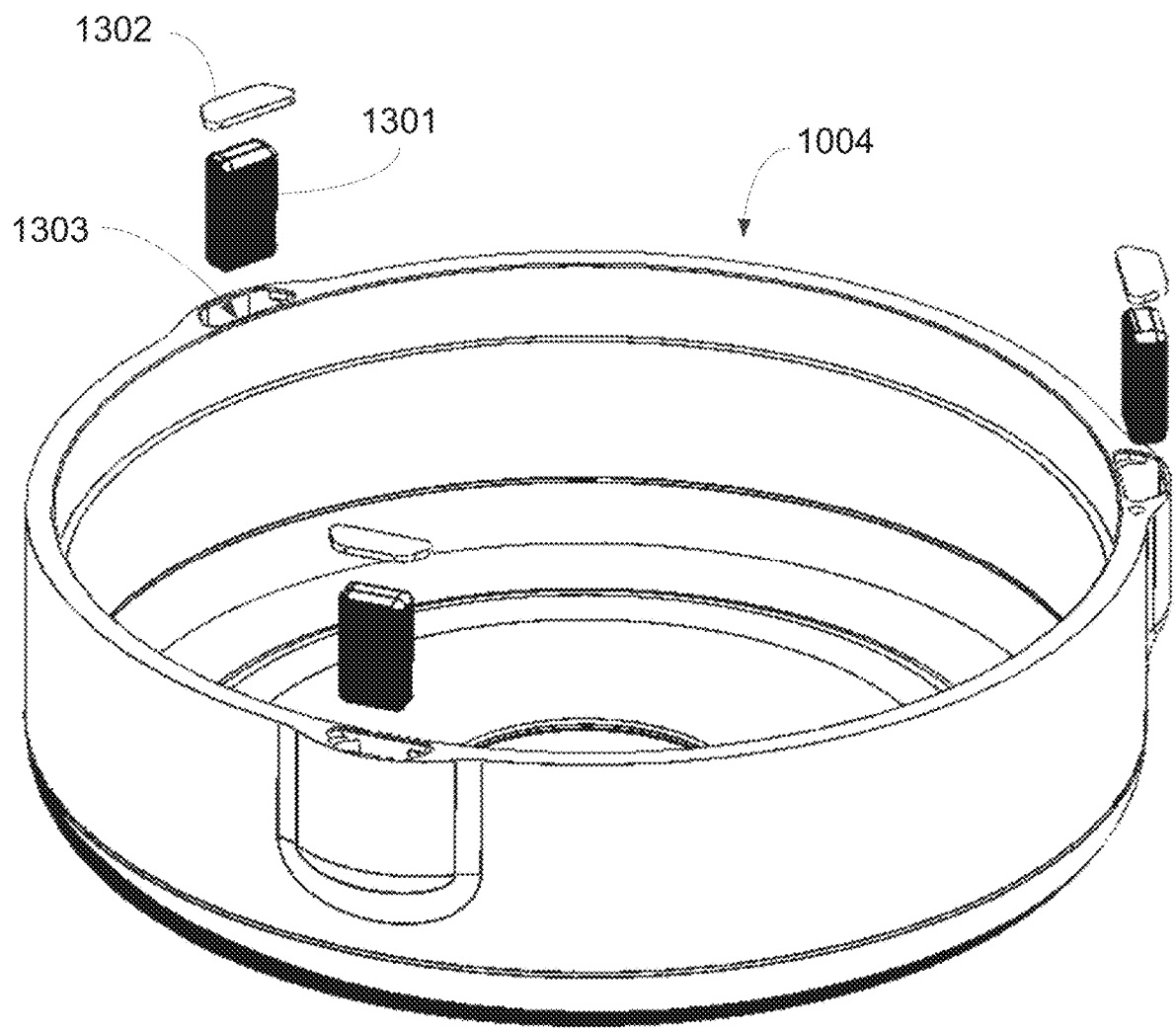
FIG. 23 is an exploded view of a membrane assembly including several sensor targets.

Membrane assembly 1004 is illustrated in greater detail in FIG. 23. As shown in FIG. 23, membrane assembly 1004 may include one or more sensor targets 1301. Sensor targets 1301 may be permanent magnets that are targets for the sensors that are mounted on the outside of the pump housing and may create a moving field for the sensors. Sensors targets 1301 may be used together with positioning sensors 1008 illustrated in FIG. 22B to determine information about the position of membrane assembly 1004 with respect to the pump. Such information may be used to control the motion of the membrane in a closed loop circuit, thereby broadening the range of operation, and preventing excessive amplitude which could damage springs. In one embodiment, sensor targets may be similar to such structure described in further detail in U.S. Pat. No. 10,799,625, which is incorporated herein by reference. Membrane assembly 1004 may include one or more sensor receiving portions 1303 that may be sized and shaped to receive sensor target 1301. Sensor receiving portion 1303 may be sealed with seal portion 1302 that may cover sensor receiving portion 1303 and sensor target 1301.

Figure 24:
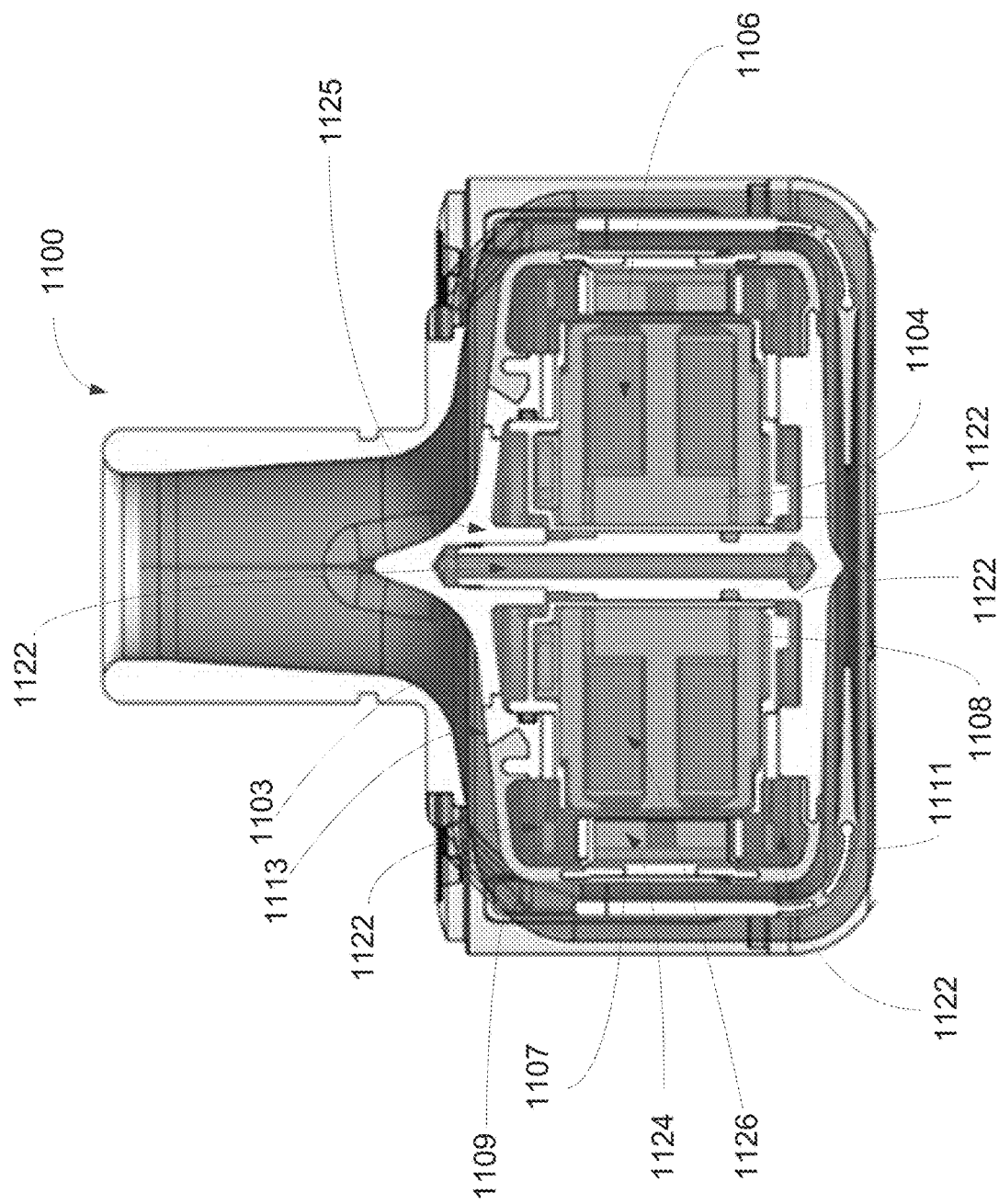
FIG. 24 is a cross-sectional view of a blood pump with an encapsulated actuator assembly illustrating main cavities of the present invention.

Referring now to FIG. 24, a cross-sectional view of pump 1100 with various isolated portions is illustrated. Pump 1100 may be similar to pump 500 in FIG. 17 and may include stator assembly 1103, electromagnetic assembly 1108, magnetic assembly 1107, top encapsulator 1109, and bottom encapsulator 1111, encapsulation assembly 1113. Magnetic assembly 1107 may include isolated portions 1124 that may include gaps and/or empty spaces in magnetic assembly 1107 that may be filled with epoxy backfilling 1124. Electromagnetic assembly 1108 may similarly include isolated portions 1126 that may include gaps and/or empty spaces in electromagnetic assembly 1108 that may be filled with epoxy backfilling. Such epoxy backfilling of isolated portions 1124 and 1126 may protects metallic components and/or wires and/or provide a locking feature to prevent unscrewing. Epoxy backfilling may be added under vacuum before such components are sealed closed. For example, the actuator assembly 1106, which may include core stator portion 1104 and electromechanical assembly 1108, may be hermetically sealed (e.g., by welding of the joints). Core stator portion 1104 may support electromechanical assembly 1108.

Figure 25:
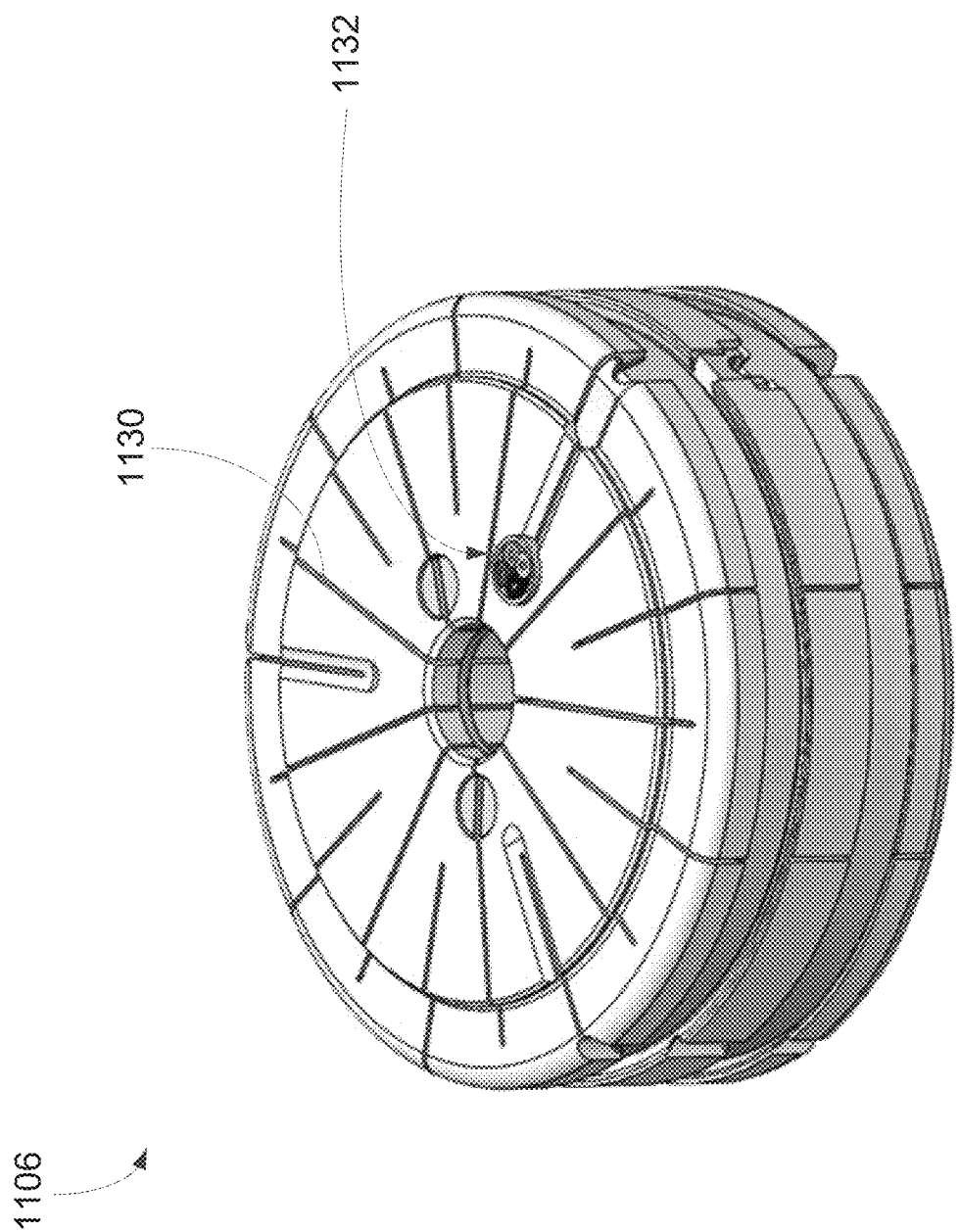
FIG. 25 is a perspective view of an actuator assembly which includes grooves in an outer surface to prevent eddy current circulation in the stator.

Referring now to FIG. 25, a perspective view of actuator assembly 1106 is illustrated. As is shown in FIG. 25, actuator assembly 1106 may include several grooves 1130 positioned on the outer surface of actuator assembly 1106. The grooves 1130 may be sized and arranged to prevent eddy current circulation in the stator. The groves 1130 may also provide the wiring path for connection to the coils. In FIG. 25, wire paths 1132 are shown in one of the circular grooves for connection to the coils. The grooves 1130 may be sized to ease the backfilling of the stator from the inner diameter that may be used for the entry of epoxy to the outer diameter of the actuator assembly.

Referring again to FIG. 24, isolated portions 1122 may be filled with encapsulation fluid. For example, the encapsulation fluid may be a perfluorocarbon such as perfluorodecalin. Isolated portions 1122 may be defined by the space between actuator assembly 1106 and stator assembly 1125, top encapsulator 1109, magnetic assembly 1107, and bottom encapsulator 1111, for example. Encapsulation fluid may be inert fluid that may prevent migration of air, water, and other dissolved components. Encapsulation fluid may be silicone oil, saline, and/or deionized water. Encapsulation fluid may be added to pump 1100 though the following process. First, a two-way tap may be connected to pump 1100 (e.g., through the inlet block). The pump core may then be placed under vacuum as a connector that may be switched to liquid path. Once encapsulation fluid has filled up isolated portions 1122, the chamber pressure may return to atmosphere pressure. Then the encapsulation backfilling access is sealed.

Figure 26A:
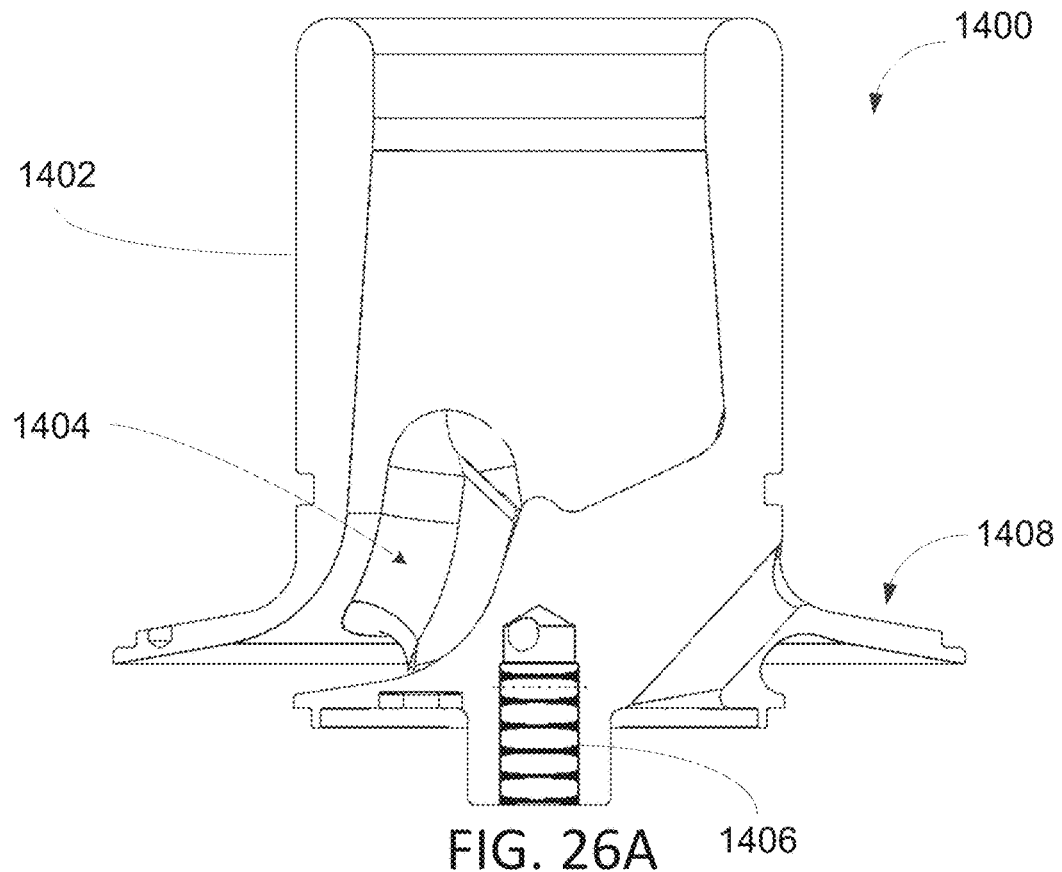
FIG. 26A is a cross-sectional view of an inlet block.
Figure 26B:
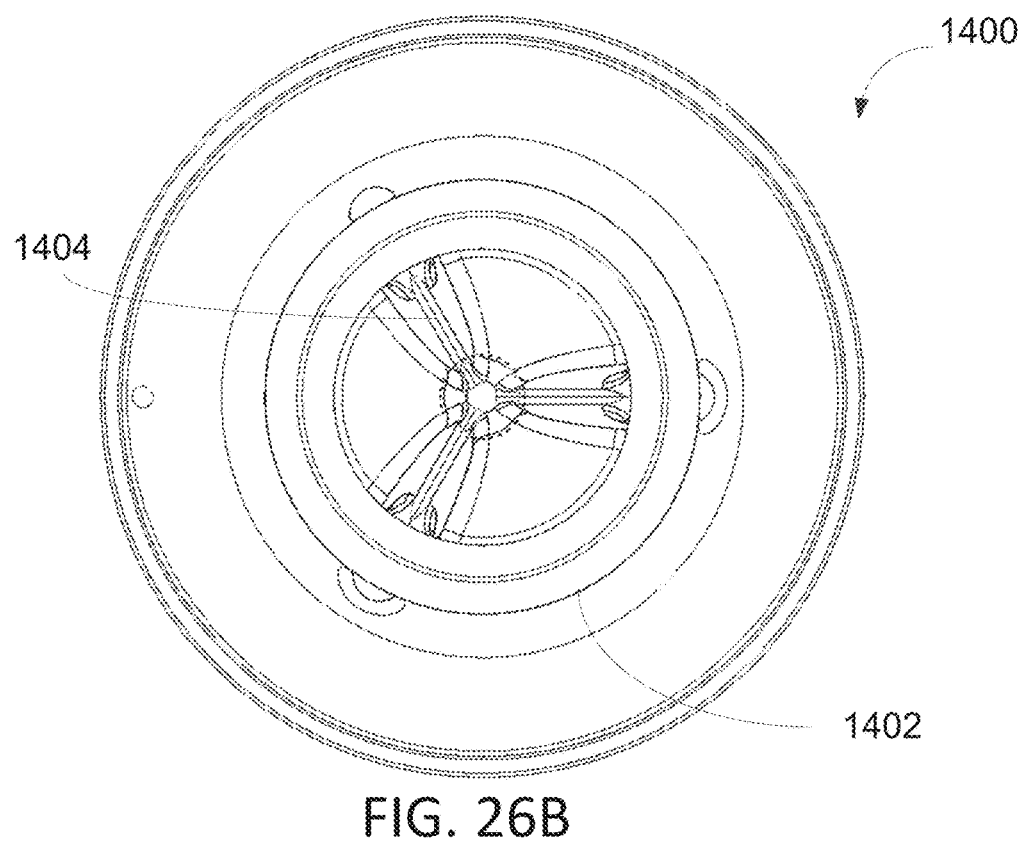
FIG. 26B is a top down view of an inlet including three flow channels.

Referring now to FIG. 26A and FIG. 26B, inlet block 1400 may be similar to inlet block 601 in FIG. 18. As shown in FIG. 26A, inlet block 1400 may include at least a portion of stator assembly as well as inlet cannula 1402. For example, inlet block 1400 may include stator engagement 1406 for engaging the stator assembly. Stator engagement 1406 may be a threaded engagement. Inlet block 1400 may further include several dividers 1404 positioned near the bottom of inlet cannula 1402 which create a mechanical connection between the actuator and the housing. As shown in FIG. 26B, which is a top down view of inlet block 1400, blood may enter the pump through inlet cannula 1402. The shape of dividers 1404 may be designed to prevent flow stagnation to reduce the risk of thrombus formation. As blood traverses inlet block 1400, it may be divided into various blood flow paths by dividers 1404. The inlet block 1400 may include a channel for electrically connecting the actuator assembly to the outside of the pump and/or a channel to fill the cavity 1122 as shown in FIG. 24.

Figure 27A:
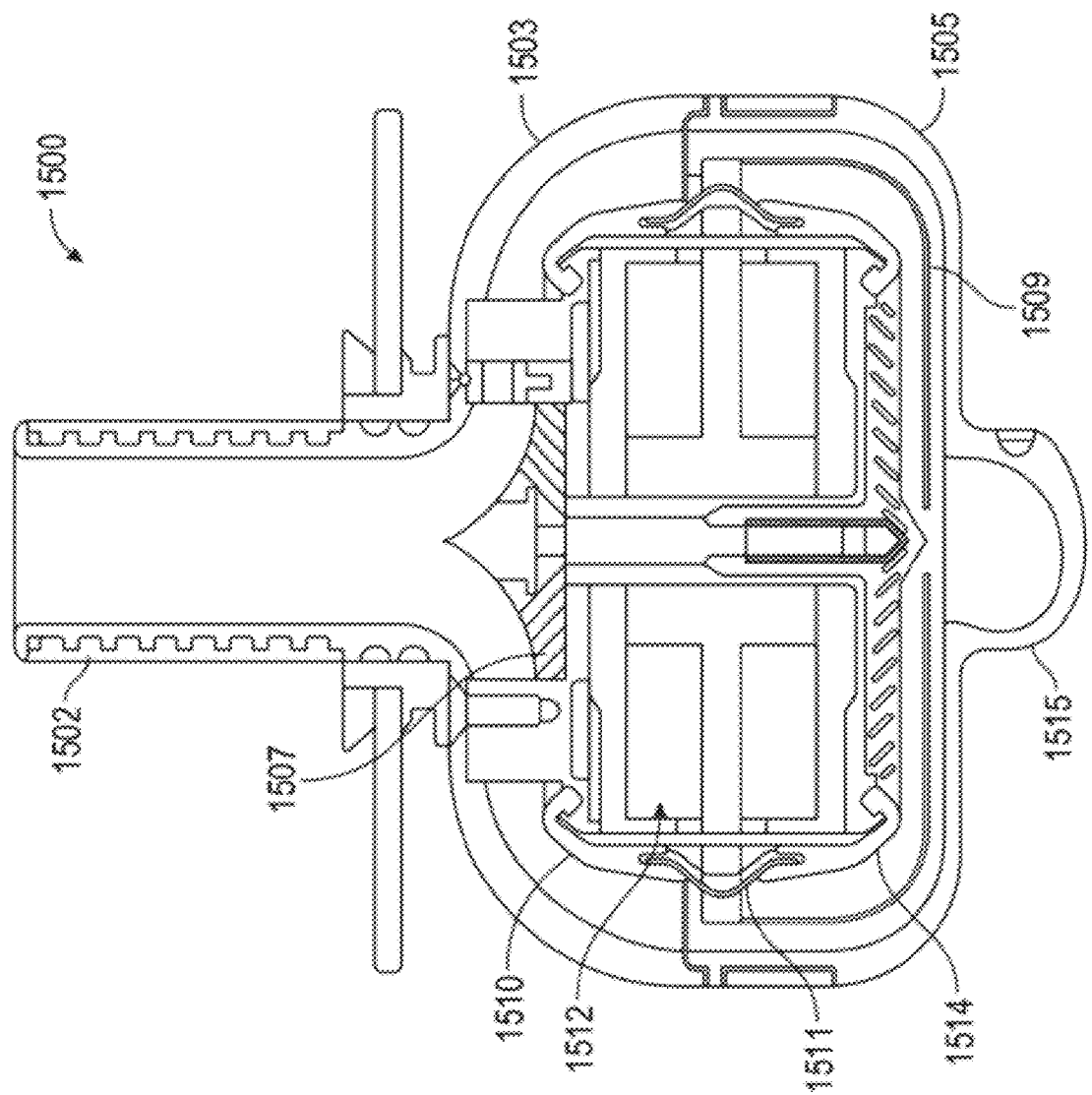
FIG. 27A is a cross-sectional view of a blood pump having springs exterior to an actuator assembly.
Figure 27B:
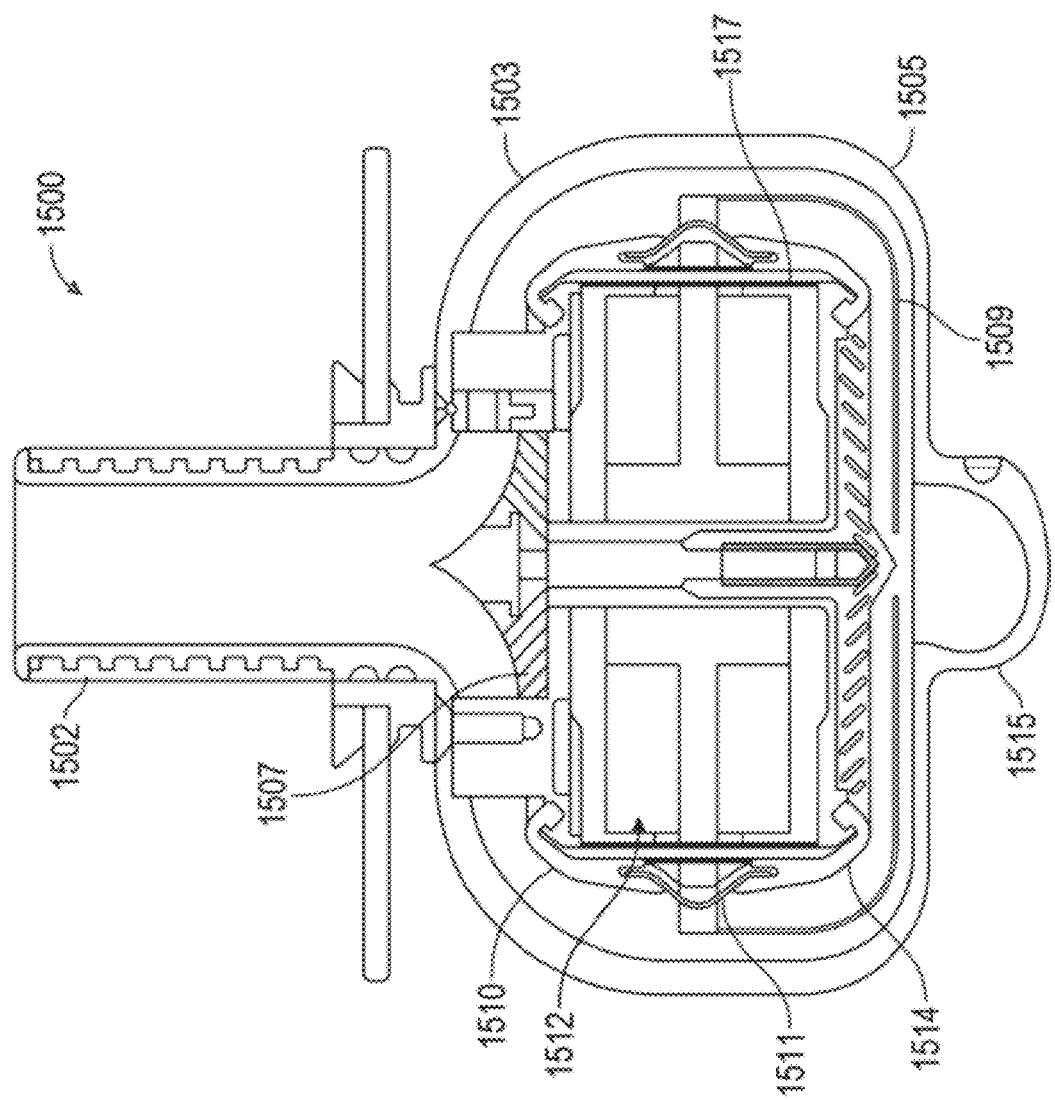
FIG. 27B is a cross-sectional view of a blood pump having a bearing exterior to an actuator assembly.

Referring now to FIGS. 27A-27B, pump 1500 is illustrated. Pump 1500 may be similar to pump 500 in FIG. 17. For example, pump 1500 may include inlet cannula 1502, stator assembly 1507, top encapsulator 1510, magnetic assembly 1511, bottom encapsulator 1514, electromagnetic assembly 1512, upper housing portion 1503, lower housing portion 1505, membrane assembly 1509 and outlet cannula 1515, which may be similar to include inlet cannula 501, stator assembly 511, top encapsulator 532, magnetic assembly 513, bottom encapsulator 531, electromagnetic assembly 503, upper housing portion 515, lower housing portion 517, membrane assembly 538, and outlet cannula 502, respective, as described above with respect to FIG. 17. As shown in FIG. 27A, the elastic properties of top encapsulator 1510 and bottom encapsulator 1514 may provide a spring function to return the actuator to a center position. As shown in FIG. 27B, pump housing 1500 may include one or bearing portions 1517. Bearing portion 1517 may resist radial movement of magnetic assembly 1511 within pump 1500.

Figure 28:
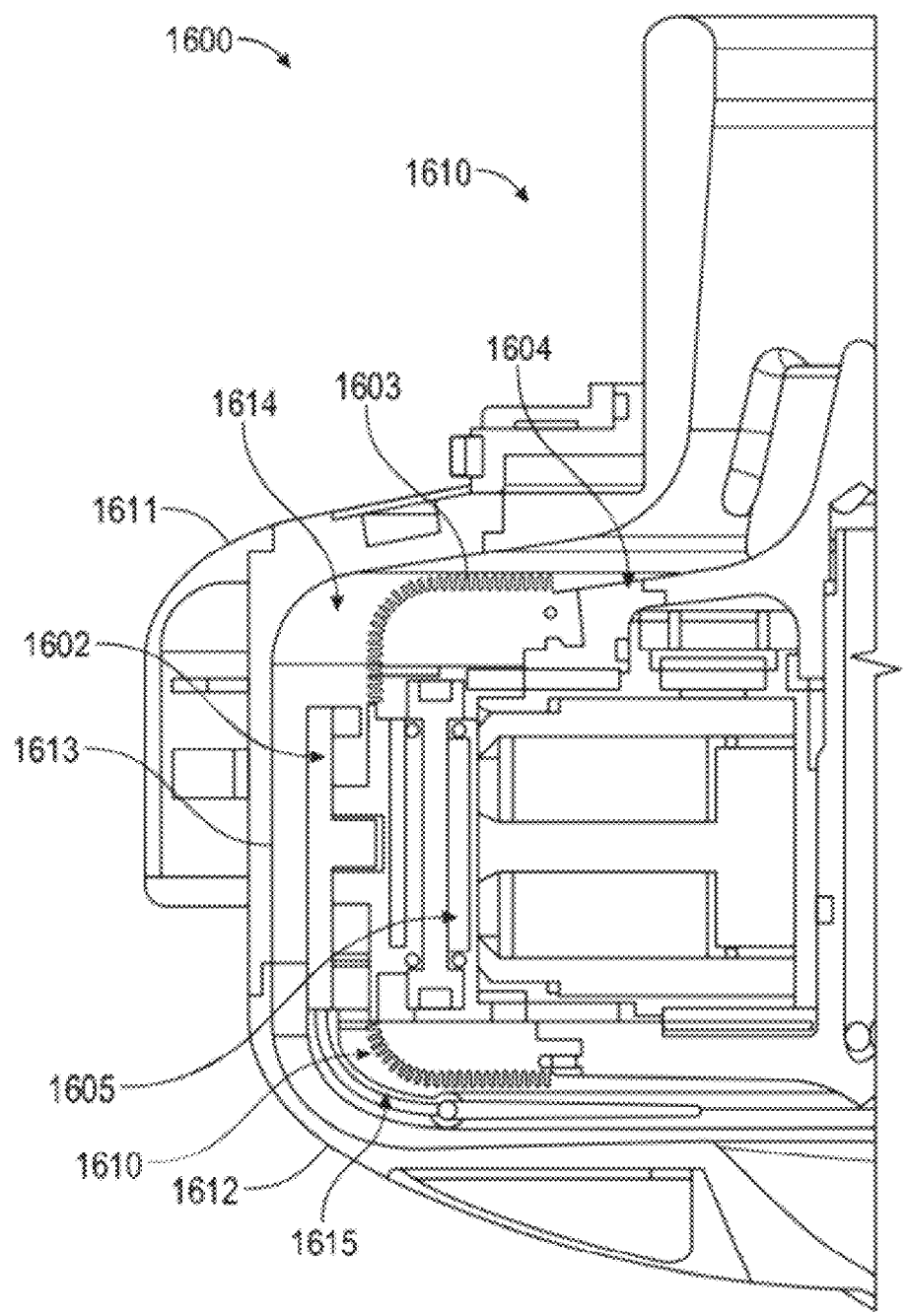
FIG. 28 is a cross-sectional view of a blood pump with an encapsulated actuator assembly having bellows.

Referring now to FIG. 28, pump 1600 is illustrated and may include top encapsulator 1603 and bottom encapsulator 1610, which each may include bellows. Pump 1600 may be similar to pump 500 in FIG. 17. For example, pump 1600 may include inlet cannula 1610, stator assembly 1604, magnetic assembly 1602, bottom encapsulator 1610, electromagnetic assembly 1605, upper housing portion 1611, lower housing portion 1612, and membrane assembly 1613, which may be similar to include inlet cannula 501, stator assembly 511, magnetic assembly 513, electromagnetic assembly 503, upper housing portion 515, lower housing portion 517, and membrane assembly 538 of FIG. 17, respectively. Top encapsulator 1603 and bottom encapsulator 1610 may be similar to top encapsulator 532 and bottom encapsulator 531 of FIG. 17, however, top encapsulator 1603 may include bellows 1614 and bottom encapsulator 1610 may include bellows 1615. For example, top encapsulator 1603 and bottom encapsulator 1610 may be formed from one or more well-known metals or metal alloys and bellows 1614 and 1615 may be pleated bellows. In this manner, top encapsulator 1614 and bottom encapsulators 1614 may be made of metal but may still be flexible and facilitate movement of magnetic assembly 1602.

Figure 29A:
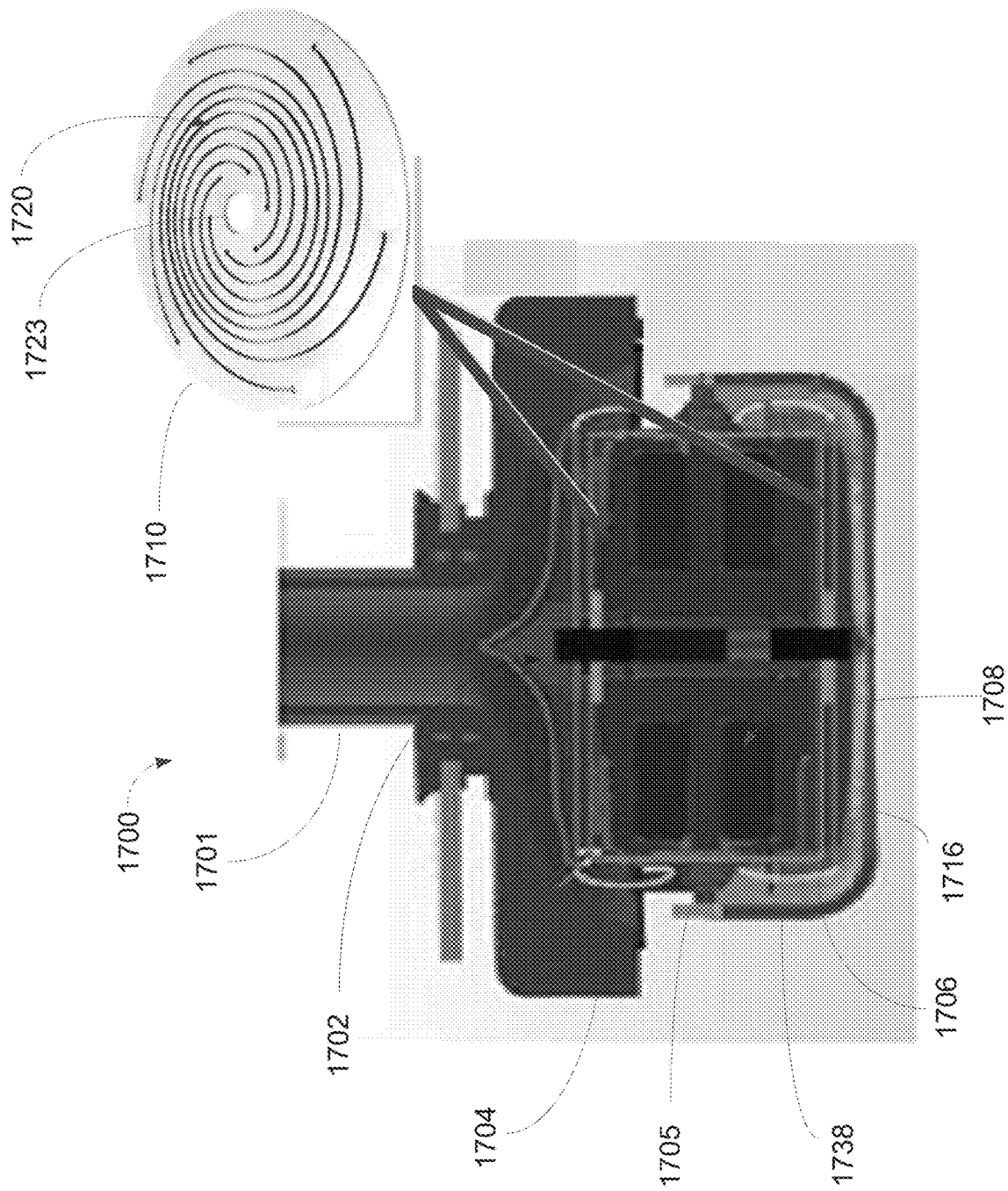
FIG. 29A is a cross-sectional view of a blood pump with flexure spring assembly.
Figure 29B:
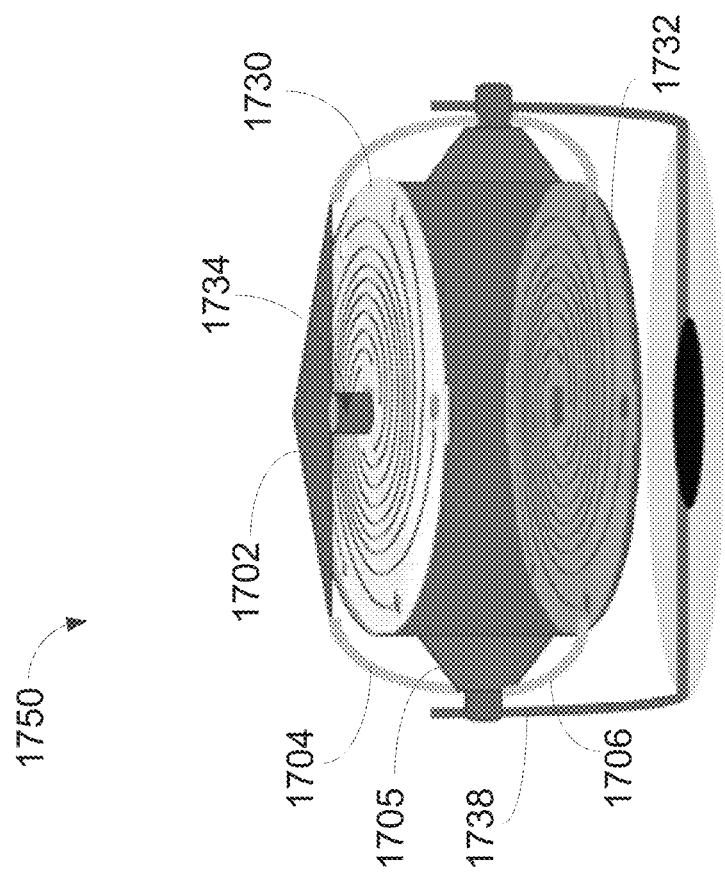
FIG. 29B is a perspective view of a flexure spring assembly.

Referring now to FIGS. 29A-29B, pump 1700 including flexure springs 1710 attached to actuator compartment 1716 is illustrated. Pump 1700 may be similar to pump 500 in FIG. 17. For example, pump 1700 may include inlet cannula 1701, stator assembly 1702, top encapsulator 1704, magnetic assembly 1705, bottom encapsulator 1706, electromagnetic assembly 1708, and membrane assembly 1738, which may be similar to include inlet cannula 501, stator assembly 511, top encapsulator 532, magnetic assembly 513, bottom encapsulator 531, electromagnetic assembly 503, and membrane assembly 538 of FIG. 17.

Membrane assembly 1738 may be coupled to magnetic assembly 1705. Electromagnetic assembly 1708 may be positioned within actuator compartment 1716 which may be cylindrical or similarly shaped structure acting as a physical connection between the magnet ring and the flexure bearing, which may be porous. For example, actuator compartment may be a thin walled cylinder. Electromagnetic assembly 1708 may be isolated from the rest of pump 1700 by top encapsulator 1704 and bottom encapsulator 1706. Actuator compartment 1716 may be connected to stator assembly 1702 via one or more flexure (spiral) springs 1701. Flexure spring 1710 is shown in more detail in FIG. 29B. Flexure spring 1710 may include several curved through cuts 1720 achieving a spiral shape on flexure spring 1710. Flexure spring 1710 may optionally include several actuator compartment engagement portions along a permit of flexure spring 1710. Flexure spring 1710 may connect to stator assembly 1702 at stator receiving portion 1723 and may connect to actuator compartment 1716 via actuator compartment engagement portions 1722. Flexure spring 1710 may incorporate dimensions and material properties that allow it to provide a spring force. Actuator compartment 1716 may be coupled to magnetic assembly 1705; in embodiments, actuator compartment 1716 and magnetic assembly 1705 are flexibly connected by a flexure bearing. The flexure bearing may provide restoring force and may resist radial movement.

Referring now to FIG. 29B, perspective views of flexure springs and the actuator compartment are illustrated. As shown in FIG. 29B, stator assembly 1702 may include central component 1734 which may be cylindrical in shape and may engage upper flexural spring 1730 and lower flexural spring 1732, each of which may be similar to flexural spring 1710. Upper flexural spring 1730 and lower flexural spring 1732 may each also be coupled to actuator compartment 1716, which may be rigidly coupled to magnetic assembly 1705. Top encapsulator 1704 and bottom encapsulator 1706 may each be coupled to stator assembly 1702 and magnetic assembly 1705. The electromagnetic assembly (not shown) may be disposed in actuator compartment 1716 but may be rigidly connected to central component 1734 such that actuator compartment 1716 is free to move axially with respect to stator assembly 1702. Membrane assembly 1738 may be coupled to magnetic assembly 1705.

As magnetic assembly 1705 interacts with electromagnetic assembly, magnetic assembly 1705 may be caused to reciprocate up and down with respect to stator assembly 1702. As actuator compartment 1716 may be rigidly coupled to magnetic assembly 1705, actuator compartment 1716 may similarly reciprocate. Upper flexure spring 1730 and lower flexure spring 1732 may permit actuator compartment 1716 to move in the axial direction and upper flexure spring 1730 and lower flexure spring 1732 may cause actuator compartment 1716 and thus magnetic assembly 1738 to return to a neutral position via a spring force in upper flexure spring 1730 and lower flexure spring 1732. Upper flexure spring 1730 and lower flexure spring 1732 may further resist twist or tilt of actuator component 1716 and magnetic assembly 1705.

While various illustrative embodiments of the invention are described above, it will be apparent to one skilled in the art that various changes and modifications may be made therein without departing from the invention. For example, pump assembly 70 shown in FIG. 9 may be ordered differently and may include additional or fewer components of various sizes and composition. The appended claims are intended to cover all such changes and modifications that fall within the true spirit and scope of the invention.

What is claimed is:

1. A blood pump system comprising:
    a housing having an inlet and an outlet configured to be in fluid communication with a patient's circulatory system;
    a membrane disposed within the housing;
    an electromagnetic coil disposed within the housing, the electromagnetic coil configured to cause the membrane to reciprocate to pump blood;
    a moving magnetic portion configured to extend around and to move with respect to the electromagnetic coil; and
    a top and bottom encapsulator coupled to the moving magnet portion and configured to obstruct blood flow between the electromagnetic coil and the moving magnet portion such that the blood does not contact the electromagnetic coil and the moving magnet portion, the top and bottom encapsulator disposed within the housing and configured to define a blood flow channel between the housing and the top and bottom encapsulator,
    wherein, during operation, blood enters the inlet, flow between the housing and the top and bottom encapsulator in the blood flow channel, and is propelled across the membrane to the outlet to pump the blood.

2. The blood pump system of claim 1, wherein the electromagnetic coil is disposed between an upper stator portion and a lower stator portion.

3. The blood pump system of claim 2, further comprising at least one spring coupled to the upper stator portion wherein the at least one spring and the top encapsulator apply a spring force on the moving magnet portion.

4. The blood pump system of claim 1, wherein the moving magnet portion is annular.

5. The blood pump system of claim 1, wherein the top and bottom encapsulator inhibit damage to the blood due to shear conditions.

6. The blood pump system of claim 1, wherein the blood flow channel inhibits damage to von Willebrand Factor multimers in the blood.

7. The blood pump system of claim 1, wherein the blood flow channel is sized and configured to facilitate blood flow towards the outlet and resist blood flow towards the inlet.

8. The blood pump system of claim 1, wherein the flow channel is sized and configured to inhibit shear conditions of the blood in the blood flow channel and to inhibit recirculation of the blood in the blood flow channel.

9. The blood pump system of claim 1, further comprising an encapsulation fluid disposed between the top and bottom encapsulator and the actuator assembly electromagnetic coil.

10. The blood pump system of claim 9, wherein the encapsulation fluid is a perfluorocarbon.

11. The blood pump system of claim 9, wherein the encapsulation fluid is selected from one of silicone oil, saline, deionized water, or perfluorodecalin.

12. The blood pump system of claim 1, wherein:
    the electromagnetic coil is disposed between an upper stator portion and a lower stator portion,
    the top encapsulator is coupled to the top stator portion and the magnetic assembly,
    the bottom encapsulator is coupled to the bottom stator portion and the magnetic assembly,
    the membrane is flexible,
    the electromagnetic coil is configured to generate a magnetic field, and the moving magnet portion is configured to reciprocate responsive to the magnetic field and cause the membrane to reciprocate responsive to the moving magnet portion.

13. The blood pump system of claim 12, wherein the moving magnet portion comprises a Halbach array.

14. The blood pump system of claim 12, further comprising at least one spring coupled to the moving magnet portion assembly and the upper stator portion assembly.

15. The blood pump system of claim 12, further comprising encapsulation fluid, wherein the encapsulation fluid is disposed between the top and bottom encapsulator, the moving magnet portion assembly, and the electromagnetic coil actuator assembly.

16. The blood pump system of claim 15, wherein the blood flow channel is configured to inhibit recirculation of the blood.

17. The blood pump system of claim 12, wherein the blood flow channel is sized and configured to facilitate blood flow towards the outlet and resist blood flow towards the inlet.

* * * * *